(12) United States Patent
Singh et al.

(10) Patent No.: US 6,831,075 B2
(45) Date of Patent: Dec. 14, 2004

(54) HETEROCYCLIC SUBSTITUTED PYRAZOLONES

(75) Inventors: Jasbir Singh, Gilbertsville, PA (US); Rabindranath Tripathy, Landenberg, PA (US)

(73) Assignee: Cephalon, Inc., West Chester, PA (US)

( * ) Notice: Subject to any disclaimer, the term of this patent is extended or adjusted under 35 U.S.C. 154(b) by 0 days.

(21) Appl. No.: 10/225,670

(22) Filed: Aug. 22, 2002

(65) Prior Publication Data

US 2003/0162775 A1 Aug. 28, 2003

Related U.S. Application Data

(63) Continuation of application No. 09/702,191, filed on Oct. 31, 2000, now Pat. No. 6,455,525.
(60) Provisional application No. 60/163,377, filed on Nov. 4, 1999.

(51) Int. Cl.[7] .................. A61K 31/33; A61K 31/433; C07D 239/00; C07D 241/00; C07D 231/00
(52) U.S. Cl. .................. 514/183; 514/241; 514/242; 514/247; 514/252.1; 514/255.05; 514/256; 514/277; 514/403; 514/406; 514/407; 544/180; 544/182; 544/224; 544/238; 544/242; 544/336; 546/1; 548/356.1; 548/365.1; 548/364.1; 548/364.7; 548/367.1; 548/379.1; 549/49; 549/74; 549/200; 549/229
(58) Field of Search .................. 514/183, 241, 514/242, 247, 252.1, 256, 255.05, 277, 403, 406, 407; 546/1; 544/180, 182, 224, 238, 242, 336; 548/356.1, 364, 364.7, 379.1, 386.1, 388.1, 364.1, 367.1; 549/49, 229, 74, 200

(56) References Cited

U.S. PATENT DOCUMENTS

| | | | |
|---|---|---|---|
| 3,717,629 A | 2/1973 | Maier et al. | 260/244 |
| 4,035,190 A | 7/1977 | Beretta et al. | 96/127 |
| 4,909,827 A | 3/1990 | Gehring et al. | 71/92 |
| 5,174,808 A | 12/1992 | Wroblowsky et al. | 71/92 |
| 6,034,099 A | 3/2000 | Pamukcu et al. | 514/310 |
| 6,455,525 B1 * | 9/2002 | Singh et al. | 514/241 |

FOREIGN PATENT DOCUMENTS

| | | | |
|---|---|---|---|
| DE | 2045049 | * | 3/1972 |
| FR | 2081595 | | 12/1971 |
| FR | 2224141 | | 10/1974 |
| JP | 10-151868 | | 6/1998 |
| WO | WO 00/51989 | | 9/2000 |
| WO | WO 01/09121 | | 2/2001 |

OTHER PUBLICATIONS

Coyle et al, Science, vol. 219, 1184–90(1983).*
Cecil Textbook of Medicine, 2oth Edn.,vol. 1, pp. 100401010(1996).*
Ucken et al, Current Cancer Drug Targets, 1,59–71(2001).*
Chemical Abstract DN 114:6530, also cited as JP02193994.*
Kharchenko et al, Chemica Abstract DN 93:8079, also cited asVses, Nauchn. Konf. Khim. Teckhnol. Furanovykh Soedin.,(Tezisy Dok., 3rd,112,(1978).*
Kubota etal, Chemical Abstract DN 63:80597, also cited as Bull. of the Chem. Soc. of Japan, 38/7,1191–4(1965).*

* cited by examiner

*Primary Examiner*—Richard L. Raymond
*Assistant Examiner*—Sudhaker B. Patel
(74) *Attorney, Agent, or Firm*—Robert T. Hrubiec; Scott K. Larsen

(57) ABSTRACT

The present invention is directed to novel heterocyclic substituted pyrazolones, including pharmaceutical compositions, diagnostic kits, assay standards or reagents containing the same, and methods of using the same as therapeutics. The invention is also directed to intermediates and processes for making these novel compounds.

29 Claims, No Drawings

HETEROCYCLIC SUBSTITUTED PYRAZOLONES

This application is a continuation of Ser. No. 09/702,191 filed Oct. 31, 2000 now U.S. Pat. No. 6,455,525 which claims benefit of 60/163,377 filed Nov. 4, 1999.

FIELD OF THE INVENTION

The present invention relates generally to heterocyclic substituted pyrazolones, including pharmaceutical compositions, diagnostic kits, assay standards or reagents containing the same, and methods of using the same as therapeutics. The invention is also directed to intermediates and processes for making these novel compounds.

BACKGROUND OF THE INVENTION

Protein kinases play a critical role in the control of cell growth and differentiation. Aberrant expression or mutations in protein kinases have been shown to lead to uncontrolled cell proliferation, such as malignant tumor growth, and various defects in developmental processes, including cell migration and invasion, and angiogenesis. Protein kinases are therefore critical to the control, regulation, and modulation of cell proliferation in diseases and disorders associated with abnormal cell proliferation. Protein kinases have also been implicated as targets in central nervous system disorders such as Alzheimer's disease, inflammatory disorders such as psoriasis, bone diseases such as osteoporosis, atheroscleroses, restenosis, thrombosis, metabolic disorders such as diabetes, and infectious diseases such as viral and fungal infections.

One of the most commonly studied pathways involving kinase regulation is cellular signaling from receptors at the cell surface to the nucleus. Generally, the function of each receptor is determined by its pattern of expression, ligand availability, and the array of downstream signal transduction pathways that are activated by a particular receptor. One example of this pathway includes a cascade of kinases in which members of the Growth Factor receptor Tyrosine Kinases deliver signals via phosphorylation to other kinases such as Src Tyrosine kinase, and the Raf, Mek and Erk serine/threonine kinase families. Each of these kinases is represented by several family members which play related, but functionally distinct roles. The loss of regulation of the growth factor signaling pathway is a frequent occurrence in cancer as well as other disease states. Fearon, *Genetic Lesions in Human Cancer, Molecular Oncology*, 1996, 143–178.

The raf1 serine/threonine kinase can be activated by the known oncogene product ras. The raf kinase enzyme positively regulates cell division through the Raf/MEK/ERK protein kinase cascade. This activation is the result of cRaf1 catalyzed phosphorylation of the protein kinase, MEK1, which phosphorylates and activates the protein kinase ERK. ERK phosphorylates and regulates transcription factors required for cell division. Avruch et al., *TIBS*, 1994 (19) 279–283. cRaf1 negatively regulates cell death by modulation of the activity of Bcl-2, a critical regulator of apoptosis. This regulation involves direct phosphorylation of Bcl-2 family members. Gajewski and Thompson, *Cell*, 1996 (87) 619–628.

These aspects of cRaf1 -mediated regulation of cell proliferation require the kinase activity of cRaf1. It has also been reported that the reduction of Raf protein levels correlates with a reduction in tumor growth rate in vivo tumor mouse models. Monia, Johnston, Geiger, Muller, and Fubro, *Nature Medicine*, Vol. 2, No. 6, June 1996, 668–674. Inhibitors of the kinase activity of cRaf1 should therefore provide effective treatment for a wide variety of human cancers.

Activation of the MAP kinase signaling pathways represents an attractive target for tumor therapy by inhibiting one or more of the kinases involved. An additional member of the MAP kinase family of proteins is the p38 kinase, alternatively known as the cytokine suppressive drug binding protein or reactivation kinase, RK. Activation of this kinase has been implicated in the production of proinflammatory cytokines such as IL-1 and TNF. Inhibition of this kinase could therefore offer a treatment for disease states in which disregulated cytokine production is involved.

The signals mediated by kinases have also been shown to control cell growth, cell death and differentiation in the cell by regulating the processes of the cell cycle. Progression through the eukaryotic cell cycle is controlled by a family of kinases called cyclin dependent kinases (CDKs). The loss of control of CDK regulation is a frequent event in hyperproliferative diseases and cancer.

Inhibitors of kinases involved in mediating or maintaining particular disease states represent novel therapies for these disorders. Examples of such kinases include inhibition of Src, raf, and the cyclin-dependent kinases (CDK) 1, 2, and 4 in cancer, CDK2 or PDGF-R kinase in restenosis, CDK5 and GSK3 kinases in Alzheimers, c-Src kinase in osteoporosis, GSK-3 kinase in type-2 diabetes, p38 kinase in inflammation, VEGF-R 1–3 and TIE-1 and -2 kinases in angiogenesis, UL97 kinase in viral infections, CSF-1R kinase in bone and hematopoetic diseases, and Lck kinase in autoimmune diseases and transplant rejection.

Thus, there is a need for novel classes of compounds which demonstrate activity toward receptor and non-receptor types of protein kinases. It has been discovered that a class of compounds, referred to herein as heterocyclic-substituted pyrazolones, are useful as agents for the regulation of protein kinase. The present invention is therefore directed to, inter alia, their use as therapetic agents for the treatment of the foregoing disorders.

SUMMARY OF THE INVENTION

Accordingly, one object of the present invention is to provide novel compounds which are kinase inhibitors. In certain objects, the compounds of the present invention are inhibitors of one or more of vascular endothelial growth factor receptor (VEGFR) kinase, trkA tyrosine kinase (trkA), mixed lineage kinase (MLK) or fibroplast growth factor receptor kinase (FGFR).

It is another object of the present invention to provide pharmaceutical compositions comprising a pharmaceutically acceptable carrier and a therapeutically effective amount of at least one of the compounds of the present invention, or a pharmaceutically acceptable salt form thereof.

It is another object of the present invention to provide a novel method for treating or preventing disorders associated with the aberrant activity of protein kinases. In certain objects, the disorders are characterized by the aberrant activity of one or more of the vascular endothelial growth factor receptor (VEGFR) kinase, trkA tyrosine kinase (trkA), mixed lineage kinase (MLK) or fibroplast growth factor receptor kinase (FGFR), and the method comprises administering to a host in need of such treatment or prevention a therapeutically effective amount of at least one of the compounds of the present invention.

It is another object of the present invention to provide a method for inhibiting protein kinases in a body fluid sample.

In certain objects, the method comprises treating the body fluid sample with an effective amount of at least one of the compounds of the present invention to inhibit one or more protein kinases.

It is another object of the present invention to provide a kit or container containing at least one of the compounds of the present invention in an amount effective for use as a diagnostic, standard or reagent.

These and other important objects, which will become apparent during the following detailed description, have been achieved by the inventor's discovery that compounds of Formula I:

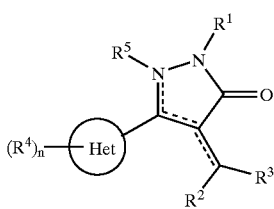

stereoisomeric forms, mixtures of stereoisomeric forms, or pharmaceutically acceptable salt forms thereof, wherein $R^1$, $R^2$, $R^3$, $R^4$, $R^5$, and Het are defined below, are effective kinase inhibitors.

DETAILED DESCRIPTION OF THE EMBODIMENTS

Thus, in a first embodiment, the present invention provides a novel compound of Formula I:

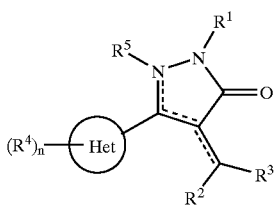

or a stereoisomer or pharmaceutically acceptable salt thereof, wherein:

Het is a heterocycle;

$R^1$ is selected from H, $C_{1-10}$ alkyl substituted with 0–5 $R^6$, $C_{2-8}$ alkenyl substituted with 0–5 $R^6$, $C_{2-8}$ alkynyl substituted with 0–5 $R^6$, $NR^aR^a$, $C(=O)R^b$, $C(=O)NHR^a$, $CO_2R^c$, and heterocycle substituted with 0–5 $R^6$;

with the provisos that when $R^1$ and Het are both 2-pyridinyl, $R^2$ and $R^3$ are other than 4-diethylamino-2-phenyl; and when $R^1$ is 4-carboxy-phenethyl, Het and either $R^2$ or $R^3$ are other than both dimethylamino-thiophene;

$R^2$ and $R^3$ are independently selected from H, $C_{1-2}$ alkyl substituted with 1–5 $R^6$, $C_{3-10}$ alkyl substituted with 0–5 $R^6$, $C_{2-8}$ alkenyl substituted with 0–5 $R^i$, $C_{2-6}$ alkynyl, Cl, Br, I CN, $(CH_2)_rNR^aR^a$, $(CH_2)_rOR^c$, $(CH_2)_rSR^c(CH_2)_rC(=O)R^b$, $(CH_2)_rCO_2R^c$, $(CH_2)_rOC(=O)R^b$, $(CH_2)_rC(=O)NR^aR^a$, $(CH_2)_rNR^aC(=O)R^b$, $(CH_2)_rNR^aC(=O)OR^b$, $(CH_2)_rOC(=O)NHR^a$, $(CH_2)_rNR^aS(=O)_2R^b$, $(CH_2)_rS(=O)_2NR^aR^a$, $(CH_2)_rS(O)_pR^b$, $(CH_2)_r$carbocycle substituted with 0–5 $R^4$, and $(CH_2)_r$heterocycle substituted with 0–5 $R^4$;

with the provisos that $R^2$ and $R^3$ are other than both H or both SMe; and when $R^2$ is H, and $R^3$ is phenyl, Het is not 2-furanyl;

alternatively, $R^2$ and $R^3$ join to form a heterocycle substituted with 0–4 $R^4$, with the proviso that the heterocycle is other than 2-thiazolidinyl or 5-methyl-2-oxazolidinyl;

$R^4$, at each occurrence, is independently selected from H, F, Cl, Br, I, CN, $CF_2CF_3$, $CF_3$, $NO_2$, CN, OH, $NR^aR^a$, $OR^c$, $C(=O)R^b$, $CO_2R^c$, $OC(=O)R^b$, $NR^aC(=O)R^b$, $C(=O)NR^aR^a$, $OC(=O)NR^aR^a$, $NR^aC(=O)R^b$, $NR^aS(=O)_2R^b$, $S(=O)_2NR^aR^a$, $NR^aC(=S)R^b$, $C(=S)NR^aR^a$, $NR^aC(=O)NR^aR^a$, $NR^aC(=S)NR^aR^a$, $CH=NOR^c$, $CH=NR^a$, $CH=NNR^aR^a$, $(CH_2)_rS(O)_pR^b$, $O(CH_2)_qNR^aR^a$, $O(CH_2)_qOR^c$, $(CH_2)_rOR^d$, $(CH_2)_rC(=O)R^d$, $(CH_2)_rNHR^d$, $(CH_2)_rS(O)_pR^{d'}$, $C_{1-10}$ alkyl substituted with 0–5 $R^6$, $C_{2-8}$ alkenyl substituted with 0–5 $R^6$, $C_{2-8}$ alkynyl substituted with 0–5 $R^6$, carbocycle substituted with 0–5 $R^6$, and heterocycle substituted with 0–5 $R^6$;

$R^5$ is either absent or is selected from H, $C_{1-8}$ alkyl, $C_{2-6}$ alkenyl, $C_{2-6}$ alkynyl, $(CH_2)_rC_{3-6}$ cycloalkyl, and $(CH_2)_r$phenyl;

$R^6$, at each occurrence, is selected from $C_{1-6}$ alkyl substituted with 0–5 $R^h$, $C_{2-8}$ alkenyl, $C_{2-8}$ alkynyl, F, Cl, Br, I, CN, $CF_2CF_3$, $CF_3$, $NO_2$, CN, $NR^fR^f$, $OR^f$, $C(=O)R^f$, $CO_2R^f$, $OC(=O)R^g$, $NR^fC(=O)R^f$, $C(=O)NR^fR^f$, $OC(=O)NR^fR^f$, $NR^eC(=O)OR^g$, $NR^eS(=O)_2R^g$, $S(=O)_2NR^fR^f$, $NR^aC(=S)R^g$, $C(=S)NR^fR^f$, $NR^fC(=O)$ $NR^fR^f$, $NR^fC(=S)NR^fR^f$, $CH=NOR^e$, $CH=NR^e$, $CH=NNR^eR^e$, $S(O)_pR^f$, $O(CH_2)_pNR^fR^f$, $O(CH_2)_pOR^f$, $OR^d$, $NHR^d$, $C(=O)R^d$, $S(O)_pR^{d'}$, carbocycle substituted with 0–5 $R^h$, heterocycle substituted with 0–5 $R^h$, $P(=O)(OR^c)_2$, and a $C_{5-7}$ monosaccharide wherein each hydroxyl group of the monosaccharide is unsubstituted or replaced by a group selected from H, $C_{1-4}$ alkyl, $C_{1-4}$ alkoxy, and $OC(=O)C_{1-4}$ alkyl;

$R^a$, at each occurrence, is independently selected from H, $C_{1-6}$ alkyl, $C_{2-6}$ alkenyl, $C_{2-6}$ alkynyl, $(CH_2)_rC_{3-6}$ cycloalkyl, and $(CH_2)_r$phenyl, wherein when $R^a$ is other than H, $R^a$ is substituted with 0–5 $R^h$;

alternatively, two $R^a$ may join to form a linker selected from $(CH_2)_qO(CH_2)_q$, $(CH_2)_qS(CH_2)_q$, and $(CH_2)_m$, wherein the linker is substituted with 0–5 $R^h$;

$R^b$, at each occurrence, is independently selected from $C_{1-6}$ alkyl, $C_{2-6}$ alkenyl, $C_{2-6}$ alkynyl, $(CH_2)_r$phenyl, and $(CH_2)_r$heterocycle, wherein $R^b$ is substituted with 0–5 $R^h$;

$R^c$, at each occurrence, is independently selected from H, $C_{1-6}$ alkyl, $C_{2-6}$ alkenyl, $C_{2-6}$ alkynyl, $C_{3-6}$ cycloalkyl, and $(CH_2)_r$phenyl, wherein when $R^c$ is other than H, $R^c$ is substituted with 0–5 $R^h$;

$R^d$, at each occurrence, is the residue of an amino acid after the hydroxyl group of the carboxyl group is removed;

$R^{d'}$, at each occurrence, is the residue of an amino acid after the hydrogen of the amine is removed;

$R^e$, at each occurrence, is selected from H and $C_{1-6}$ alkyl;

$R^f$, at each occurrence, is selected from H, $C_{1-6}$ alkyl substituted with 0–5 $R^h$, and $(CH_2)_r$phenyl substituted with 0–5 $R^h$;

$R^g$, at each occurrence, is selected from $C_{1-6}$ alkyl substituted with 0–5 $R^h$ and $(CH_2)_r$phenyl substituted with 0–5 $R^h$;

$R^h$, at each occurrence, is selected from F, Cl, Br, I, OH, $NO_2$, CN, $CF_3$, $CF_2CF_3$, $C_{1-4}$ alkyl, $C_{2-6}$ alkenyl, $C_{2-6}$ alkynyl, alkoxy, $C_{3-7}$ cycloalkyl, carboxyl, formyl, acetyl, propanoyl, butyryl, valeryl, pivaloyl, hexanoyl, acetamido, acetate, carbamyl, carboxy, $NH_2$, monoalkylamino, dialkylamino, phenyl, benzyl, phenethyl, napthyl, heterocycle, and keto;

$R^i$, at each occurrence, is selected from F, Cl, Br, I, OH, $NO_2$, CN, $CF_3$, $CF_2CF_3$, $C_{1-4}$ alkyl, $C_{2-6}$ alkenyl, $C_{2-6}$ alkynyl, alkoxy, $C_{3-7}$ cycloalkyl, carboxyl, formyl, acetyl, propanoyl, butyryl, valeryl, pivaloyl, hexanoyl, acetamido, acetate, carbamyl, carboxy, $NH_2$, monoalkylamino, dialkylamino, phenyl, benzyl, and phenethyl;

m is selected from 2, 3, 4, and 5;

n is selected from 0, 1, 2, 3, 4, and 5;

p is selected from 0, 1, and 2;

q is selected from 1, 2, 3, and 4; and r is selected from 0, 1, 2, 3 and 4.

As will be readily understood by the skilled artisan, the position of the double bond in the structure of Formula I will be dependent upon the nature of $R^5$. For example, in certain embodiments wherein $R^5$ is absent, Formula I may have the structure:

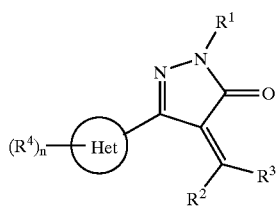

In other embodiments wherein $R^5$ is hydrogen, Formula I may have the tautomeric structure:

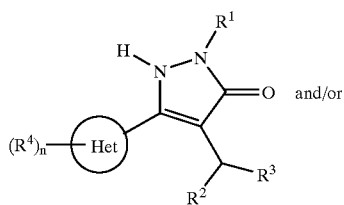

In other embodiments wherein $R^5$ is a substituent, Formula I will have the structure:

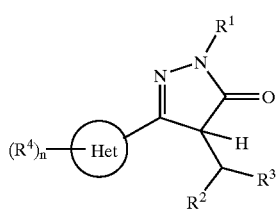

In certain preferred embodiments, Formula I has the formula:

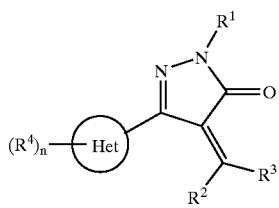

wherein $R^1$ is selected from hydrogen and alkyl. In other preferred embodiments, $R^2$ or $R^3$ is selected from H and alkyl.

In other preferred embodiments, the heterocyclic substituted pyrazolones are represented by the formula:

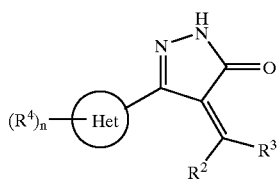

wherein either $R^2$ or $R^3$ is H.

In other preferred embodiments, Het is selected from:
a) a 6-membered heterocyclic ring containing 1 to 3 heteroatoms selected from O, N and S;
b) a 5-membered heterocyclic ring containing either:
1) one oxygen, one nitrogen, or one sulfur atom;
2) a sulfur and a nitrogen atom, an oxygen and a nitrogen atom, or two nitrogen atoms; and
3) three nitrogen atoms, one oxygen and two nitrogen atoms, or one sulfur and two nitrogen atoms;

In other preferred embodiments, Het is heteroaromatic. In other preferred embodiments, Het is selected from:

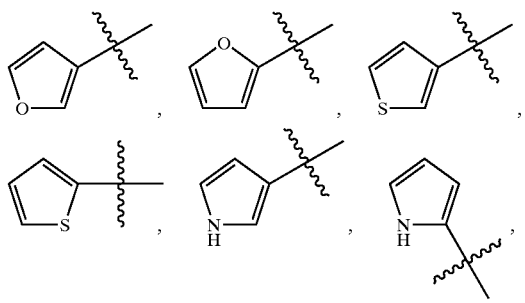

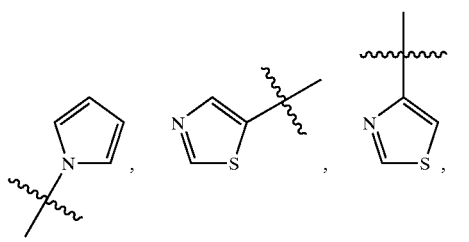

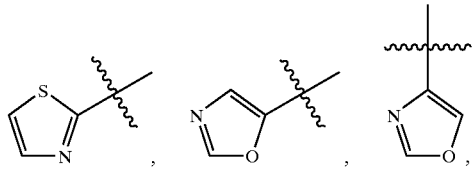

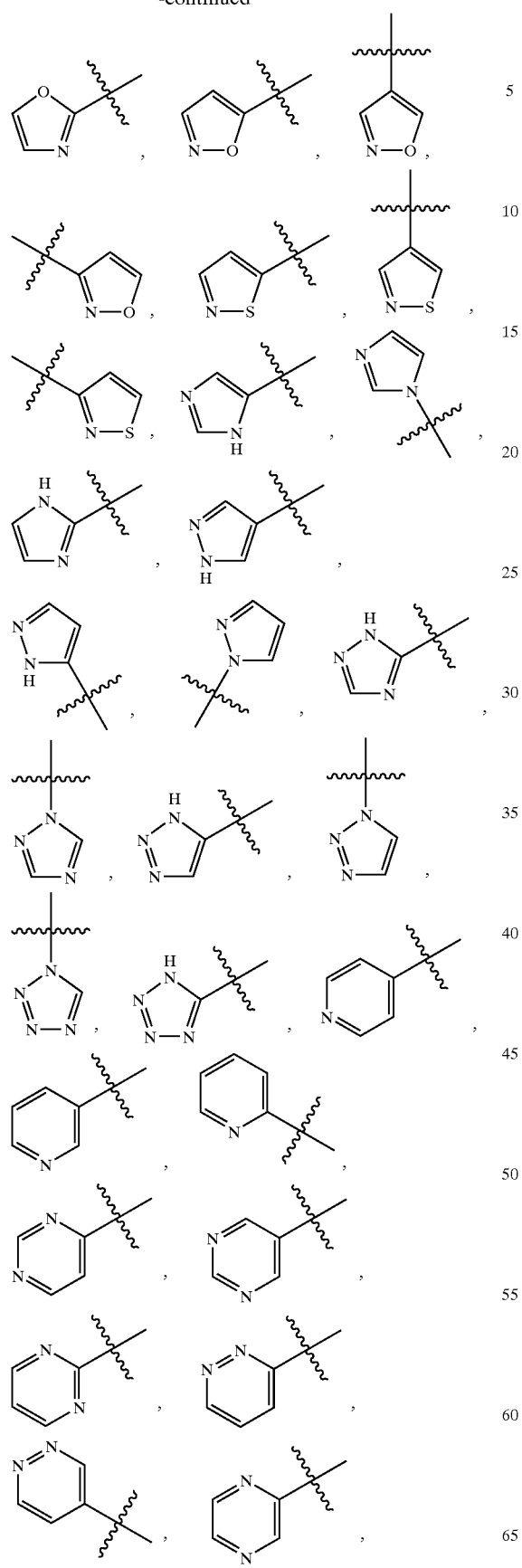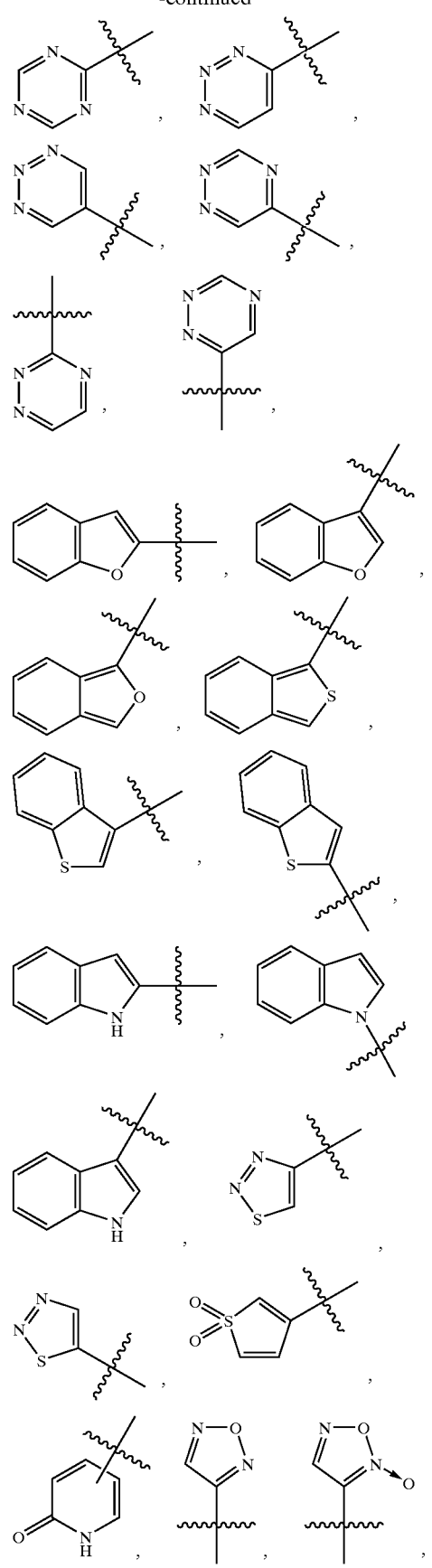

-continued
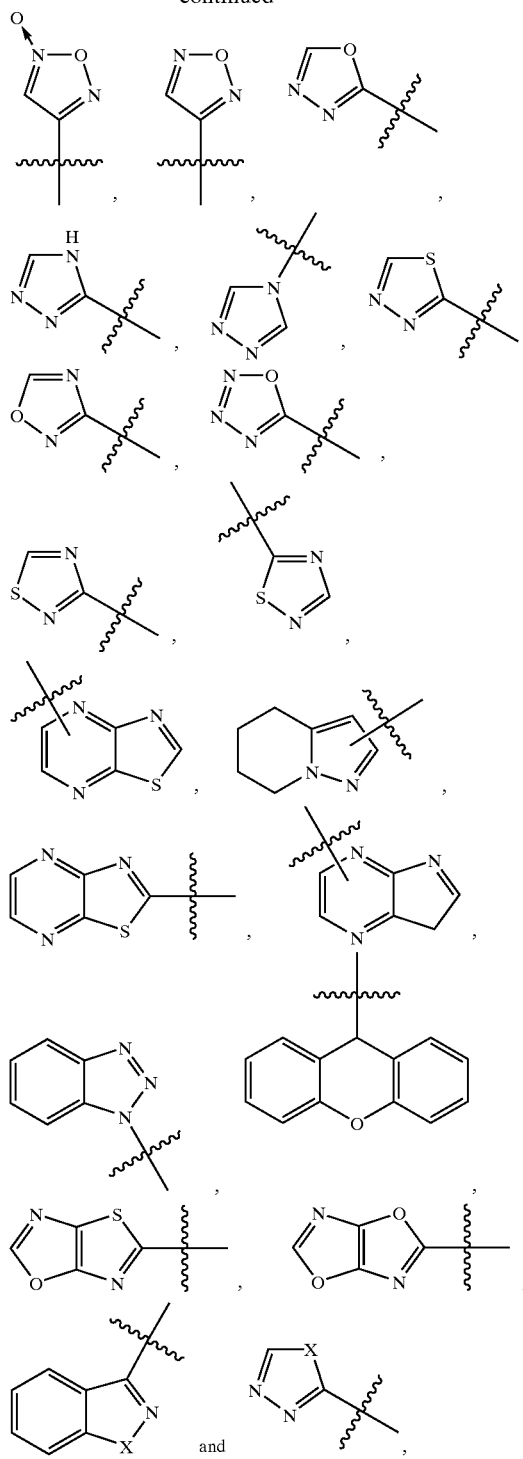
wherein X is selected from O, S, NH and N-alkyl.
In other embodiments, Het is non-aromatic. In certain preferred embodiments, Het is selected from:
-continued
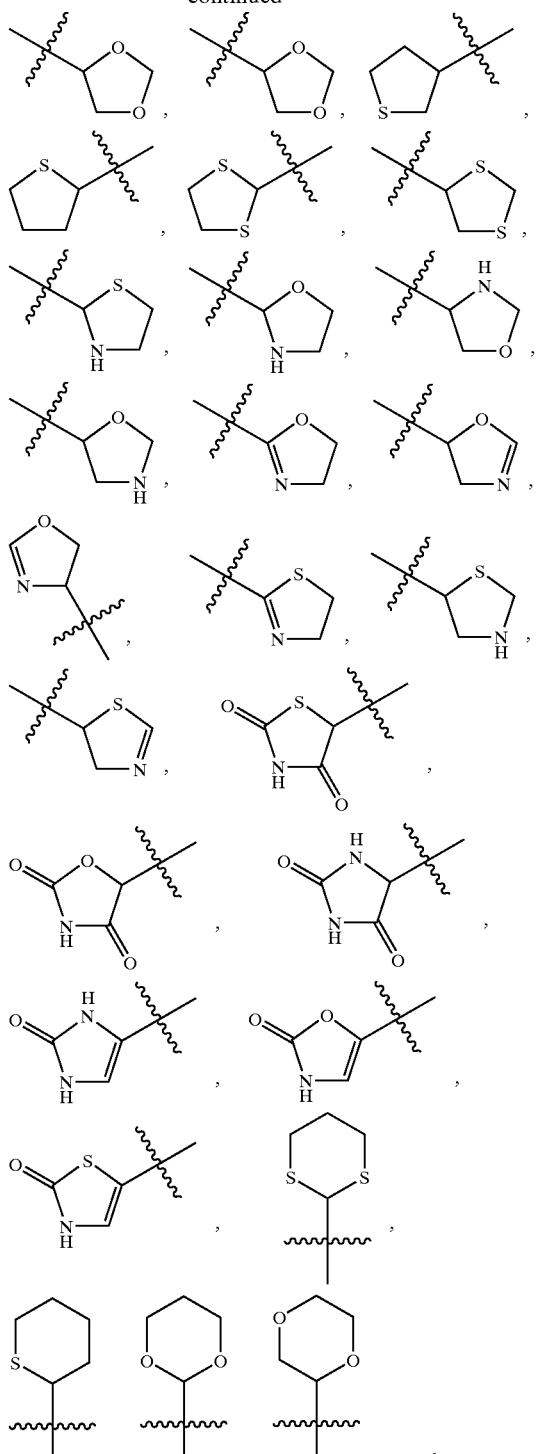
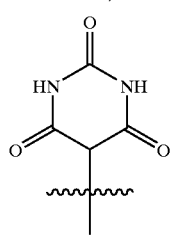
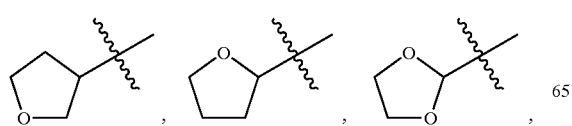

In certain embodiments, $R^4$ is selected from F, Cl, Br, I, OH, $NO_2$, CN, $CF_3$, methyl, ethyl, propyl, iso-propyl, butyl, sec-butyl, t-butyl, pentyl, ethenyl, propenyl, butenyl, ethynyl, propynyl, butynyl, methoxy, ethoxy, n-propoxy, i-propoxy, n-butoxy, s-butoxy, t-butoxy, phenyl, cyclopropyl, cyclobutyl, cyclopentyl, cyclohexyl, $CO_2H$, formyl, acetyl, propanoyl, butyryl, $NH_2$, mono- or di-alkylamino, phenyl, heteroaryl, and keto (C=O). In other preferred embodiments, n is selected from 0, 1, and 2.

In certain embodiments, $R^3$ is a heterocycle selected from:

a) a 6-membered heterocyclic ring containing 1 to 3 heteroatoms selected from O, N and S;
b) a 5-membered heterocyclic ring containing either:
  1) one oxygen, one nitrogen, or one sulfur atom;
  2) a sulfur and a nitrogen atom, an oxygen and a nitrogen atom, or two nitrogen atoms; and
  3) three nitrogen atoms, one oxygen and two nitrogen atoms, or one sulfur and two nitrogen atoms;

In other preferred embodiments, one of $R^2$ or $R^3$ is a heterocycle which is aromatic. In other preferred embodiments, one of $R^2$ or $R^3$ is selected from:

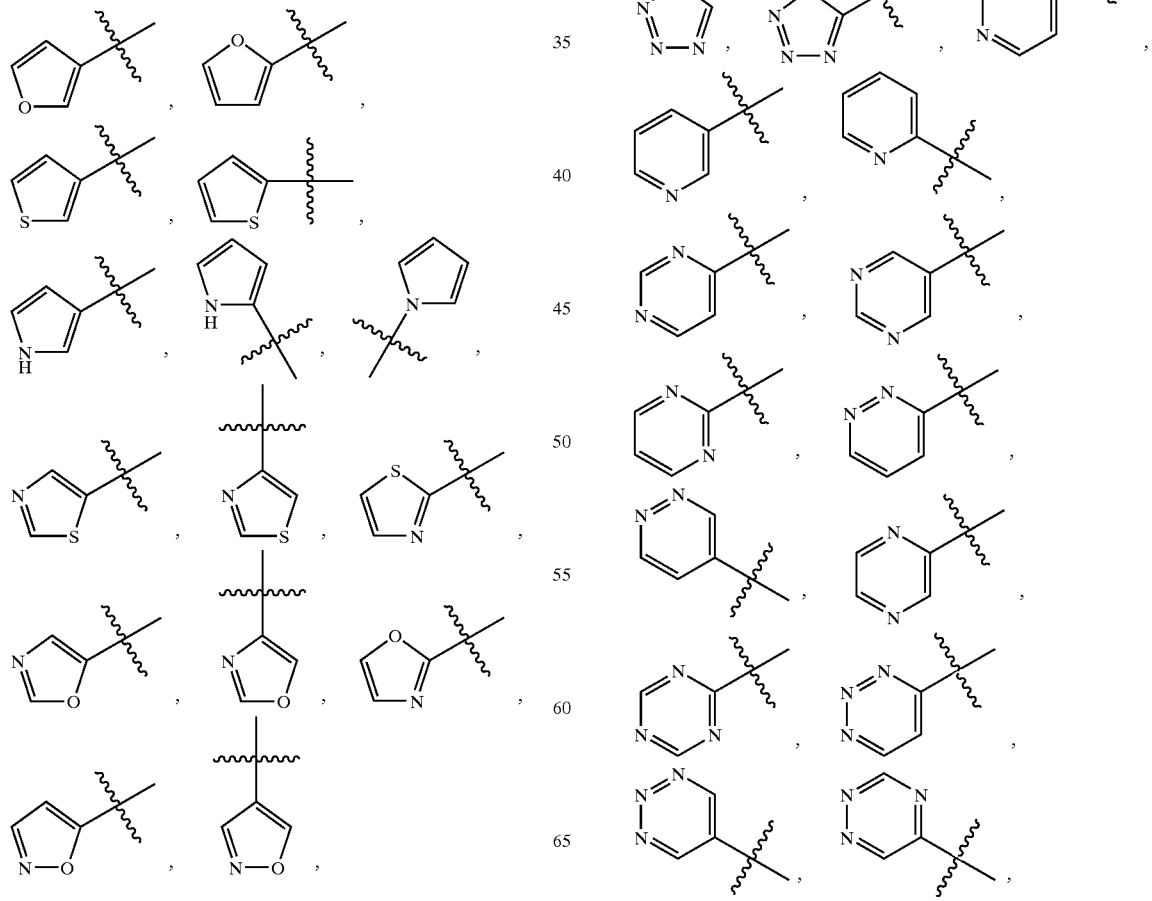

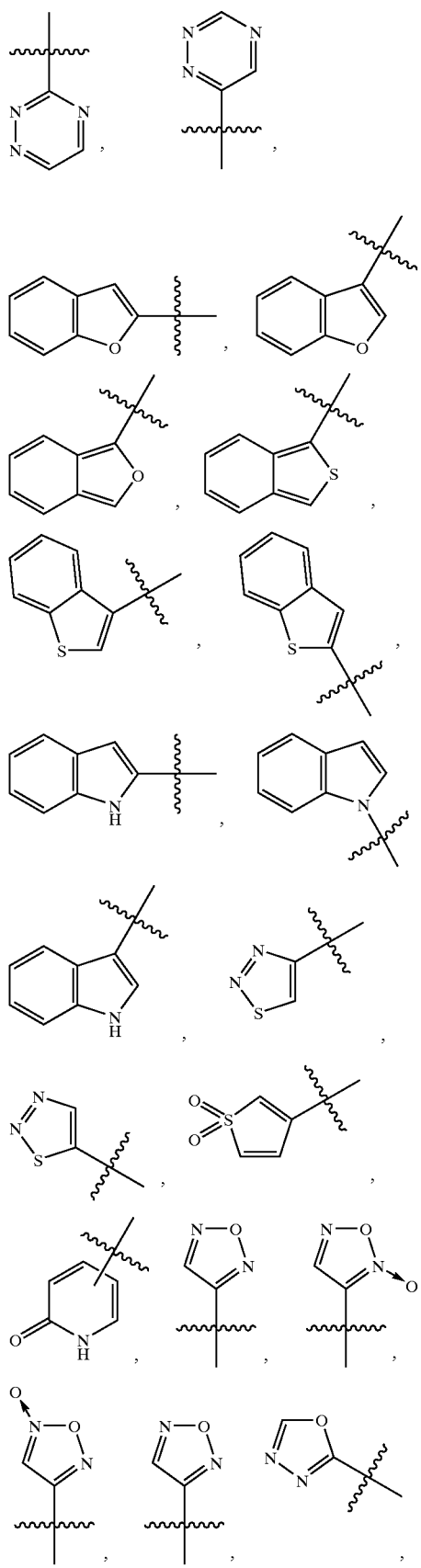
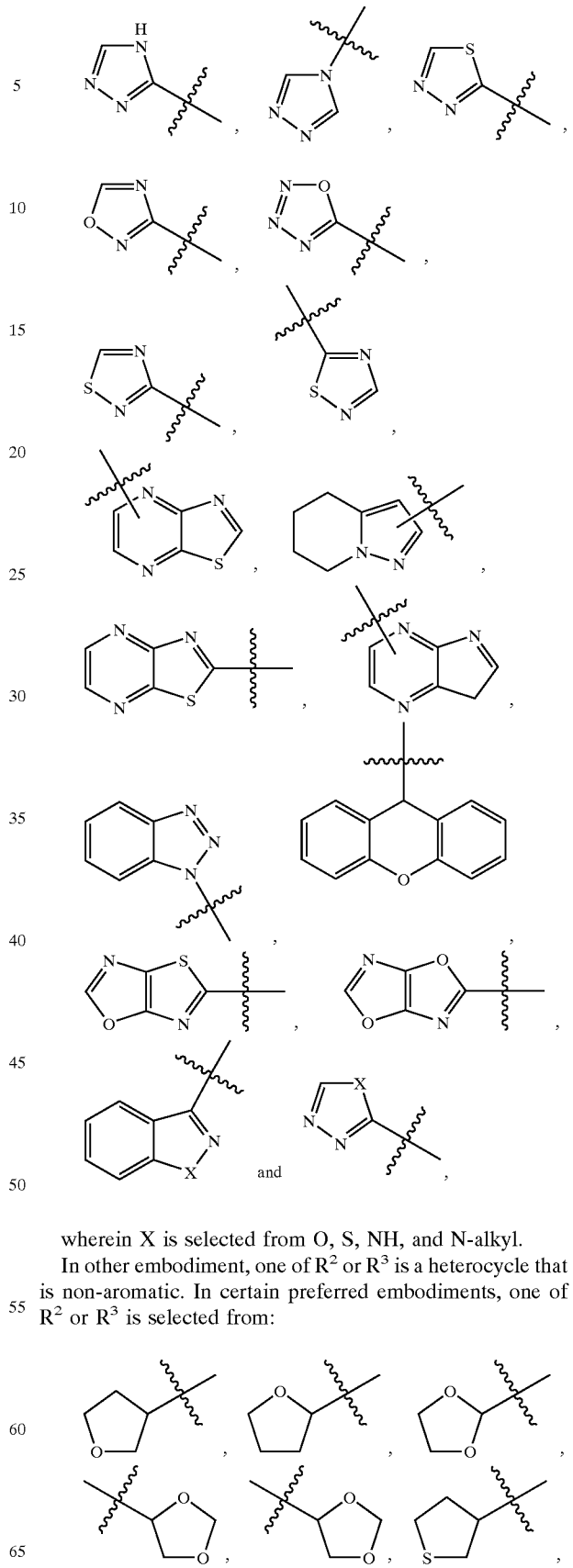
wherein X is selected from O, S, NH, and N-alkyl.
In other embodiment, one of $R^2$ or $R^3$ is a heterocycle that is non-aromatic. In certain preferred embodiments, one of $R^2$ or $R^3$ is selected from:

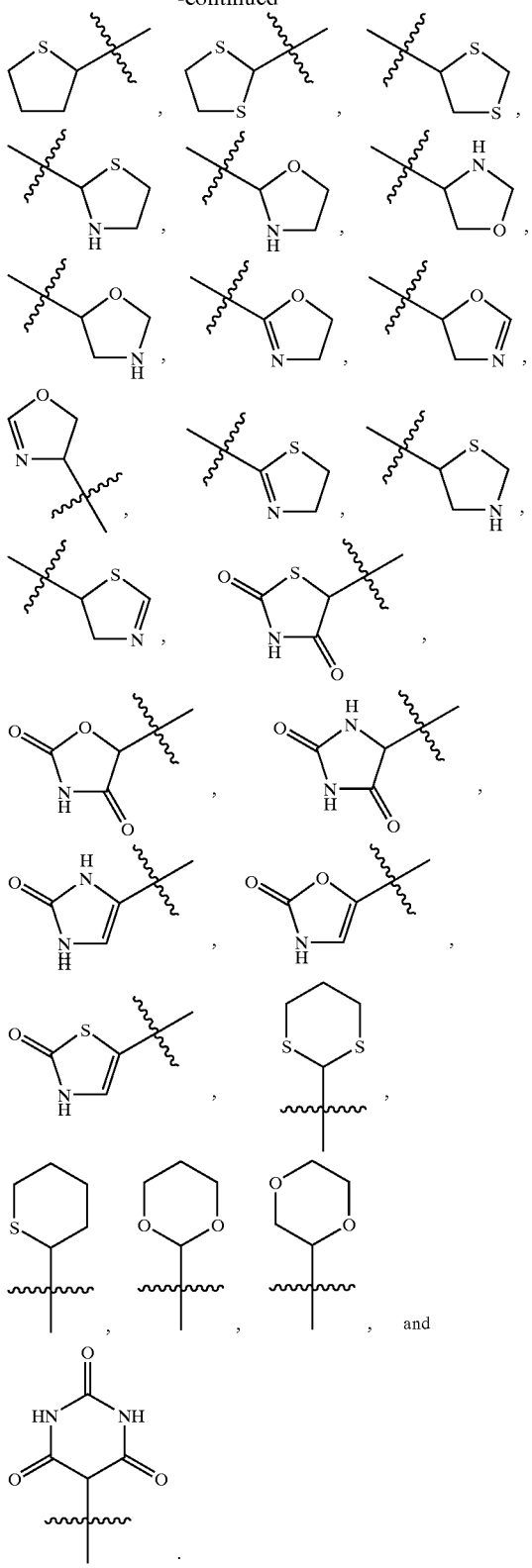

In other embodiments, compounds of Formula I are represented by those set forth in Tables 1 and 1a.

In other embodiments, the present invention provides pharmaceutical compositions comprising a compound of Formula I, a stereoisomer or pharmaceutically acceptable salt thereof, and a pharmaceutically acceptable carrier. In a preferred composition, the compound of Formula I is one set forth in Table 1 or Table 1a.

In other embodiments, the present invention provides a method for inhibiting protein kinase activity comprising providing a compound of Formula I in an amount sufficient to result in effective inhibition. In a preferred embodiment, the kinase receptor is vascular endothelial growth factor receptor (VEGFR) kinase, trkA tyrosine kinase (trkA), mixed lineage kinase (MLK) or fibroplast growth factor receptor kinase (FGFR).

In other embodiments, the present invention provides a method for treating or preventing disorders characterized by the aberrant activity of a protein kinase which comprises administering to a host in need of such treatment or prevention a therapeutically effective amount of a compound of Formula I.

In other embodiments, the present invention provides a method for treating or preventing disorders where either the vascular endothelial growth factor receptor (VEGFR) kinase, trkA tyrosine kinase (trkA), mixed lineage kinase (MLK) or the fibroplast growth factor receptor kinase (FGFR) contributes to pathological conditions, the method comprising providing a compound of Formula I in an amount sufficient to result in the receptor being contacted with an effective inhibitory amount of the compound.

In another embodiment, the present invention provides a method for treating or preventing angiogenic disorders which comprises administering to a host in need of such treatment or prevention a therapeutically effective amount of a compound of Formula I. In a preferred embodiment, the angiogenic disorder is cancer of solid tumors, ocular disorders, macular degeneration, endometriosis, diabetic retinopathy, psoriasis, or hemangioblastoma.

In another embodiment, the present invention provides a method of treating or preventing a disease mediated by a kinase selected from ab1, AKT, bcr-ab1, Blk, Brk, Btk, c-kit, c-met, c-src, CDK1, CDK2, CDK4, CDK6, chk1, chk2, cRaf1, CSF1R, CSK, EGFR, ErbB2, ErbB3, ErbB4, ERK (Eph), Fak, fes, FGFR1, FGFR2, FGFR3, FGFR4, FGFR5, Fgr, FLK-4, flt-1, Fps, Frk, Fyn, GSK, Hck, IGF-1R, INS-R, Jak, JNK, VEGFR1, VEGFR2, VEGFR3, Lck, Lyn, MEK, p38, PDGFR, PIK, PKC, PYK2, ros, $tie_1$, $tie_2$, TRK, UL97, Yes and Zap70, the method comprising administering to a patient in need of such treatment or prevention a pharmaceutically effective amount of a compound of Formula I.

In other embodiments, the present invention provides a method for treating or preventing disorders where a kinase selected from ab1, AKT, bcr-ab1, Blk, Brk, Btk, c-kit, c-met, c-src, CDK1, CDK2, CDK4, CDK6, chk1, chk2, cRaf1, CSF1R, CSK, EGFR, ErbB2, ErbB3, ErbB4, ERK (Eph), Fak, fes, FGFR1, FGFR2, FGFR3, FGFR4, FGFR5, Fgr, FLK-4, flt-1, Fps, Frk, Fyn, GSK, Hck, IGF-1R, INS-R, Jak, JNK, VEGFR1, VEGFR2, VEGFR3, Lck, Lyn, MEK, p38, PDGFR, PIK, PKC, PYK2, ros, $tie_1$, $tie_2$, TRK, UL97, Yes and Zap70 contributes to pathological conditions, the method comprising providing a compound of Formula I in an amount sufficient to result in the receptor being contacted with an effective inhibitory amount of the compound.

In another embodiment, the present invention provides a method for treating or preventing Alzheimer's disease, amyotrophic lateral sclerosis, Parkinson's disease, stroke, ischaemia, Huntington's disease, AIDS dementia, epilepsy, multiple sclerosis, peripheral neuropathy, injuries of the brain or spinal chord, cancer, restenosis, osteoporosis, inflammation, angiogenesis, viral infections, bone or hematopoetic diseases, autoimmune diseases or transplant rejection which comprises administering to a host in need of such treatment or prevention a therapeutically effective amount of a compound of Formula I.

In certain embodiments, the present invention is directed to inhibition of one or more of Src, raf, and the cyclin-dependent kinases (CDK) 1, 2, and 4 for the treatment of cancer.

In certain embodiments, the present invention is directed to inhibition of one or more of CDK2 or PDGF-R kinase for the treatment of restenosis.

In certain embodiments, the present invention is directed to inhibition of one or more of CDK5 or GSK3 kinases for the treatment of Alzheimers.

In certain embodiments, the present invention is directed to inhibition of one or more of c-Src kinase for the treatment of osteoporosis.

In certain embodiments, the present invention is directed to inhibition of one or more of GSK-3 kinase for the treatment of type-2 diabetes.

In certain embodiments, the present invention is directed to inhibition of one or more of p38 kinase for the treatment of inflammation.

In certain embodiments, the present invention is directed to inhibition of one or more of VEGF-R 1-3, TIE-1, or TIE-2 kinases for the treatment of angiogenesis.

In certain embodiments, the present invention is directed to inhibition of one or more of UL97 kinase for the treatment of viral infections.

In certain embodiments, the present invention is directed to inhibition of one or more of CSF-1R kinase for the treatment of bone and hematopoetic diseases.

In certain embodiments, the present invention is directed to inhibition of one or more of and Lck kinase for the treatment autoimmune diseases and transplant rejection.

In certain embodiment, the present invention provides a method of treating or preventing a disorders mediated by topoisomerases Topo-I or Topo II for the treatment of cancer.

Definitions

The following terms and expressions have the indicated meanings. As used herein "stable compound" or "stable structure" is meant to indicate a compound that is sufficiently robust to survive isolation to a useful degree of purity from a reaction mixture, and preferably capable of formulation into an efficacious therapeutic agent. The present invention is directed only to stable compounds. As used herein, "substituted" is intended to indicate that one or more hydrogen atoms on an indicated group is replaced with a selected group referred to herein as a "substituent", provided that the substituted atom's valency is not exceeded, and that the substitution results in a stable compound. When the term "substituted" preceeds a group containing $(CH_2)_r$ or $(CH_2)_q$, for example, $(CH_2)_r$phenyl, it is intended that the substituent may reside on the group, i.e., phenyl, or the $CH_2$ chain. By way of illustration, groups which may be further substituted include, but are not limited to, alkyl, alkenyl, alkynyl, alkoxy, acyl, carbocyclic, and heterocyclic, along with additional groups which contain these moieties. A substituted group preferably has 1 to 5 independently selected substituents. Preferred substituents include, but are not limited to F, Cl, Br, I, OH $NO_2$, CN, $CF_3$, $CF_2CF_3$, alkyl including, but not limited to, methyl, ethyl, propyl, isopropyl, butyl, sec-butyl, tert-butyl, and pentyl; alkenyl including but not limited to, ethenyl, propenyl, and butenyl; alkynyl including, but not limited to, ethynyl, propynyl, and butynyl; alkoxy including, but not limited to, methoxy, ethoxy, n-propoxy, i-propoxy, n-butoxy, s-butoxy, and t-butyloxy; cycloalkyl including, but not limited to, cyclopropyl, cyclobutyl, cyclopentyl, and cyclohexyl; carboxyl, acyl including, but not limited to, formyl, acetyl, propanoyl, butyryl, valeryl, pivaloyl, and hexanoyl; acetamido, carbamyl, carboxy, hydroxamino, $NH_2$, monoalkylamino, dialkylamino, $(CH_2)_r$carbocycle including, but not limited to, phenyl, phenyl, benzyl, phenethyl, and napthyl; heterocycle, and keto (=O).

As used herein, the term "alkyl" means a straight-chain, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, hexyl, octyl. As used herein, "cycloalkyl" is intended mean monocyclic, bicyclic or tricyclic alkyl groups including, but not limited to cyclopropyl, cyclobutyl, cyclopentyl, cyclohexyl, and the like.

As used herein, "alkenyl" is intended to include hydrocarbon chains of either a straight or branched configuration and one or more unsaturated carbon-carbon bonds which may occur in any stable point along the chain, such as ethenyl, propenyl and the like.

As used herein, "alkynyl" is intended to include hydrocarbon chains of either a straight or branched configuration and one or more triple carbon-carbon bonds which may occur in any stable point along the chain, such as ethynyl, propynyl, and the like.

As used herein, "alkoxy" is intended to include hydrocarbon chains of either straight or branched configuration bonded through an oxygen. Alkoxy includes, but is not limited to methoxy, ethoxy, n-propoxy, i-propoxy, n-butoxy, s-butoxy, t-butyloxy, and the like.

As used herein, "carbocycle" is intended to mean any stable monocyclic, bicyclic or tricyclic ring made up on carbon atoms, which may be saturated, partially unsaturated, or unsaturated. Carbocycles are intended to include, but are not limited to, compounds referred to herein as "cycloalkyl". Carbocycles are also intended to include "aryl" or "aromatic" compounds. Examples of aryl compounds include, but are not limited to phenyl, biphenyl, naphthyl, indanyl, adamantyl, or tetrahydronaphthyl (tetralin).

As used herein, the term "heterocycle" or "heterocyclic ring" is intended to include a stable monocyclic, bicyclic or tricyclic heterocyclic ring which is saturated, partially unsaturated, or unsaturated rings. Accordingly, heterocycles may be aromatic or non-aromatic. Heterocycles preferably consist of carbon atoms and heteroatoms which are preferably independently selected from the group consisting of N, O and S. The nitrogen and sulfur heteroatoms may optionally be oxidized. The heterocyclic ring may be attached to its pendant group at any heteroatom or carbon atom which results in a stable structure. The heterocycles described herein may be substituted on, for example, a carbon or a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

As used herein, the term "heteroaromatic" or "heteroaryl" is intended to mean a stable heterocycle which is aromatic and consists of carbon atoms and heteroatoms, wherein the heteroatoms are preferably independently selected from the group consisting of N, O and S.

Examples of heterocycles include, but are not limited to, 2-pyrrolidonyl, 2H-pyrrolyl, 4-piperidonyl, 6H-1,2,5-thiadiazinyl, 2H,6H-1,5,2-dithiazinyl, furanyl, furazanyl, imidazolidinyl, imidazolinyl, imidazolyl, isoxazolyl, morpholinyl, oxadiazolyl, 1,2,3-oxadiazolyl, 1,2,4- oxadiazolyl, 1,2,5-oxadiazolyl, 1,3,4-oxadiazolyl, oxazolidinyl, oxazolyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, tetrahydrofuranyl, 6H-1,2,5-thiadiazinyl, 1,2,3-thiadiazolyl, 1,2,4-thiadiazolyl, 1,2,5-thiadiazolyl, 1,3,4-thiadiazolyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and tetrazole. Also included are fused ring and spiro compounds containing, for example, the above heterocycles. Suitable heterocycles are also disclosed in *The Handbook of Chemistry and Physics*, 76th Edition, CRC Press, Inc., 1995–1996, pages 2–25 to 2–26, the disclosure of which is hereby incorporated by reference.

Preferred heterocyclic groups formed with a nitrogen atom include, but are not limited to, pyrrolidinyl, piperidinyl, piperidino, morpholinyl, morpholino, thiomorpholino, N-methylpiperazinyl, indolyl, isoindolyl, imidazole, imidazoline, oxazoline, oxazole, triazole, thiazoline, thiazole, isothiazole, thiadiazoles, triazines, isoxazole, oxindole, indoxyl, pyrazole, pyrazolone, pyrimidine, pyrazine, quinoline, iosquinoline, and tetrazole groups.

Preferred heterocyclic groups formed with an oxygen atom include, but are not limited to, furan, tetrahydrofuran, pyran, benzofurans, isobenzofurans, and tetrahydropyran groups. Preferred heterocyclic groups formed with a sulfur atom include, but are not limited to, thiophene, thianaphthene, tetrahydrothiophene, tetrahydrothiapyran, and benzothiophenes.

Preferred heteroaryl groups include, but are not limited to, pyridyl, pyrimidyl, pyrrolyl, furyl, thienyl, imidazolyl, triazolyl, tetrazolyl, quinolyl, isoquinolyl, benzoimidazolyl, thiazolyl, pyrazolyl, and benzothiazolyl groups.

As used herein, the term "monosaccharide" has its accustomed meaning as a simple sugar. As used herein, the term "amino acid" denotes a molecule containing both an amino group and a carboxyl group. Embodiments of amino acids include α-amino, β-amino, γ-amino acids. As used herein, "α-amino acids" are carboxylic acids of general formula HOOC—CH(NH$_2$)-(side chain). Side chains of amino acids include naturally occurring and non-naturally occurring moieties. Non-naturally occurring (i.e., unnatural) amino acid side chains are moieties that are used in place of naturally occurring amino acid side chains in, for example, amino acid analogs. See, for example, Lehninger, Biochemistry, Second Edition, Worth Publishers, Inc, 1975, pages 73–75, the disclosure of which is incorporated herein by reference. In certain embodiments, substituent groups of formula $R^d$ include the residue of an amino acid after removal of the hydroxyl moiety of the carboxyl group thereof; i.e., groups of Formula —C(=O)CH-(side chain)-NHR', wherein R' is H, $C_{1-6}$ alkyl, or an amine protecting group. In certain embodiments, substituent groups of formula $R^{d'}$ include the residue of an amino acid after removal of the hydrogen of the amine group thereof; i.e., groups of Formula —NH—CH-(side chain)-C(=O)OR', wherein R' is H, $C_{1-6}$ alkyl, or a carboxyl protecting group.

Functional groups present on the compounds of Formula I or intermediate compounds may also contain protecting groups. Preferred protecting groups include the benzyloxycarbonyl (Cbz; Z) group and the tert-butyloxycarbonyl (Boc) group. Other preferred protecting groups may be found in Greene, T. W. and Wuts, P. G. M., *Protective Groups in Organic Synthesis* 2d. Ed., Wiley & Sons, 1991, a common text in the field, the disclosure of which is incorporated herein by reference.

As used herein, terms commonly used to describe the effects of therapeutic agents in biological systems, assays, and the like, are intended to have their art-recognized meanings. As used herein, the term "effect" when used to modify the terms "function" and "survival" means a positive or negative alteration or change. An effect which is positive may be referred to herein as an "enhancement" or "enhancing", and an effect which is negative may be referred to herein as "inhibition" or "inhibiting."

As used herein, the terms "enhance" or "enhancing" when used to modify the terms "function" or "survival" means that the presence of an heterocyclic substituted pyrazolone compound has a positive effect on the function and/or survival of a trophic factor responsive cell compared with a cell in the absence of the compound. For example, and without limitation, with respect to the survival of, e.g., a cholinergic neuron, the compound would evidence enhancement of survival of a cholinergic neuronal population at risk of dying (due to, e.g., injury, a disease condition, a degenerative condition or natural progression) when compared to a cholinergic neuronal population not presented with such compound, if the treated population has a comparatively greater period of functionality than the non-treated population. As used herein, "inhibit" and "inhibition" mean that a specified response of a designated material (e.g., enzymatic activity) is comparatively decreased in the presence of a heterocyclic substituted pyrazolone compound.

As used herein, the term "trk" refers to the family of high affinity neurotrophin receptors presently comprising trk A, trk B, and trk C, and other membrane associated proteins to which a neurotrophin can bind.

As used herein, the terms "cancer" and "cancerous" refer to any malignant proliferation of cells in a mammal. Examples include prostate, benign prostate hyperplasia, ovarian, breast, brain, lung, pancreatic, colorectal, gastric, stomach, solid tumors, head and neck, neuroblastoma, renal cell carcinoma, lymphoma, leukemia, other recognized malignancies of the hematopoietic systems, and other recognized cancers.

As used herein the terms "neuron," "cell of neuronal lineage" and "neuronal cell" include, but are not limited to, a heterogeneous population of neuronal types having singular or multiple transmitters and/or singular or multiple functions; preferably, these are cholinergic and sensory neurons. As used herein, the phrase "cholinergic neuron" means neurons of the Central Nervous System (CNS) and Peripheral Nervous System (PNS) whose neurotransmitter is acetylcholine; exemplary are basal forebrain, striatal, and spinal cord neurons. As used herein, the phrase "sensory neuron" includes neurons responsive to environmental cues (e.g., temperature, movement) from, e.g., skin, muscle and joints; exemplary is a neuron from the dorsal root ganglion.

As used herein, a "trophic factor-responsive cell," is a cell which includes a receptor to which a trophic factor can specifically bind; examples include neurons (e.g., cholinergic and sensory neurons) and non-neuronal cells (e.g., monocytes and neoplastic cells).

As used herein, a "therapeutically effective amount" refers to an amount of a compound of the present invention effective to prevent or treat the symptoms of particular disorder. Such disorders include, but are not limited to, those pathological and neurological disorders associated with the aberrant activity of the receptors described herein, wherein the treatment or prevention comprises inhibiting, inducing, or enhancing the activity thereof by contacting the receptor with a compound of Formula I.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ration.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

As used herein, "prodrug" is intended to include any covalently bonded carriers which release the active parent drug according to Formula (I) or other formulas or compounds of the present invention in vivo when such prodrug is administered to a mammalian subject. Since prodrugs are known to enhance numerous desirable qualities of pharmaceuticals (e.g., solubility, bioavailability, manufacturing, etc.) the compounds of the present invention may be delivered in prodrug form. Thus, the present invention contemplates prodrugs of the claimed compounds, compositions containing the same, and methods of delivering the same.

Prodrugs of a compound of the present invention, for example Formula I, may be prepared by modifying functional groups present in the compound in such a way that the modifications are cleaved, either in routine manipulation or in vivo, to the parent compound. Accordingly, prodrugs include, for example, compounds of the present invention wherein a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

Synthesis

The compounds of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multi-kilogram or commercial industrial scale.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, re-crystallization, and the like, or by chiral synthesis either from chiral starting materials or by deliberate generation of target chiral centers.

As will be readily understood, functional groups present on the compounds of Formula I may contain protecting groups during the course of synthesis. For example, the amino acid side chain substituents of the compounds of Formula I can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl (Cbz; Z) group and the tert-butyloxycarbonyl (Boc) group. Other preferred protecting groups according to the invention may be found in Greene, T. W. and Wuts, P. G. M., *Protective Groups in Organic Synthesis* 2d. Ed., Wiley & Sons, 1991.

Compounds having formula (I-i) or (I-ii):

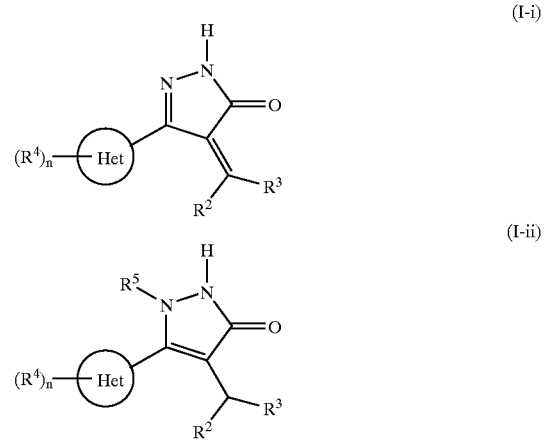

may be prepared, for example, as described in Schemes 1 through 6. For certain embodiments, the β-ketoester (V) serves as a key intermediate to I-i and I-ii.

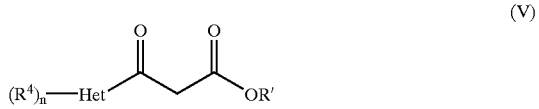

(V)

In certain embodiments, compounds of the present invention may contain heterocycles, which are further substituted. Heterocyclic compounds which are further substituted (including additional heterocycles) may be obtained by a variety of methods known to those skilled in the art. Starting materials as well as methods which may be used for the synthesis of β-ketoester intermediate (V) are described, for example, by Thompson and Gaudino, *J. Org. Chem.* 1984, 49, 5237–5243; an d by Kamal M. R. et. al., *Phosphorous, Sulfur, Silicon Relat. Elem.* 1997, 126, 65–74; the disclosures of which are incorporated herein by reference in their entirety.

Generally, compounds of formula (V) may be prepared, for example, by methods set forth in Scheme 1.

may be added dropwise a solution of the desired heterocyclic methyl ketone (II) (1 equiv.) in toluene under reflux. After addition, the mixture may be stirred at reflux for approximately 0.5 hour. The mixture is preferably cooled to room temperature and acidified with a suitable acid, such as glacial acetic acid. After addition of cold water, the mixture may be extracted from a suitable solvent, such as toluene. After work up, the solvent may be evaporated to furnish the crude β-ketoester, (V), which may be used for pyrazolone formation without further purification.

Intermediate (V) may also be obtained from a heterocyclic compound (IV) following metalation and reaction with ethyl propinyl chloride (Scheme 1c). This method is further described by Morales-Rios, et. al, *Heterocycles*, 1996, 43, 1483–96, the disclosure of which is incorporated herein by reference in its entirety.

The β-ketoester (V), prepared by any of the foregoing methods may be reacted, for example, with various hydrazine derivatives (Scheme 2).

Scheme 1:

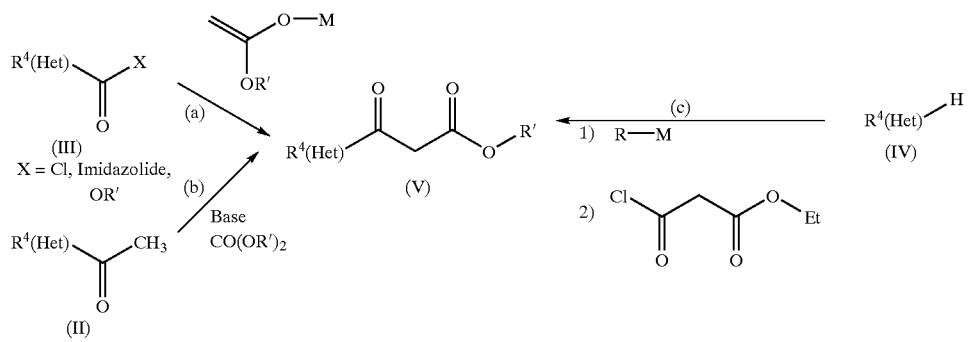

Reaction of a heterocyclic methyl ester, acid halide or imidazolide (III), with an ester enolate, affords compound (V) (Scheme 1a). Similar methods are taught, for example, in Bunting, J. W.; Kanter, J. P., *J. Am. Chem. Soc.*, 1993, 115, 11705–11715, the disclosure of which is incorporated herein by reference in its entirety. By way of further guidance, to a solution of heterocyclic carboxylic ester (III) (1 equiv.) in methyl acetate (0.5–1 mL/mmol of the ester) may be added NaH (60% dispersion in mineral oil, 1.1 equiv.) with continuous stirring for approximately 0.5 hours. The reaction mixture is preferably stirred under reflux for about 2.5 hours, cooled to room temperature, poured to water (1 ml/mmol of the ester), and extracted from a suitable solvent such as diethyl ether. The aqueous layer may be neutralized with concentrated acid and extracted repeatedly with a polar solvent such as methylene chloride. The combined organic layers are preferably combined and concentrated in vacuo to provide the crude β-ketoester (V), which may be used for pyrazolone formation without further purification.

Alternatively, compounds of formula (V) may be prepared by carboxy-alkylation of a heterocyclic methyl ketone, using a dialkyl carbonate (Scheme 1b). The synthesis of β-ketoesters prepared in this manner are also described, for example, in Krapcho, A. P.; Diamanti, J.; Cayen, C.; Bingham, R., *Org. Synth.* 1973, 5, 198–201, the disclosure of which is incorporated herein by reference in its entirety. By way of further guidance, to a vigorously stirred suspension of NaH (2.9 equiv.) and diethyl carbonate (2 equiv.) in dry toluene (1.5 mL/mmol of the methyl ketone)

Scheme 2:

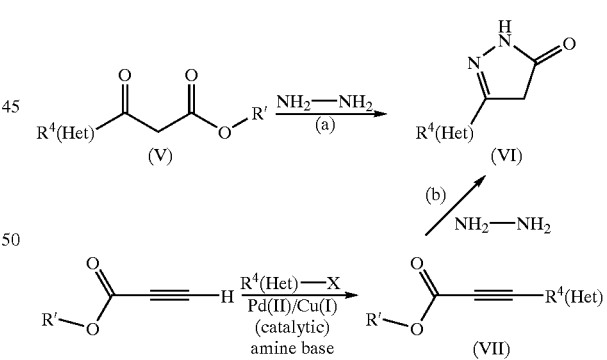

Reaction with hydrazine provides 4-unsubstituted pyrazolones (VI) (Scheme 2a). By way of further guidance, to a mixture of β-ketoester (V) in absolute ethanol (3–5 mL/mmol of β-ketoester) may be added hydrazine hydrate (5–10-fold excess) and the mixture kept under reflux for approximately 3–5 hours. The mixture is preferably cooled to room temperature and the solvent was evaporated. The pyrazolone may be isolated by filtration (if solid separation was noticed) or flash chromatography using an appropriate chromatographic solvent system such as EtOAc/methanol. Subsequent tituration with ether or ethyl acetate may help aid in further purification. The 4-unsubstituted pyrazolones (VI) may also be obtained by reaction of a heterocylic propargyl ester (VII) with excess hydrazine (Scheme 2b).

Upon Knoevenagel condensation with appropriately substituted carbonyl compounds, the pyrazolone (VI) provides the desired pyrazolone analogs (I-i) (Scheme 3).

Scheme 3:

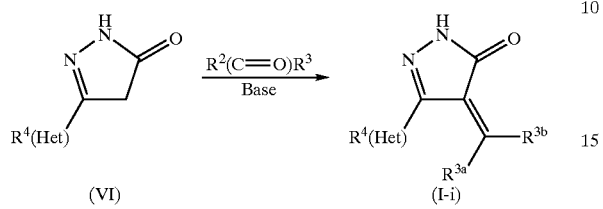

By way of further guidance, a mixture of the appropriate pyrazolone (1 equiv.) and the desired aldehyde (1.1 equiv.) in absolute ethanol (2.5–3 mL/mmol of pyrazolone) may be stirred at 80–90° C. for approximately 1 to 5 hours. The product that separates as a solid (either from hot reaction mixture or upon subsequent cooling in ice bath) may be isolated by filtration and washed with small amounts of a protic solvent such as ethanol. NMR of the solid preferably shows one geometrical isomer. Other methods are taught, for example, in the text *Organic Synthesis*, G. Jones, edited by R. Adams, John Wiley & Sons, INC., New York, 1967, pp 204–599, the disclosure of which is incorporated herein by reference in its entirety.

Alternatively, the β-ketoester (V) may be first condensed with an appropriately substituted carbonyl compound to provide intermediate (VIII), which may be subsequently converted to the pyrazolone (I-i) (Scheme 4).

Scheme 4:

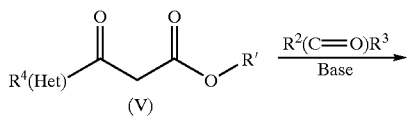

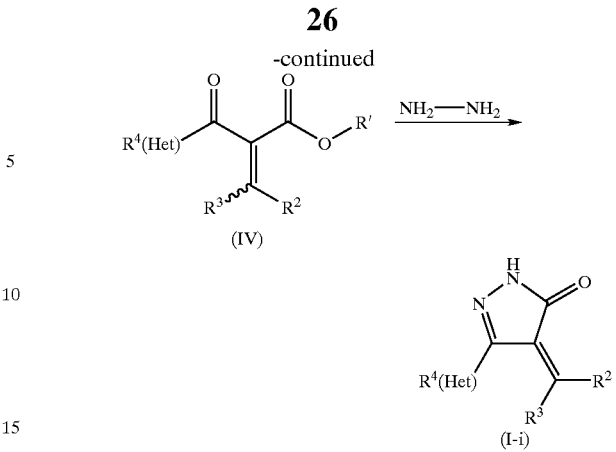

The pyrazolone derivative bearing the $R^5$ substituents may be obtained by the reaction of mono-substituted hydrazine (or disubstituted hydrazine, e.g. when $R^1$ not hydrogen is desired) either with a β-ketoester (V) or the acetylenic derivative (VII) (Schemes 5a and 5b, respectively). The substituent at the 4 position may then be introduced, for example, with an aldehyde and a secondary amine (Scheme 5c). Compounds wherein $R^2$ is a heterocycle attached through a heteroatom may be prepared, for example, by reacting compound (XI) with formaldehyde in the presence of a nucleophilic heterocycle (Scheme 5d).

Scheme 5:

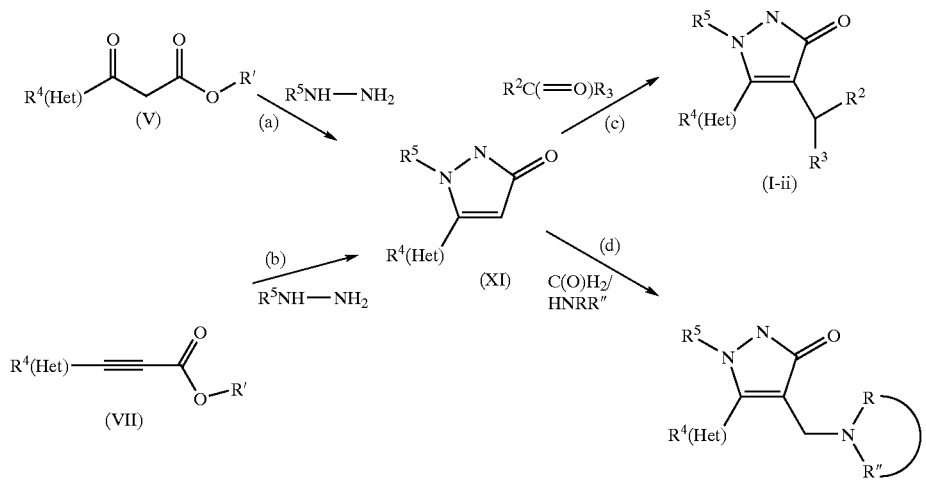

Alternatively, the β-ketoester (X), already bearing a substituent, may be subsequently converted to the pyrazolone analogs (I-ii). Compound (X) may be prepared, for example, by reaction of a heterocyclic methyl ester, acid halide or imidazolide (III), with an appropriately substituted ester enolate (Scheme 6a). Alternatively, compound (X) may be prepared by deprotonating a heterocyclic β-ketoester and reacting the enolate with an appropriately substituted alkyl halide, alkyl mesylate, or the like (Scheme 6b).

Scheme 6:

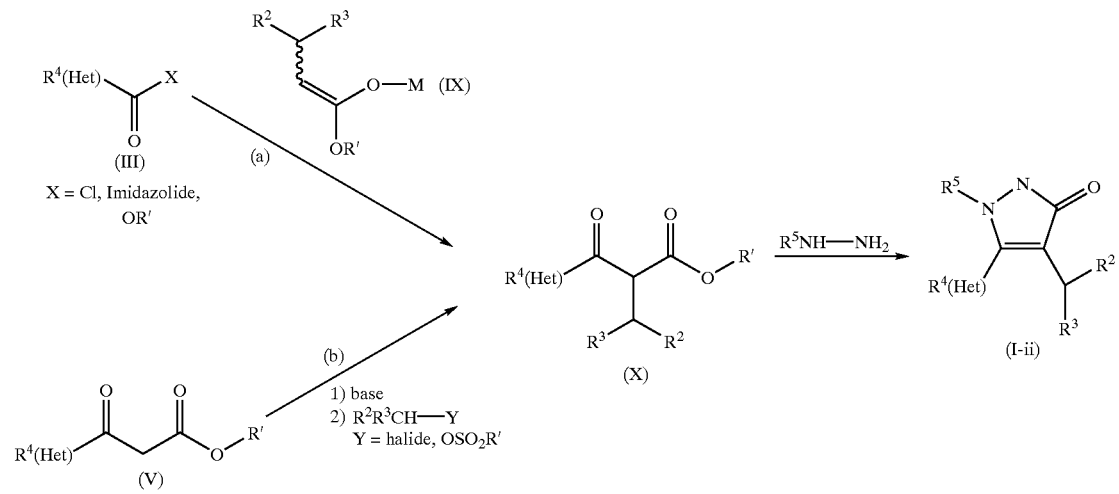

Compounds of Formula (I-ii) and/or (I-iii) may also be prepared, for example, from pyrazolone (I-i), upon treatment with an appropriate reducing agent, such as $NaBH_4$, $LiBH_4$, and the like (Scheme 7). As will be appreciated by one skilled in the art, compounds of Formula (I-ii) or (I-iii) may be further reacted under suitable conditions to add $R^5$ groups, wherein $R^5$ is other than hydrogen.

Scheme 7:

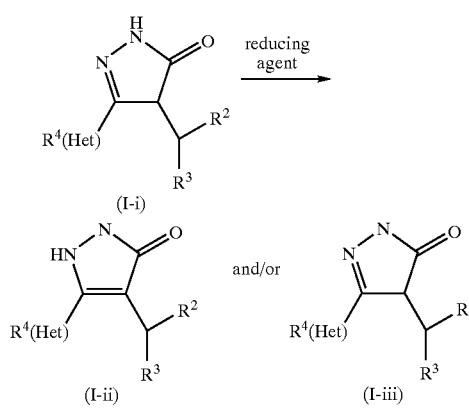

Other features of the invention will become apparent in the course of the following descriptions of exemplary embodiments. These examples are given for illustration of the invention and are not intended to be limiting thereof

EXAMPLES

Certain abbreviations used herein are defined as follows: "EtOAc" for ethyl acetate, "MeOH" for methanol, "EtOH" for ethanol, "DMSO-$d_6$" for deuterated dimethylsulfoxide, "rt" for room temperature, "d" for doublet, "dd" for doublet of doublets, "t" for triplet, "m" for multiplet, "J" for coupling constant, "br" for broad, "eq" or "equiv" for equivalents, "g" for gram or grams, "mg" for milligram or milligrams, "mL" for milliliter or milliliters, "H" for hydrogen, "hr" or "h" for hour or hours, "mmol" for millimoles, "min" or "m" for minute or minutes, "$^1$H-NMR" for proton nuclear magnetic resonance (NMR) spectroscopy, "Hz" for hertz, "HPLC" for high performance liquid chromatography, "$R_t$" for retention time, "M" for mass, "MS" for mass spectroscopy, and "NMR" for nuclear magnetic resonance spectroscopy.

Example 1

Preparation of 4-(indol-3-ylmethylene)-3-(1,3-thiazol-2-yl)-2-pyrazolin-5-one (Compound 25)

(a) 3(1,3-thiazol-2-yl)-2-pyrazolin-5-one (VIa)

To a vigorously stirred suspension of NaH (60% dispersion in mineral oil, 904 mg, 22.64 mmol, 2.9 equiv.) and diethyl carbonate (1.9 mL, 15.69 mmol, 1.99 equiv.) in dry toluene (15 mL) was added drop wise (over a period of 1 h) a solution of the methyl ketone (2-acetyl thiazole) (1 g., 7.87 mmol) in toluene (5 mL) under reflux. After addition, the mixture was stirred at reflux for 0.5 h. The mixture was cooled to RT and was acidified with glacial acetic acid. After adding cold water, the mixture was extracted 3 times with ethyl acetate. Combined organic extract was washed with water and brine. After drying over $MgSO_4$, solvent was evaporated to furnish the crude β-ketoester. To the crude product was added absolute ethanol (5 mL) and hydrazine hydrate (0.5 mL). The mixture was kept under reflux for 3 h. Solvent was evaporated in vacuo. The crude mass was purified by flash chromatography (EtOAc: MeOH 95:5). The solid obtained was stirred in EtOAC for 15 min., filtered and dried to furnish the pyrazolone (VIa) (237 mg, 18%). $^1$H-NMR (DMSO-$d_6$) δ 12.5 (br s, 1H), 11.00 (br s, 1H), 7.74 (s, 1H), 7.57 (s, 1H), 5.7 (s, 1H), MS: 168 (M+H).

(b) Preparation of Compound 25

A mixture of the pyrazolone (VIa) (50 mg, 0.30 mmol) and indole-3-carboxaldehyde (47 mg, 0.32 mmol, 1.08 equiv.) in absolute ethanol (1 mL) along with 2–3 drops of piperidine was stirred at 80–90° C. for 4 h. The solid was filtered and washed with ethanol, dried under vacuo to provide 65 mg (74%) of compound 25 as a single geometrical isomer. $^1$H-NMR (DMSO-d6) δ 11.85 (s, 1H), 9.83 (s, 1H), 9.42 (s, 1H), 8.05 (d, J=3.17 Hz, 1H), 7.80 (m, 2H), 7.58 (m, 1H), 7.30 (m, 3H). MS: 295 (M+H). HPLC: $R_t$=10.10 min.

Example 2

Preparation of 4-[(3,5-dimethylpyrrol-2-yl)methylene]-3-(1,3-thiazol-2-yl)-2 pyrazolin-5-one (Compound 26)

A mixture of the pyrazolone (VIa) (50 mg, 0.30 mmol) and 3,5-dimethyl-1H-pyrrole-2-carboxaldehyde (40 mg, 0.32 mmol, 1.08 equiv.) in absolute ethanol (1 mL) along with 2–3 drops of piperidine was stirred at 80–90° C. for 4 h. The product that separated as a solid was filtered and washed with ethanol. After drying, 65 mg (74%) of compound 26 was isolated as a single geometrical isomer. $^1$H-NMR (DMSO-d6) δ 14.39 (s, 1H), 12.01 (s, 1H), 8.70 (s, 1H), 7.95 (d, J=3.17 Hz, 1H), 7.74 (d, J=3.18 Hz, 1H), 6.26 (s, 1H), 2.36 (s, 3H), 2.27 (s, 3H). MS: 273 (M+H). HPLC: $R_t$=10.54 min.

Example 3

Preparation of 4-[(3,5-dimethylpyrrol-2-yl)methylene]-3-(2-furyl)-2-pyrazolin-5-one (Compound 28)

(a) 3-(2-furyl)-2-pyrazolin-5-one (VIb)

To a vigorously stirred suspension of NaH (60% dispersion in mineral oil, 2.28 g, 56.6 mmol, 2.9 equiv.) and diethyl carbonate (4.7 mL, 38.83 mmol, 1.99 equiv.) in dry toluene (30 mL) was added drop wise (over a period of 1 h) a solution of the methyl ketone, 1-furan-2-yl-ethanone, (2.14 g., 19.51 mmol) in toluene (5 mL) under reflux. After addition, the mixture was stirred at reflux for 0.5 h. The mixture was cooled to RT and was acidified with glacial acetic acid. After adding cold water, the mixture was extracted 3 times with ethyl acetate. Combined organic extract was washed with water and brine. After drying over $MgSO_4$, solvent was evaporated to furnish the crude β-ketoester, 3-furan-2-yl-3-oxo-propionic acid ethyl ester. To the crude product was added absolute ethanol (10 mL) and hydrazine hydrate (1 mL). The mixture was kept under reflux for 3 h. Solvent was evaporated in vacuo. The crude mass was purified by flash chromatography (EtOAc). The solid obtained was stirred in EtOAc for 15 min., filtered and dried to furnish the pyrazolone (VIb) (1.23 g, 42%). $^1$H-NMR (DMSO-d$_6$) δ 12.1 (br s, 1H), 9.5 (br s, 1H), 7.64 (s, 1H), 6.63 (s, 1H), 6.51 (s, 1H), 5.64 (s, 1H). MS: 151 (M+H).

(b) Preparation of Compound (28)

A mixture of the pyrazolone (VIb) (50 mg, 0.33 mmol) 3,5-dimethyl-1H-pyrrole-2-carboxaldehyde (45 mg, 0.36 mmol, 1.09 equiv.) in absolute ethanol (1 mL) along with 2–3 drops of piperidine was stirred at 80–90° C. for 4 h. The mixture was cooled (ice bath) and the product that separated as a solid was filtered and washed with cold methanol. After drying, 58 mg (69%) of compound 28 was isolated as a single geometrical isomer. $^1$H-NMR (DMSO-d6) δ 14.47 (s, 1H), 11.81 (s, 1H), 7.82 (s, 1H), 7.78 (s, 1H), 6.86 (d, J=3.30 Hz, 1H), 6.61 (s, 1H), 6.22 (s, 1H), 2.35 (s, 3H), 2.27 (s, 3H). MS: 256 (M+H). HPLC: $R_t$=10.51 m.

Example 4

Preparation of 3-(2-furyl)-4-(indol-3-ylmethylene)-2-pyrazolin-5-one (Compound 29)

A mixture of the pyrazolone (VIb) (50 mg, 0.33 mmol) and indole-3-carboxaldehyde, (53 mg, 0.36 mmol, 1.09 equiv.) in absolute ethanol (1 mL) along with 2–3 drops of piperidine was stirred at 80–90° C. for 4 h. The mixture was cooled in ice bath, and the product filtered and washed with cold methanol. After drying, 36 mg (40%) of compound 29 was isolated as a single geometrical isomer. $^1$H-NMR (DMSO-d6) δ 12.55 (br s, 1H), 11.62 (s, 1H), 9.82 (s, 1H), 8.45 (s, 1H), 7.89 (m, 2H), 7.56 (m, 1H), 7.28 (m, 2H), 6.96 (m, 1H), 6.66 (m, 1H). MS: 278 (M+H). HPLC: $R_t$=9.80 m.

Example 5

Preparation of 4-[(3,5-dimethylpyrrol-2-yl)methylene]-3-(3-thienyl)-2-pyrazolin-5-one (Compound 37)

(a) Preparation of 3-(3-thienyl)-2-pyrazolin-5-one (VIc)

To a vigorously stirred suspension of NaH (60% dispersion in mineral oil, 830 mg, 20.3 mmol, 2.85 equiv.) and diethyl carbonate (1.7 mL, 14.04 mmol, 1.99 equiv.) in dry toluene (15 mL) was added drop wise (over a period of 1 h) a solution of the methyl ketone, 1-thiophen-3-yl-ethanone (900 mg., 7.14 mmol.) in toluene (5 mL) under reflux. After addition, the mixture was stirred at reflux for 0.5 h. The mixture was cooled to RT and was acidified with glacial acetic acid. After adding cold water, the mixture was extracted 3 times with ethyl acetate. Combined organic extract was washed with water and brine. After drying over $MgSO_4$, solvent was evaporated to furnish the crude β-ketoester, 3-Oxo-3-thiophen-3-yl-propionic acid ethyl. To the crude product was added absolute ethanol (5 mL) and hydrazine hydrate (0.5 mL). The mixture was kept under reflux for 4 h. Solvent was evaporated in vacuo. The crude mass was purified by flash chromatography (EtOAc). The pyrazolone (VIc) was isolated as a solid (940 mg, 79%).

$^1$H-NMR (DMSO-d6) δ 11.8 (br s, 1H), 9.7 (br s, 1H), 7.68 (d, J=1.98 Hz, 1H), 7.55 (m, 1H), 7.38 (d, J=4.92 Hz, 1H), 5.74 (s, 1H). MS: 167(M+H).

(b) Preparation of Compound (37)

A mixture of the pyrazolone (VIc) (50 mg, 0.30 mmol) 3,5-dimethyl-1H-pyrrole-2-carboxaldehyde (41 mg, 0.33 mmol, 1.11 equiv.) in absolute ethanol (1 mL) along with 2–3 drops of piperidine was stirred at 80–90° C. for 3 h. The product that separated as a solid was filtered and washed with ethanol. After drying, 64 mg (79%) of the compound 37 was isolated as a single geometrical isomer. $^1$H-NMR (DMSO-d6) δ 14.44 (br s, 1H), 11.68 (s, 1H), 7.89 (d, J=1.60 Hz, 1H), 7.64 (m, 1H), 7.46 (s, 1H), 7.38 (m, 1H), 6.18 (s, 1H), 2.34 (s, 1H), 2.34 (s, 3H), 2.23 (s, 3H). MS: 272 (M+H). HPLC: $R_t$=10.75 m.

Example 6

Preparation of 4-(indol-3-ylmethylene)-3-(2-thienyl)-2-pyrazolin-5-one (Compound 38)

A mixture of the pyrazolone (VIc) (50 mg, 0.30 mmol) and indole-3-carboxaldehyde, (47 mg, 0.32 mmol, 1.06 equiv.) in absolute ethanol (1 mL) along with 2–3 drops of piperidine was stirred at 80–90° C. for 4 h. The product separated as a solid was filtered and washed with ethanol. After drying, 65 mg (74%) of the compound 38 was isolated as a single geometrical isomer. $^1$H-NMR (DMSO-d6) δ 12.48 (br s, 1H), 11.48 (s, 1H), 9.81 (s, 1H), 8.13 (s, 1H), 8.00 (d, J=1.95 Hz, 1H), 7.83 (m, 1H), 7.68 (m, 1H), 7.54 (m, 1H), 7.45 (d, J=5.02 Hz, 1H), 7.24 (m, 2H). MS: 294 (M+H). HPLC: $R_t$=10.27 m.

Example 7

Preparation of 3-benzo[d]furan-2-yl-4-[(3,5-dimethylpyrrol-2-yl)methylene]-2-pyrazolin-5-one (Compound 57)

(a) Preparation of 3-benzo[d]furan-2-yl-2-pyrazolin-5-one (VId)

To a vigorously stirred suspension of NaH (60% dispersion in mineral oil, 2.6 g, 65 mmol, 3.32 equiv.) and diethyl carbonate (4.7 mL, 38.83 mmol, 1.99 equiv.) in dry toluene (30 mL) was added drop wise (over a period of 1 h) a solution of the methyl ketone, 1-benzofuran-2-yl-ethanone (1 g, 7.87 mmol) in toluene (5 mL) under reflux. After addition, the mixture was stirred at reflux for 0.5 h. The mixture was cooled to RT and was acidified with glacial acetic acid. After adding cold water, the mixture was extracted 3 times with ethyl acetate. Combined organic extract was washed with water and brine. After drying over MgSO$^4$, solvent was evaporated to furnish the crude βketoester, 3-benzofuran-2-yl-3-oxo-propionic acid ethyl ester. To the crude product was added absolute ethanol (10 mL) and hydrazine hydrate (1.5 mL, excess). The mixture was kept under reflux for 4 h. A solid separated, which was filtered and washed with EtOH. Upon drying, a 1.87 g (48%) of the pyrazolone (VId) was isolated. $^1$H-NMR (DMSO-d6) δ 12.5 (br s, 1H), 10.1 (br s, 1H), 7.62–7.18 (series of multiplets, 4H), 7.10 (s, 1H), 5.87 (s, 1H). MS: 201(M+H)

(b) Preparation of Compound (57)

A mixture of the pyrazolone (VId) (75 mg, 0.375 mmol) and 3,5-dimethyl-1H-pyrrole-2-carboxaldehyde (50 mg, 0.40 mmol, 1.07 equiv.) in absolute ethanol (1 mL) along with 2–3 drops of piperidine was stirred at 80–90° C. for 4 h. The product that separated as a solid was filtered and washed (with ethanol). After drying, 105 mg (92%) of compound 57 was isolated as a single geometrical isomer. $^1$H-NMR (DMSO-d6) δ 14.5 (br s, 1H), 12.04 (br s, 1H), 7.93 (s, 1H), 7.67 (m, 2H), 7.36–7.24 (overlapping m & s, 3H), 6.26 (s, 1H), 2.37 (s, 3H), 2.33 (s, 3H). MS: 306 (M+H). HPLC: $R_t$=13.46 m.

Example 8

Preparation of 4-[(3,5-dimethylpyrrol-2-yl)methylene]-3-pyrazin-2-yl-2-pyrazolin-5-one (Compound 74)

(a) Preparation of 3-pyrazin-2-yl-2-pyrazolin-5-one (VIe)

To a solution of the methyl pyrazine-2-carboxylate (2.51 g, 18.18 mmol), in methyl acetate (10 mL) was added NaH (60% dispersion in mineral oil, 815 mg, 20.37 mmol, 1.12 equiv.) with continuous stirring for 0.5 h. The mixture was stirred under reflux for 2.5 h. The reaction mixture was cooled to RT and poured to water. The mixture was extracted from diethyl ether (twice). The aqueous layer was neutralized with conc. HCl, was saturated with salt, and was extracted repeatedly with dichloromethane. After work up and solvent evaporation, the crude β-ketoester, was obtained which was used directly for pyrazolone formation without further purification. To the crude product was added absolute ethanol (40 mL) and hydrazine hydrate (3 mL, excess). The mixture was kept under reflux for 4 h. A solid separated, which was filtered and washed with MeOH. Upon drying, 1.57 g (52%) of the pyrazolone (VIe) was isolated. $^1$H-NMR (DMSO-d6) δ 9.00 (s, 1H), 8.50 (s, 1H), 8.41 (d, J=2.37 Hz, 1H), 5.84 (s merged with water and other exchangeable protons, 1H). MS: 163(M+H).

(b) Preparation of Compound 74

A mixture of the pyrazolone (VIe) (50 mg, 0.30 mmol) and 3,5-dimethyl-1H-pyrrole-2-carboxaldehyde, (42 mg, 0.34 mmol, 1.13 equiv.) in absolute ethanol (1 mL) along with 2–3 drops of piperidine was stirred at 80–90° C. for 4 h. The product that separated as a solid was filtered from hot reaction mixture, and washed with hot ethanol. After drying, 40 mg (50%) of compound (74) was isolated as a single geometrical isomer.

$^1$H-NMR (DMSO-d6) δ 14.5 (br s, 1H), 12.10 (s, 1H), 9.14 (d, J=0.82 Hz, 1H), 8.71 (s, 1H), 7.67 (d, J=1.81 Hz, 1H), 8.58 (d, J=2.47 Hz, 1H), 6.24 (s, 1H), 2.36 (s, 3H), 2.25 (s, 3H). MS: 268 (M+H). HPLC: $R_t$=9.89 m.

Example 9

Preparation of 4-[(3,5-dimethylpyrrol-2-yl)methylene]-3-indol-3-yl-2-pyrazolin-5-one (Compound 76)

(a) Preparation of methyl 1-(2,2-dimethylethoxycarbonyl)-indole-3-carboxylate

Methyl 1H-indole-3-carboxylate (8.95 g, 50 mmoles) and di-tert-butyl dicarbonate (11.5 g, 52 mmoles) were dissolved in acetonitrile (100 mL), solid 4-dimethylamino pyridine (0.610 g, 5 mmol) was added and reaction mixture stirred at room temperature overnight. Reaction mixture was concentrated in vacuo and the residue was taken up in ethyl acetate (300 mL) and washed successively with saturated brine, ice cold (~5° C.) 1N HCl solution and saturated brine solution. Organic layer was dried over anhydrous sodium sulphate, filtered and concentrated in vacuo to a clear liquid, (13.9 g).

(b) Preparation of ethyl 3-indol-3-yl-3-oxopropanoate (Va)

A solution of diisopropyl amine (13 mL, 100 mmol) and tetramethylethylene diamine (15 mL, 100 mmol) in THF (150 mL) was cooled in dry ice-acetone bath under argon atmosphere. A 2.5N solution of n-butyl lithium in hexane (40 mL, 100 mmol) was added over 30 minutes and EtOAc (10 mL, 108 mmol) was added and solution stirred for additional 30 minutes. A solution of N-BOC methyl indole-3-carboxylate (IIIa) (6.875 g, 25 mmol), in THF (50 mL) was added rapidly and the reaction mixture was stirred at –78° C. for 1 h and then at –15° C. for an additional 1 h. Reaction mixture was allowed to warm to 15° C., and the reaction was quenched with glacial acetic acid (10 mL). Ethyl acetate (250 mL) was added and the organic layer was successively washed with 1N citric acid solution (2×150 mL), saturated brine (2×100 mL), the organic layer was dried over anhydrous sodium sulphate, filtered and concentrated in vacuo. The crude product was purified was purified by flash chromatography over silica gel and 1:1 ethyl acetate and hexane were used as eluent to provide the desired compound (Va) (1.2 g) and its N-BOC derivative (Vb) (1.2 g) in a combined yield of 30%.

(c) Preparation of 3-indol-3-yl-2-pyrazolin-5-one (VIf)

The compound (Va) (600 mg, 3 mmol) was added to a mixture of absolute ethanol (7 mL) and hydrazine hydrate (1 mL). The mixture was kept under reflux for 4 h. Solvent was evaporated and the residue was taken in ethyl acetate (20 mL) and washed with water and brine. The ethyl acetate layer was dried over MgSO$_4$ to yield the product as dark brown solid, which showed the presence of two major spots. Stirred the solid in ethanol and filtered the solid. The solvent was evaporated to yield compound (VIf) as thick gum (126 mg, 35%)

(d) Preparation of Compound 76

A mixture of compound (VIf) (60 mg, 0.3 mmol), 3,5-dimethyl-1H-pyrorole-2-carboxaldehyde (41 mg, 0.33 mmol, 1.11 equv.) in absolute ethanol (1.3 mL) along with 3 drops of piperidine was stirred at 85° C. for 3 h. The product that separated as solid was filtered, washed with ethanol and dried under vacuum (58 mg, 63%).

Example 10

Preparation of 4-[(3,5-dimethylpyrrol-2-yl)methyl]-3-indol-3-yl-2-pyrazolin-5-one (Compound 77)

A solution of compound 76 (38 mg, 0.12 mmol) in a solvent mixture of dimethyl sulfoxide and methanol (1:1, 1.5 mL) was added sodium borohydride (45 mg, 1.2 mmol) in portions. After 15 min., the reaction was quenched with acetic acid and water (10 mL). The mixture was extracted with ethyl acetate and the organic layer was washed with water and brine. The solvent was dried over $MgSO_4$ and evaporated to yield a reddish brown residue, which on ether addition precipitated as pale brown solid, compound 77, (27 mg, 71%)

Example 11

Preparation of 4-[(2,6-difluorophenyl)(5-oxo-3-pyrazin-2-yl(2-pyrazolin-4yl))methyl]-3-pyrazin-2-yl-2-pyrazolin-5-one (Compound 78)

A mixture of the pyrazolone (VIe) (30 mg, 0.18 mmol) and 2,6-difluorobenzaldehyde (37 mg, 0.26 mmol) in absolute ethanol (1 mL) along with 2–3 drops of piperidine was stirred at 85–90° C. for 21.5 hrs. The product that separated as a solid was filtered and washed with additional ethanol. After drying, 68 mg of compound 78 was isolated. $^1$H-NMR (DMSO-d6) δ 11.5 (br s, 2H), 8.85 (s, 2H), 8.3 (d, J=2.16 Hz, 2H), 8.07 (s, 2H), 7.06 (s, 1H), 6.96 (m, 1H), 6.66 (m, 2H), 4.4 (br s, 2H), MS: 471 (M+Na). HPLC: $R_t$=6.18 m.

The compounds of examples 1 to 21, as well as additional compounds which were prepared by the methods consistent with the teachings of the foregoing examples and synthetic schemes, are set forth in Table 1 and Table 1a. These compounds are presented to illustrate the present invention, and are not intended to be limiting thereof.

TABLE 1

| Compound No. | R1 | R3 | R4-(Het) |
|---|---|---|---|
| 1 | —H | (2,4-dimethyl-1H-pyrrol-5-yl with $X_3$) | (furan-3-yl with $X_4$) |
| 2 | —H | (2,4-dimethyl-1H-pyrrol-5-yl with $X_3$) | (xanthen-9-yl with $X_4$) |
| 3 | —H | (2,4-dimethyl-1H-pyrrol-5-yl with $X_3$) | (pyridin-4-yl with $X_4$) |
| 4 | —H | (2,2-diphenylethenyl with $X_3$) | (furan-3-yl with $X_4$) |
| 5 | —H | (benzyl 4-ethyl-3-methyl-1H-pyrrole-2-carboxylate-5-yl with $X_3$) | (furan-3-yl with $X_4$) |

TABLE 1-continued

[Structure: pyrazolone core with R1 on N, R4-(Het) and R3/R2 on exocyclic methylene]

| Compound No. | R1 | R3 | R4-(Het) |
|---|---|---|---|
| 6 | —H | 2-X₃, 3-CH₃, 4-I, 5-I substituted 1H-pyrrole (with I and CH₃) | 3-X₄-furan |
| 7 | —H | 5-X₃-1H-pyrrole with 2-C(O)OCH₂CH₃, 3-CH₂CH₂C(O)OCH₂CH₃, 4-CH₂C(O)OCH₂CH₃ | 3-X₄-furan |
| 8 | —H | 5-X₃-2-CH₃-3,4-dibromo-1H-pyrrole | 3-X₄-furan |
| 9 | —H | 3-X₃-1H-indole | 3-X₄-furan |
| 10 | —H | 5-X₃-2-CH₃-4-CH₃-1H-pyrrole | 3-X₄-pyridine |
| 11 | —H | 3-X₃-5-methoxy-1H-indole | 3-X₄-furan |
| 12 | —H | 2-X₃-1H-pyrrole | 3-X₄-furan |

TABLE 1-continued
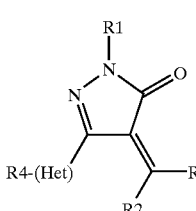
| Compound No. | R1 | R3 | R4-(Het) |
|---|---|---|---|
| 13 | —H | 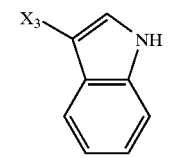 | 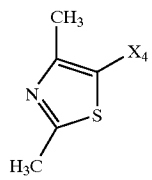 |
| 14 | —H | 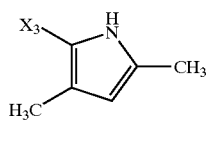 | 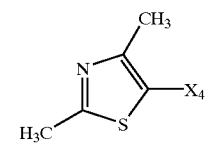 |
| 15 | —H | 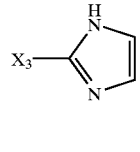 | 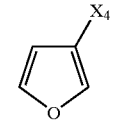 |
| 16 | —H | 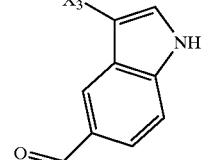 | 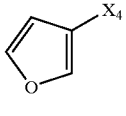 |
| 17 | —H | 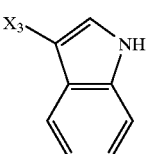 | 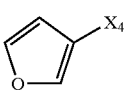 |
| 18 | —H | 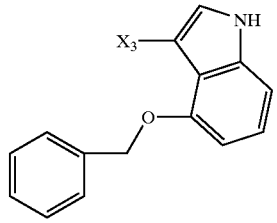 | 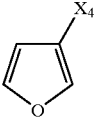 |

TABLE 1-continued
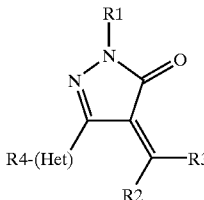
| Compound No. | R1 | R3 | R4-(Het) |
|---|---|---|---|
| 19 | —H | 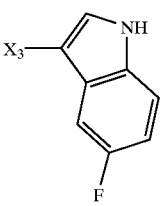 | 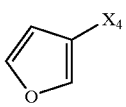 |
| 20 | —H | 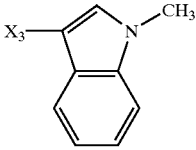 | 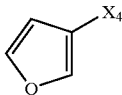 |
| 21 | —H | 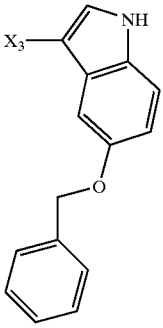 | 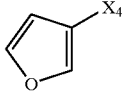 |
| 22 | —H | 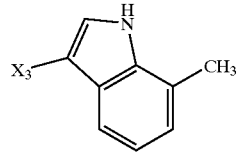 | 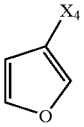 |
| 23 | —H | 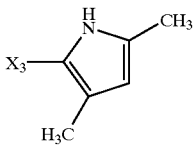 | 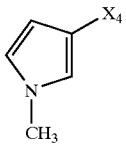 |
| 24 | —H | 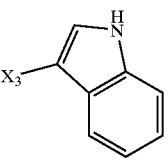 | 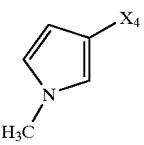 |

TABLE 1-continued

[Structure: pyrazolone core with R1 on N, R4-(Het) and R2/R3 on exocyclic methylene]

| Compound No. | R1 | R3 | R4-(Het) |
|---|---|---|---|
| 25 | —H | 3-indolyl (X₃) | 2-thiazolyl (X₄) |
| 26 | —H | 2,4-dimethyl-1H-pyrrol-5-yl (X₃), with CH₃ groups | 2-thiazolyl (X₄) |
| 27 | —H | 2,4-dimethyl-1H-pyrrol-5-yl (X₃) | 2,4-dimethylfuran-3-yl (X₄) |
| 28 | —H | 2,4-dimethyl-1H-pyrrol-5-yl (X₃) | 2-furyl (X₄) |
| 29 | —H | 3-indolyl (X₃) | 2-furyl (X₄) |
| 30 | —H | 2,4-dimethyl-1H-pyrrol-5-yl (X₃) | 2-pyridyl (X₄) |
| 31 | —H | 4-benzyloxy-1H-indol-3-yl (X₃) | 1-methyl-1H-pyrrol-3-yl (X₄) |

TABLE 1-continued
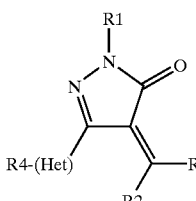
| Compound No. | R1 | R3 | R4-(Het) |
|---|---|---|---|
| 32 | —H | 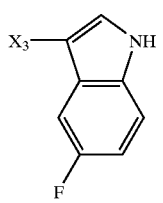 | 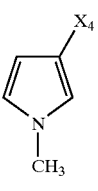 |
| 33 | —H | 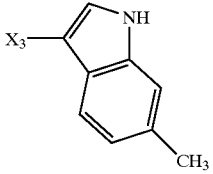 | 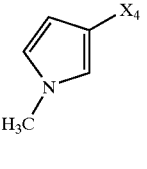 |
| 34 | —H | 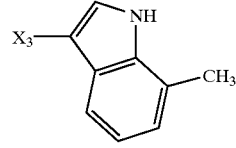 | 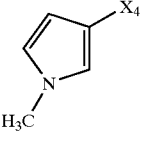 |
| 35 | —H | 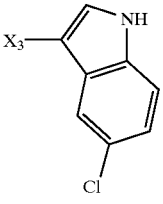 | 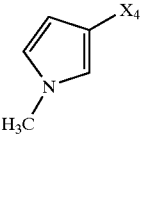 |
| 36 | —H | 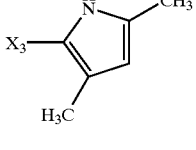 | 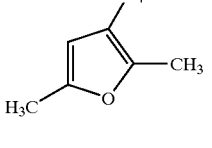 |
| 37 | —H | 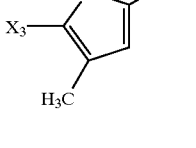 | 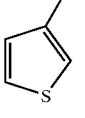 |
| 38 | —H | 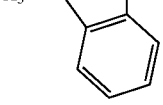 | 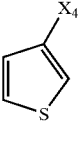 |

TABLE 1-continued
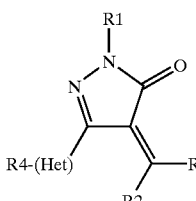
| Compound No. | R1 | R3 | R4-(Het) |
|---|---|---|---|
| 39 | —H | 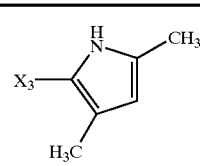 | 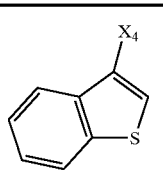 |
| 40 | —H | 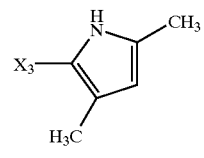 | 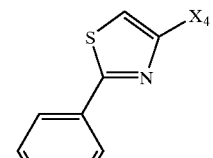 |
| 41 | —H | 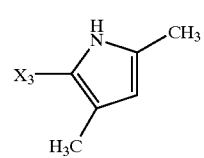 | 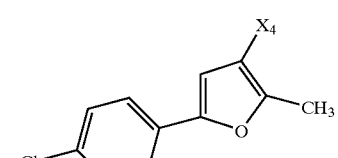 |
| 42 | —H | 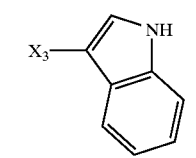 | 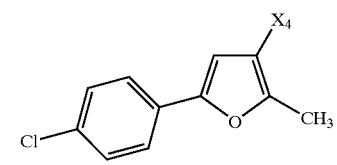 |
| 43 | —H | 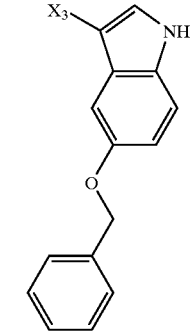 | 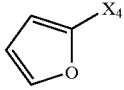 |
| 44 | —H | 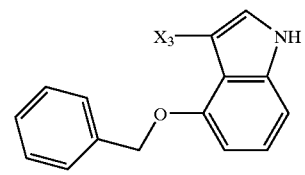 | 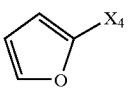 |

TABLE 1-continued

| Compound No. | R1 | R3 | R4-(Het) |
|---|---|---|---|
| 45 | —H | X₃-(1-methylindol-3-yl) | furan-2-yl-X₄ |
| 46 | —H | X₃-(6-methyl-1H-indol-3-yl) | furan-2-yl-X₄ |
| 47 | —H | X₃-(7-methyl-1H-indol-3-yl) | furan-2-yl-X₄ |
| 48 | —H | X₃-(5-fluoro-1H-indol-3-yl) | furan-2-yl-X₄ |
| 49 | —H | X₃-(5-chloro-1H-indazol-3-yl) | furan-2-yl-X₄ |
| 50 | —H | X₃-(6-methoxycarbonyl-1H-indol-3-yl) | furan-2-yl-X₄ |

TABLE 1-continued
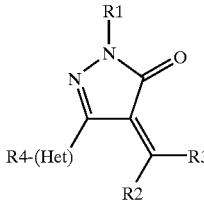
| Compound No. | R1 | R3 | R4-(Het) |
|---|---|---|---|
| 51 | —H | 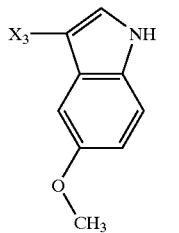 | 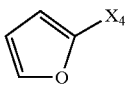 |
| 52 | —H | 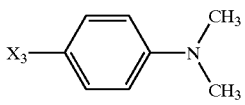 | 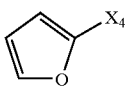 |
| 53 | —H | 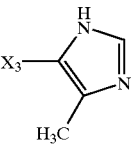 | 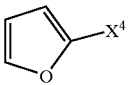 |
| 54 | —H | 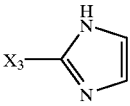 | 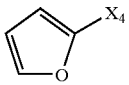 |
| 55 | —H | 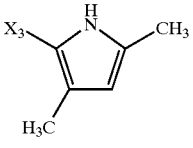 | 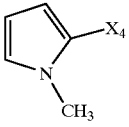 |
| 56 | —H | 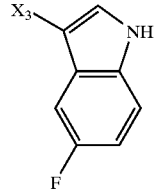 | 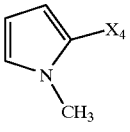 |
| 57 | —H | 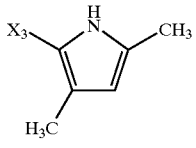 | 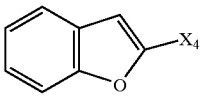 |
| 58 | —H | 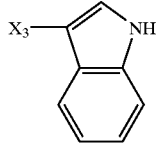 | 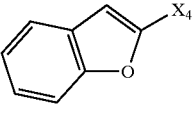 |

TABLE 1-continued
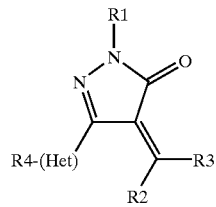
| Compound No. | R1 | R3 | R4-(Het) |
|---|---|---|---|
| 59 | —H | 1-methylindol-3-yl (X₃) | benzofuran-2-yl (X₄) |
| 60 | —H | 1-methylindol-3-yl (X₃) | thiazol-2-yl (X₄) |
| 61 | —H | 2,4-dimethyl-1H-pyrrol-5-yl (X₃) | thiophen-2-yl (X₄) |
| 62 | —H | 1H-indol-3-yl (X₃) | thiophen-2-yl (X₄) |
| 63 | —H | 1-methylindol-3-yl (X₃) | thiophen-2-yl (X₄) |
| 64 | —H | 1-(2-cyanoethyl)indol-3-yl (X₃) | thiazol-2-yl (X₄) |
| 65 | —H | 1-(2-cyanoethyl)indol-3-yl (X₃) | furan-3-yl (X₄) |

TABLE 1-continued
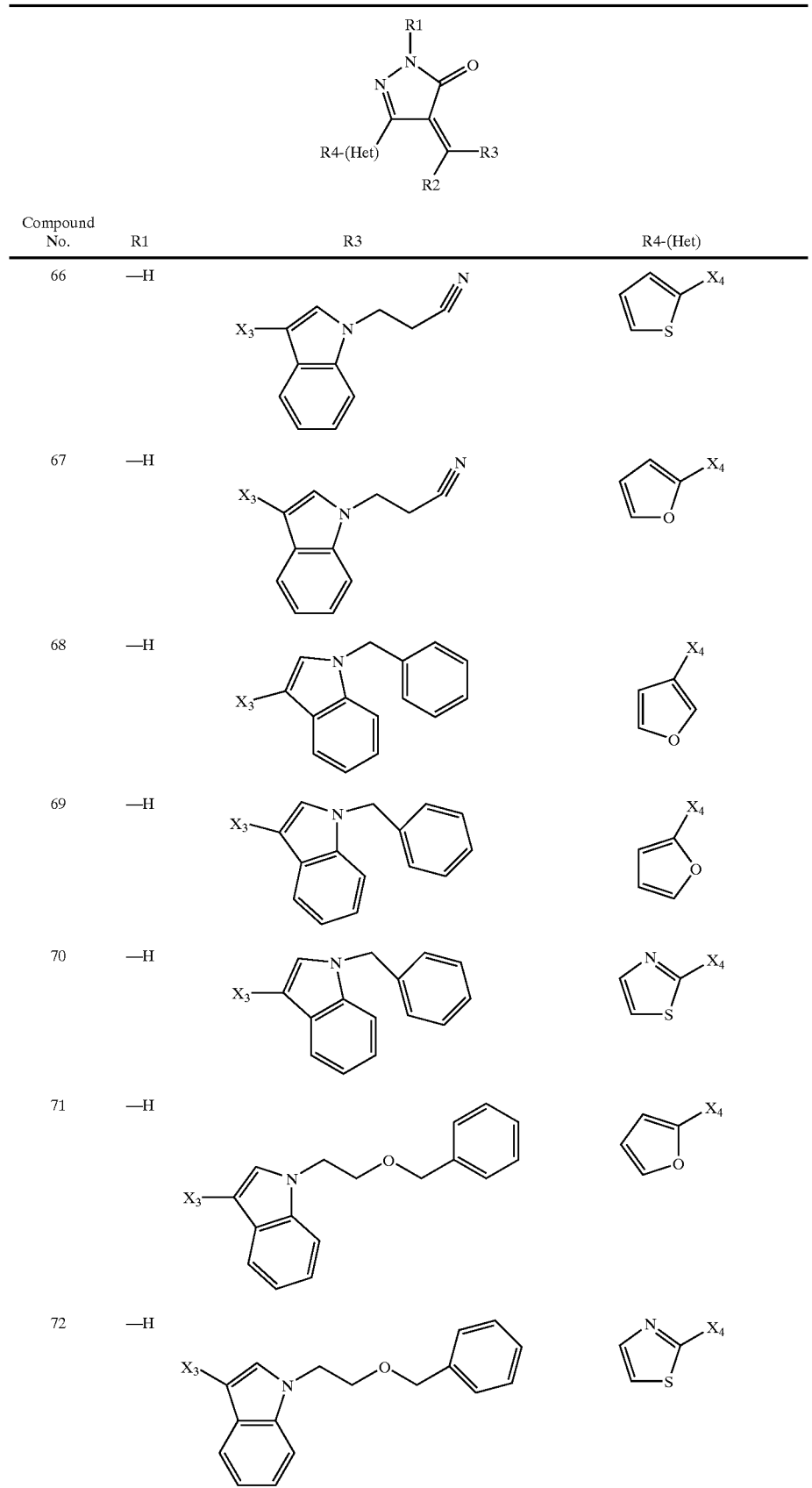

TABLE 1-continued

Structure:

R4-(Het) — C(=) — C(R3)(R2) within a pyrazolone ring: N(R1)—N=C—C(=)—C(=O), where the 3-position bears R4-(Het) and the 4-position bears =C(R2)(R3).

| Compound No. | R1 | R3 | R4-(Het) |
|---|---|---|---|
| 73 | —H | 1-isobutyl-indol-3-yl (X₃ at 3-position) | thiazol-2-yl (X₄) |
| 74 | —H | 3,5-dimethyl-1H-pyrrol-2-yl (X₃ at 2-position, CH₃ at 3 and 5, NH) | pyrazin-2-yl (X₄) |
| 75 | —H | 1-benzyl-indol-3-yl (X₃ at 3-position) | thien-2-yl (X₄) |
| 76 | —H | 3,5-dimethyl-1H-pyrrol-2-yl (X₃) | 1H-indol-3-yl (X₄) |
| 79 | —H | 3,5-dibromo-4-hydroxyphenyl (X₃) | pyrazin-2-yl (X₄) |
| 80 | —H | 3,5-dimethyl-1H-pyrrol-2-yl (X₃) | quinoxalin-2-yl (X₄) |
| 81 | —H | 1-methyl-indol-3-yl (X₃) | quinoxalin-2-yl (X₄) |
| 82 | —H | 3,5-dimethyl-1H-pyrrol-2-yl (X₃) | 4-methyl-1,2,3-thiadiazol-5-yl (X₄) |

TABLE 1-continued
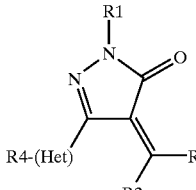
| Compound No. | R1 | R3 | R4-(Het) |
|---|---|---|---|
| 83 | —H | 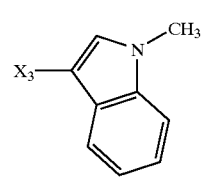 | 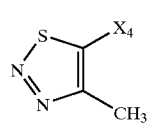 |
| 84 | —H | 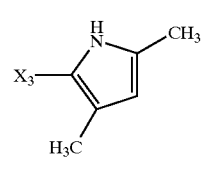 | 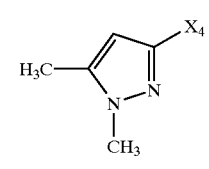 |
| 85 | —H | 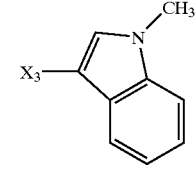 | 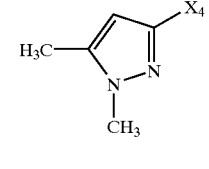 |
| 86 | —H | 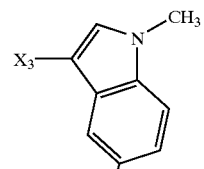 | 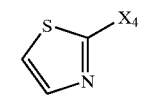 |
| 87 | —H | 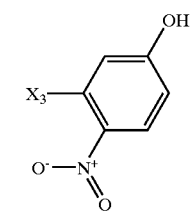 | 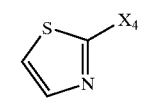 |
| 88 | —H | 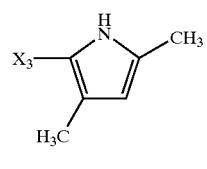 | 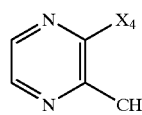 |
| 89 | —H | 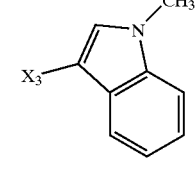 | 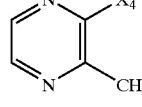 |

TABLE 1-continued
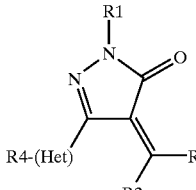
| Compound No. | R1 | R3 | R4-(Het) |
|---|---|---|---|
| 90 | —H | 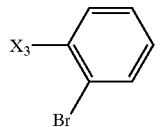 | 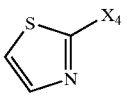 |
| 91 | —H | 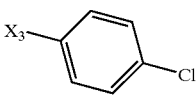 | 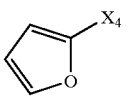 |
| 92 | —H | 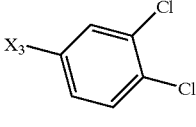 | 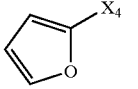 |
| 93 | —H | 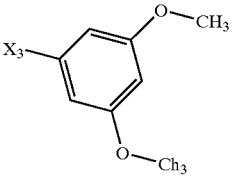 | 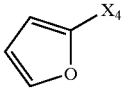 |
| 94 | —H | 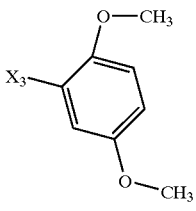 | 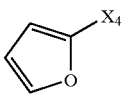 |
| 95 | —H | 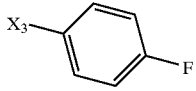 | 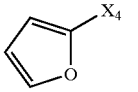 |
| 96 | —H | 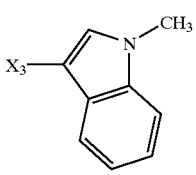 | 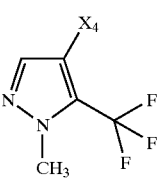 |
| 97 | —H | 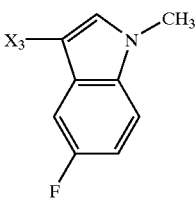 | 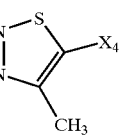 |

TABLE 1-continued
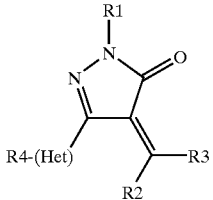
| Compound No. | R1 | R3 | R4-(Het) |
|---|---|---|---|
| 98 | —H | 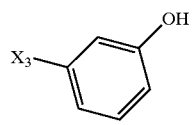 | 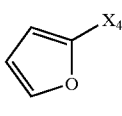 |
| 99 | —H | 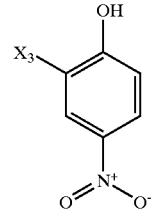 | 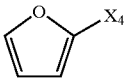 |
| 100 | —H | 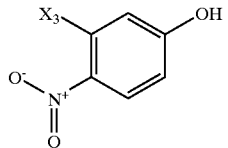 | 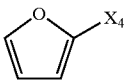 |
| 101 | —H | 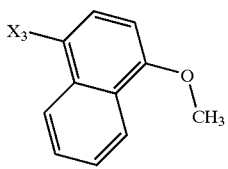 | 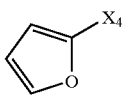 |
| 102 | —H | 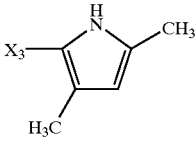 | 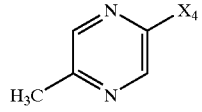 |
| 103 | —H | 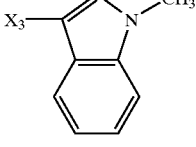 | 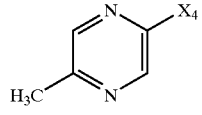 |
| 104 | —H | 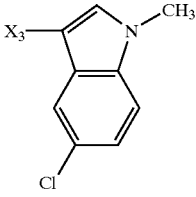 | 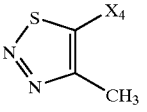 |

TABLE 1-continued
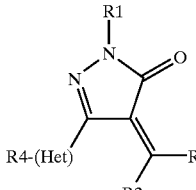
| Compound No. | R1 | R3 | R4-(Het) |
|---|---|---|---|
| 105 | —H | 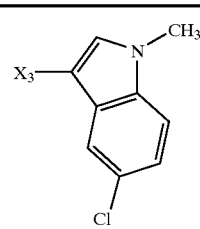 | 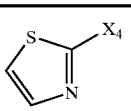 |
| 106 | —H | 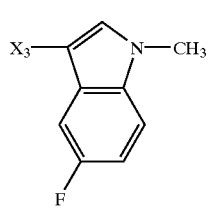 | 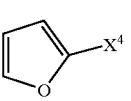 |
| 107 | —H | 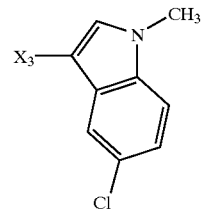 | 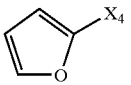 |
| 108 | —H | 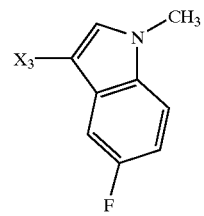 | 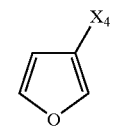 |
| 109 | —H | 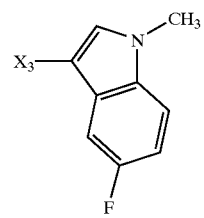 | 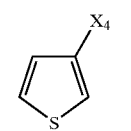 |
| 110 | —H | 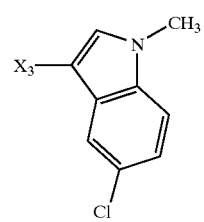 | 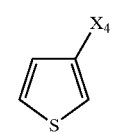 |

TABLE 1-continued

| Compound No. | R1 | R3 | R4-(Het) |
|---|---|---|---|
| 111 | —H | 1-methyl-6-fluoro-indol-3-yl (X3) | thien-5-yl (X4) |
| 112 | —H | 1-methyl-5-chloro-indol-3-yl (X3) | thien-2-yl (X4) |
| 113 | —H | 1-methyl-6-fluoro-indol-3-yl (X3) | thiazol-2-yl (X4) |
| 114 | —H | 1-methyl-6-fluoro-indol-3-yl (X3) | 4-methyl-1,2,3-thiadiazol-5-yl (X4) |
| 115 | —H | 1-methyl-6-(methoxycarbonyl)-indol-3-yl (X3) | thiazol-2-yl (X4) |
| 116 | —H | 1-methyl-6-(methoxycarbonyl)-indol-3-yl (X3) | 4-methyl-1,2,3-thiadiazol-5-yl (X4) |

TABLE 1-continued
| Compound No. | R1 | R3 | R4-(Het) |
|---|---|---|---|
| 117 | —H | 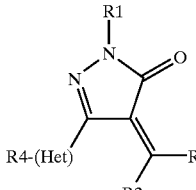 2,4-dimethyl-1H-pyrrol-3-yl (X₃) | 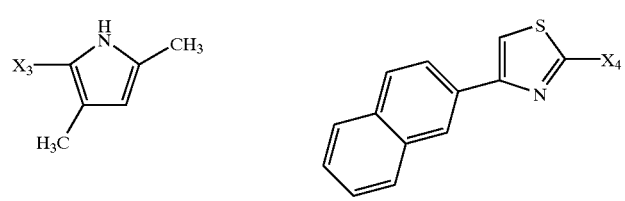 4-(naphthalen-2-yl)thiazol-2-yl (X₄) |
| 118 | —H | 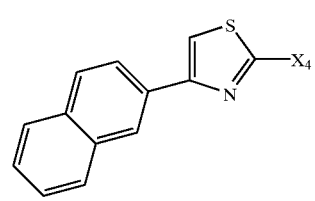 1-methyl-1H-indol-3-yl (X₃) | 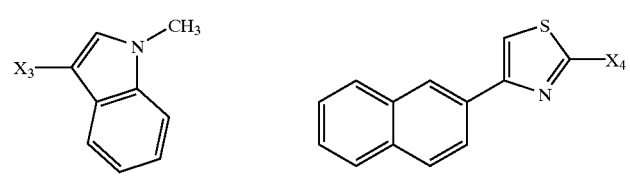 4-(naphthalen-2-yl)thiazol-2-yl (X₄) |
| 119 | —H | 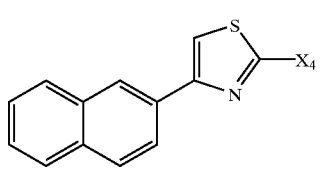 1-methyl-1H-indol-3-yl (X₃) |  pyrazin-2-yl (X₄) |
| 120 | —H | 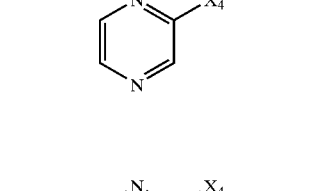 5-fluoro-1-methyl-1H-indol-3-yl (X₃) |  pyrazin-2-yl (X₄) |
| 121 | —H | 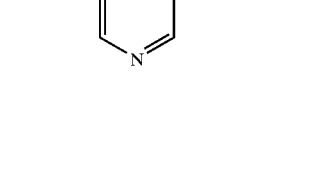 methyl 1-methyl-1H-indole-6-carboxylate-3-yl (X₃) |  pyrazin-2-yl (X₄) |
| 122 | —H | 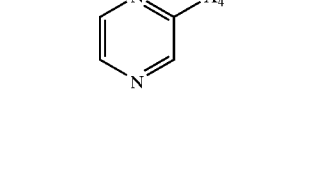 4-ethylphenyl (X₃) | 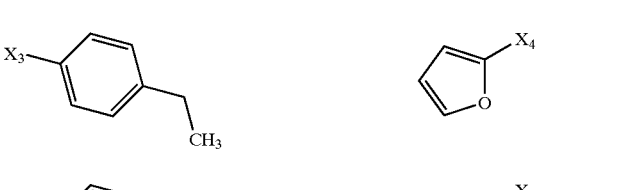 furan-2-yl (X₄) |
| 123 | —H | 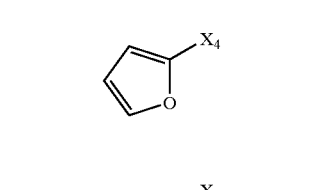 4-(methylthio)phenyl (X₃) | 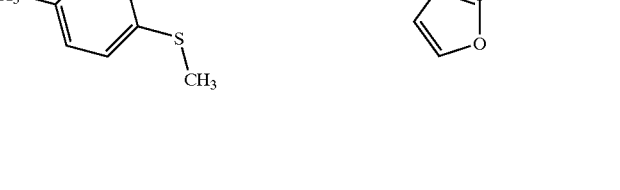 furan-2-yl (X₄) |

TABLE 1-continued
| Compound No. | R1 | R3 | R4-(Het) |
|---|---|---|---|
| 124[a] |  | 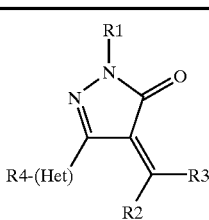 | 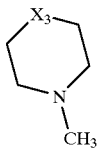 |
| 125 | —H | 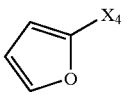 | 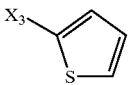 |
| 126 | —H | 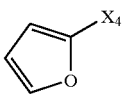 | 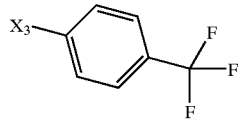 |
| 127 | —H | 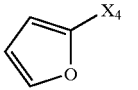 | 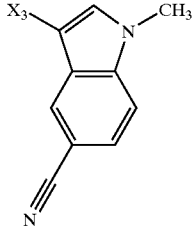 |
| 128 | —H | 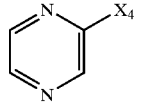 | 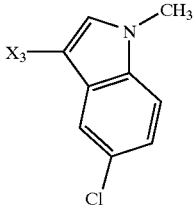 |
| 129 | —H | 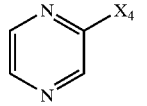 | 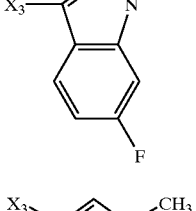 |
| 130 | —H | 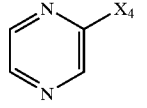 | 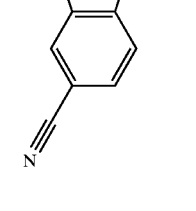 |

TABLE 1-continued
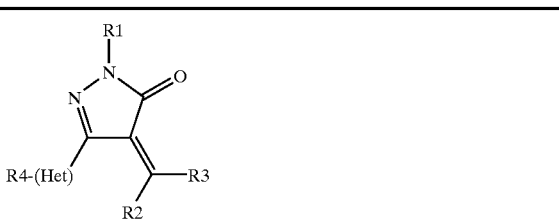
| Compound No. | R1 | R3 | R4-(Het) |
|---|---|---|---|
| 131 | —H | 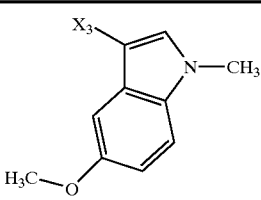 | 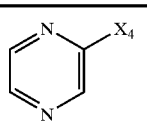 |
| 132 | —H | 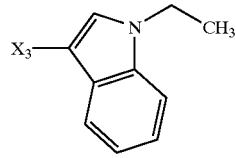 | 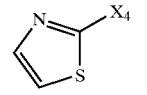 |
| 133 | —H | 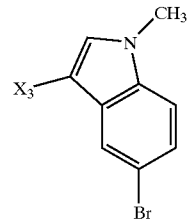 | 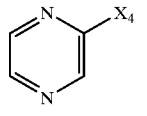 |
| 134 | —H | 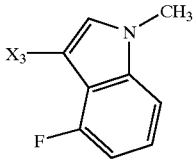 | 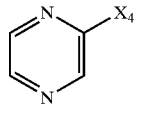 |
| 135 | —H | 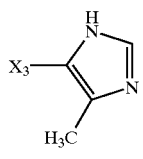 | 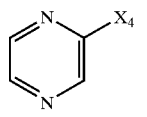 |
| 136 | —H | 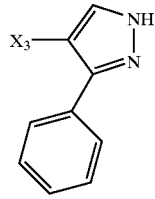 | 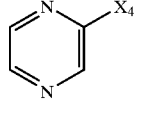 |
| 137 | —H | 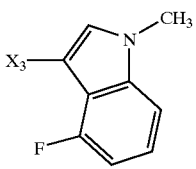 | 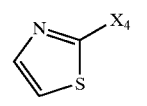 |

TABLE 1-continued
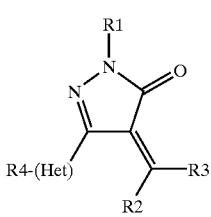
| Compound No. | R1 | R3 | R4-(Het) |
|---|---|---|---|
| 138 | —H | 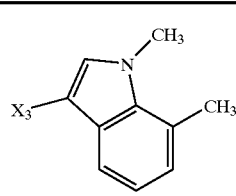 | 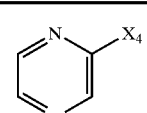 |
| 139 | —H | 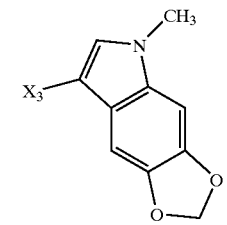 | 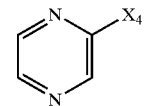 |
| 140 | —H | 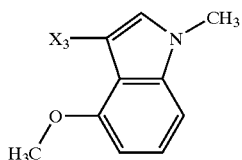 | 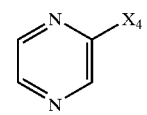 |
| 141 | —H | 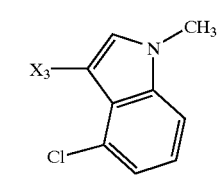 | 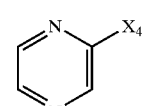 |
| 142 | —H | 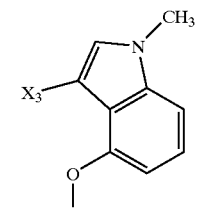 | 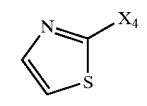 |
| 143 | —H | 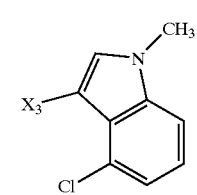 | 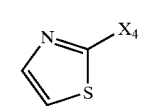 |

TABLE 1-continued
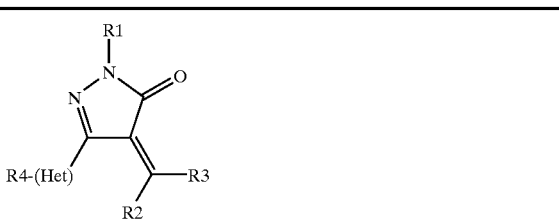
| Compound No. | R1 | R3 | R4-(Het) |
|---|---|---|---|
| 144 | —H | 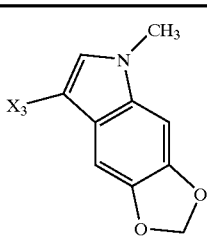 | 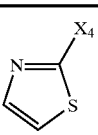 |
| 145 | —H | 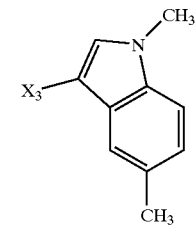 | 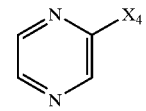 |
| 146 | —H | 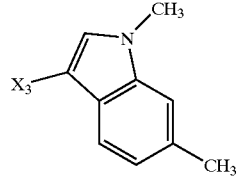 | 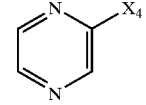 |
| 147 | —H | 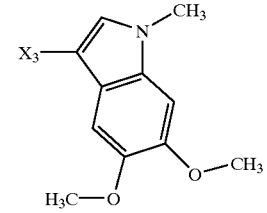 | 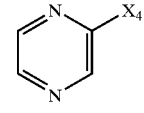 |
| 148 | —H | 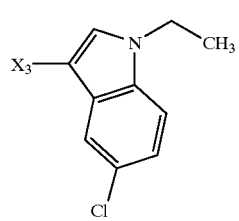 | 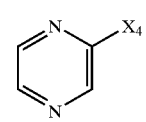 |
| 149 | —H | 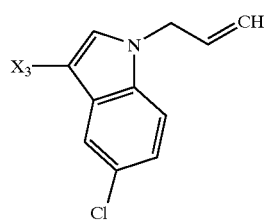 | 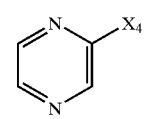 |

TABLE 1-continued
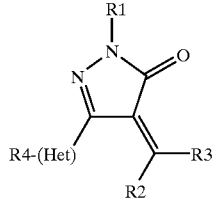
| Compound No. | R1 | R3 | R4-(Het) |
|---|---|---|---|
| 150 | —H | 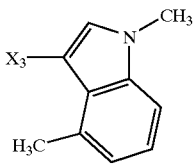 | 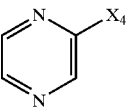 |
| 151 | —H | 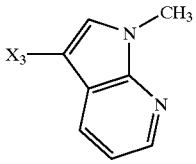 | 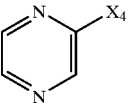 |
| 152 | —H | 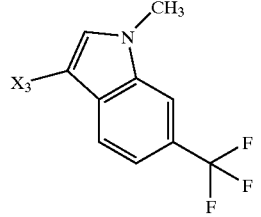 | 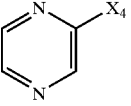 |
| 153 | —H | 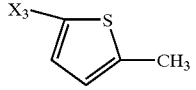 | 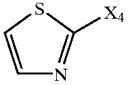 |
| 154 | —H | 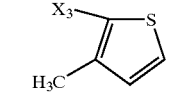 | 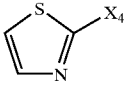 |
| 155 | —H | 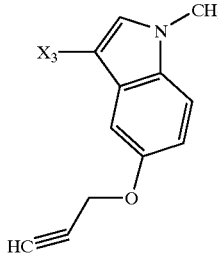 | 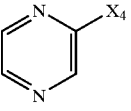 |
| 156 | —H | 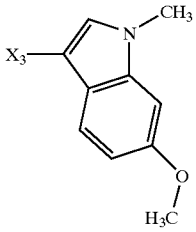 | 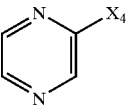 |

TABLE 1-continued
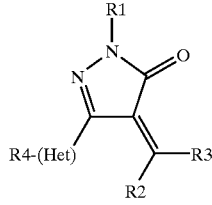
| Compound No. | R1 | R3 | R4-(Het) |
|---|---|---|---|
| 157 | —H | 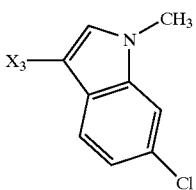 | 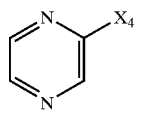 |
| 158 | —H | 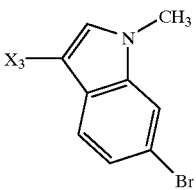 | 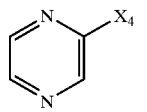 |
| 159 | —H | 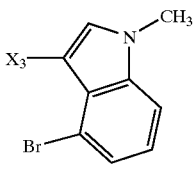 | 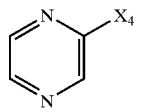 |
| 160 | —H | 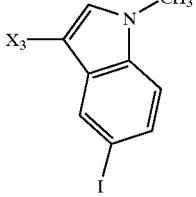 | 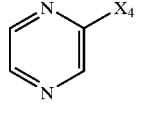 |
| 161 | —H | 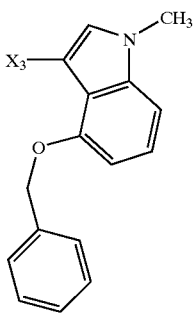 | 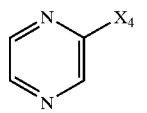 |
| 162 | —H | 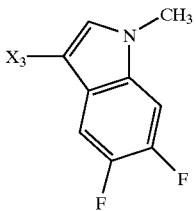 | 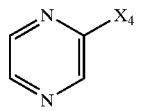 |

TABLE 1-continued
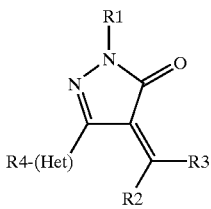
| Compound No. | R1 | R3 | R4-(Het) |
|---|---|---|---|
| 163 | —H | 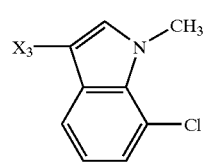 | 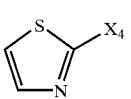 |
| 164 | —H | 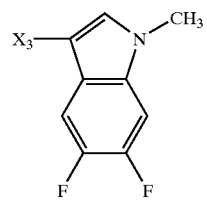 | 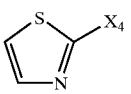 |
| 165 | —H | 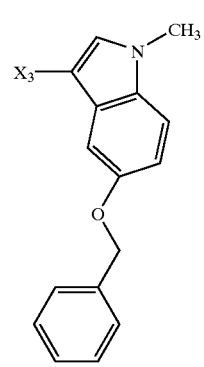 | 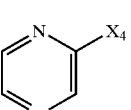 |
| 166 | —H | 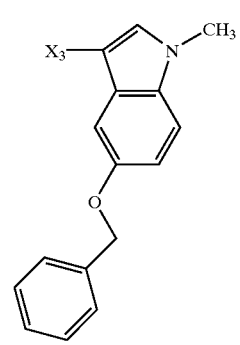 | 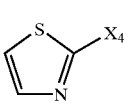 |
| 167 | —H | 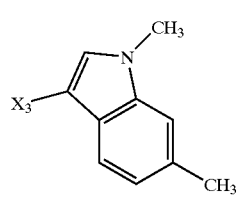 | 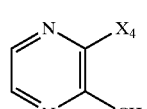 |

TABLE 1-continued
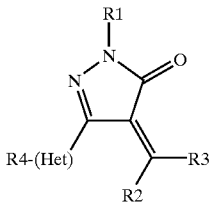
| Compound No. | R1 | R3 | R4-(Het) |
|---|---|---|---|
| 168 | —H | 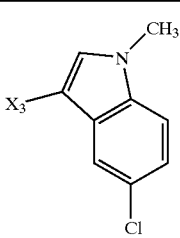 | 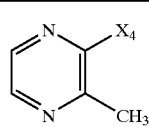 |
| 169 | —H | 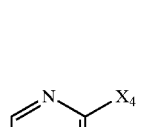 | 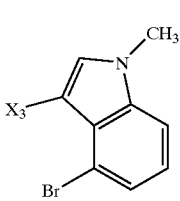 |
| 170 | —H | 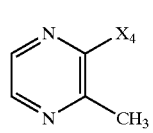 | 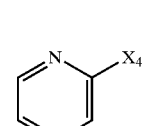 |
| 171 | —H | 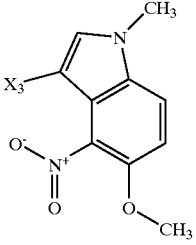 | 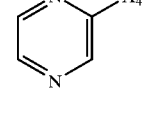 |
| 172 | —H | 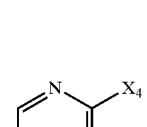 | 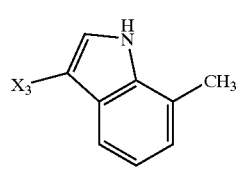 |
| 173 | —H | 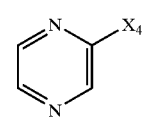 | 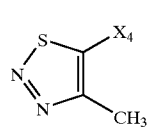 |

TABLE 1-continued

Structure: pyrazolone core with R1 on N, =C(R2)(R3) at 4-position, R4-(Het) at 3-position, =O at 5-position.

| Compound No. | R1 | R3 | R4-(Het) |
|---|---|---|---|
| 174 | —H | X₃-(1H-indol-3-yl) | 4-methyl-1,2,3-thiadiazol-5-yl (X₄) |
| 175 | —H | X₃-(5-chloro-1H-indol-3-yl) | 4-methyl-1,2,3-thiadiazol-5-yl (X₄) |
| 176 | —H | X₃-(3,5-dimethyl-1H-pyrrol-2-yl) | 3-bromo-5-pyridyl (X₄) |
| 177 | —H | X₃-(4-bromo-1-methyl-1H-indol-3-yl) | thiazol-2-yl (X₄) |
| 178 | —H | X₃-(3,5-dimethyl-1H-pyrrol-2-yl) | 3-ethylpyrazin-2-yl (X₄) |
| 179 | —H | X₃-(4,7-dimethoxy-1H-indol-3-yl) | 4-methyl-1,2,3-thiadiazol-5-yl (X₄) |
| 180 | —H | X₃-(4,7-dimethoxy-1H-indol-3-yl) | pyrazin-2-yl (X₄) |

TABLE 1-continued
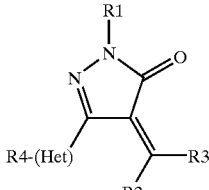
| Compound No. | R1 | R3 | R4-(Het) |
|---|---|---|---|
| 181 | —H | 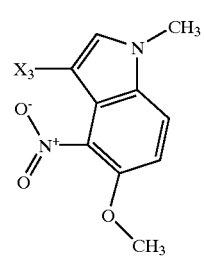 | 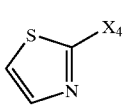 |
| 182 | —H | 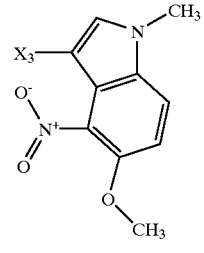 | 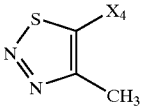 |
| 183 | —H | 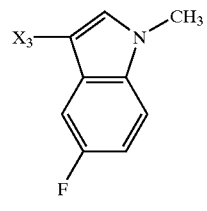 | 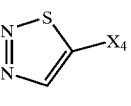 |
| 184 |  | 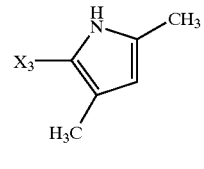 | 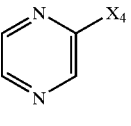 |
| 185 |  | 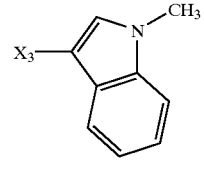 | 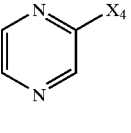 |
| 186 | —H | 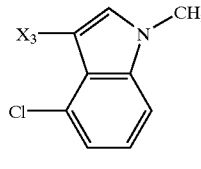 | 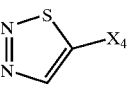 |

TABLE 1-continued
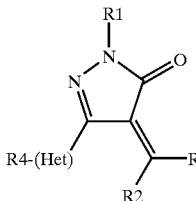
| Compound No. | R1 | R3 | R4-(Het) |
|---|---|---|---|
| 187 | —H | 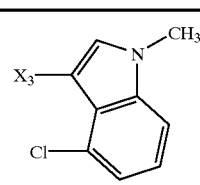 | 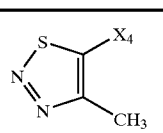 |
| 188 | —H | 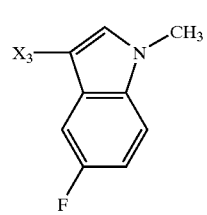 | 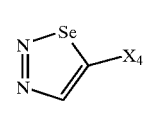 |
| 189 | CH$_3$<br>\|<br>X$_1$ | 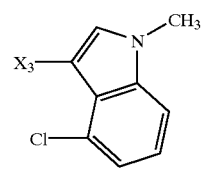 | 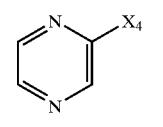 |
| 190 | —H | 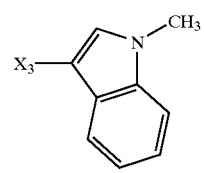 | 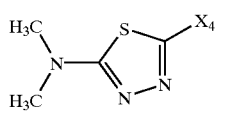 |
| 191 | —H | 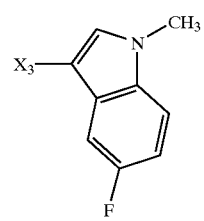 | 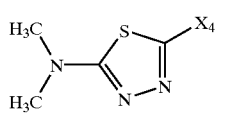 |
| 192 | —H | 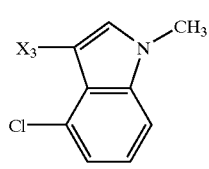 | 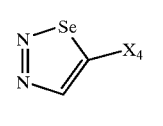 |
| 193 | —H | 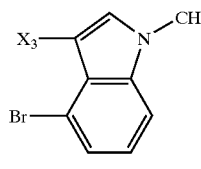 | 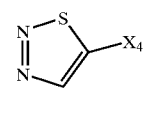 |

TABLE 1-continued
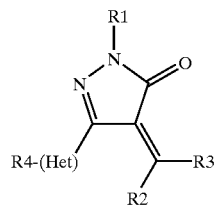
| Compound No. | R1 | R3 | R4-(Het) |
|---|---|---|---|
| 194 | —H | 3-X₃, 1-CH₃, 5,6-diF indole | 1,2,3-thiadiazole-X₄ |
| 195 | —H | 3-X₃, 1-CH₃, 5-Cl indole | 1,2,3-thiadiazole-X₄ |
| 196 | —H | 3-X₃, 1-CH₃, 6-CH₃ indole | 1,2,3-thiadiazole-X₄ |
| 197 | —H | 3-X₃, 1-CH₃, 4-Br indole | 2-N(CH₃)₂-1,3,4-thiadiazole-5-X₄ |
| 198 | —H | 3-X₃, 1-CH₃, 4-Br indole | 4-phenyl-1,2,3-thiadiazole-5-X₄ |
| 199 | —H | 3-X₃, 1-CH₃, 4-I, 5-OCH₃ indole | 1,2,4-triazine-X₄ |

TABLE 1-continued
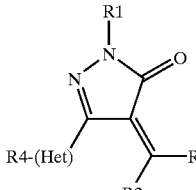
| Compound No. | R1 | R3 | R4-(Het) |
|---|---|---|---|
| 200 | —H | 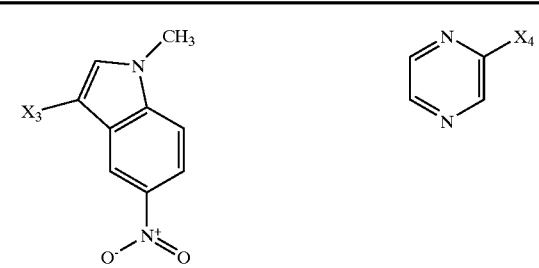 | 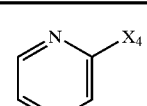 |
| 201 | —H | 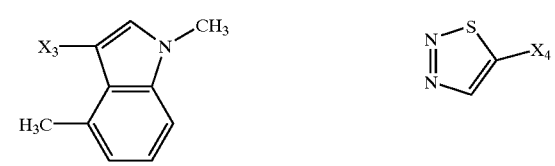 | 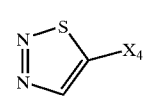 |
| 202 | —H |  | 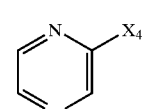 |
| 203 | —H | 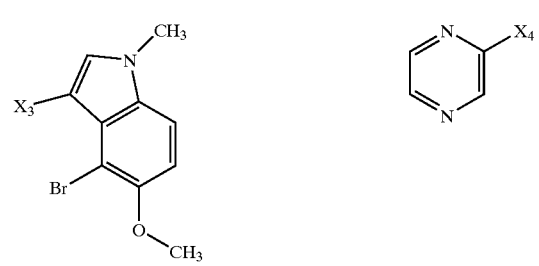 | 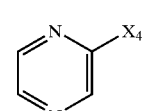 |
| 204 | —H |  | 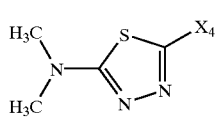 |
| 205 | —H |  | 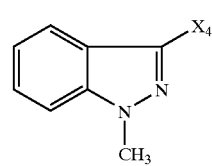 |

TABLE 1-continued
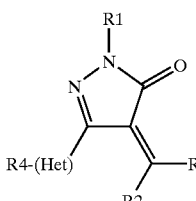
| Compound No. | R1 | R3 | R4-(Het) |
|---|---|---|---|
| 206 | —H | 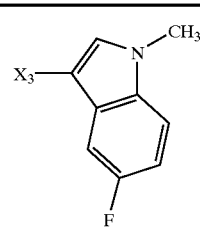 | 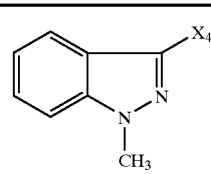 |
| 207 | —H | 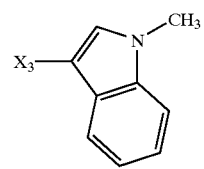 | 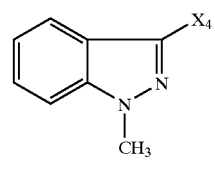 |
| 208 | —H | 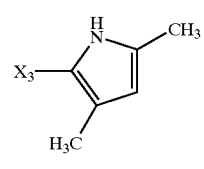 | 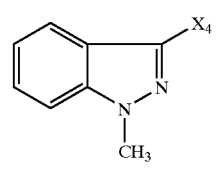 |
| 209 | —H | 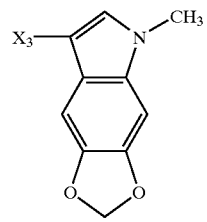 | 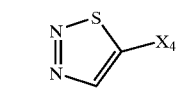 |
| 210 | —H | 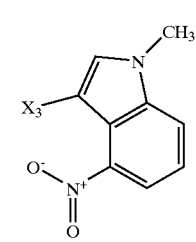 | 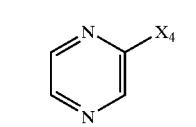 |
| 211 | —H | 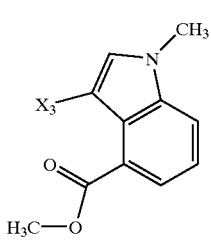 | 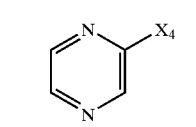 |

TABLE 1-continued
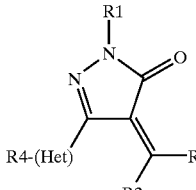
| Compound No. | R1 | R3 | R4-(Het) |
|---|---|---|---|
| 212 | —H | 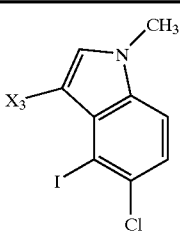 | 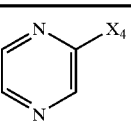 |
| 213 | —H | 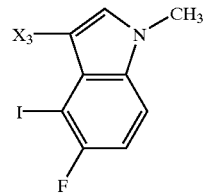 | 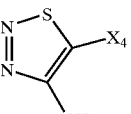 |
| 214 | —H | 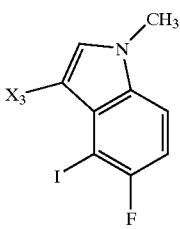 | 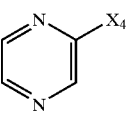 |
| 215 | —H | 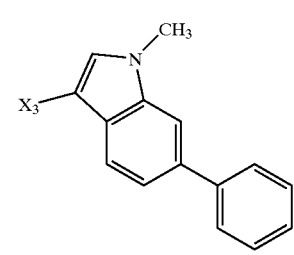 | 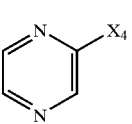 |
| 216 | —H | 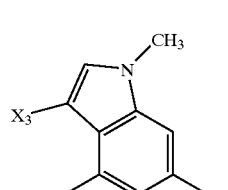 | 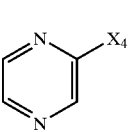 |
| 217 | —H | 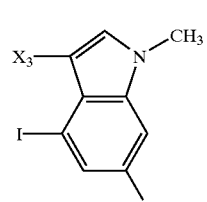 | 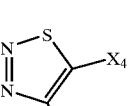 |

TABLE 1-continued
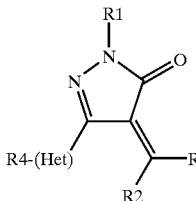
| Compound No. | R1 | R3 | R4-(Het) |
|---|---|---|---|
| 218 | —H | 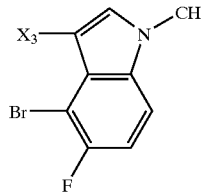 | 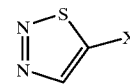 |
| 219 | —H | 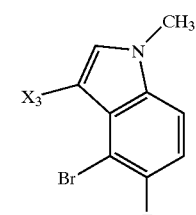 | 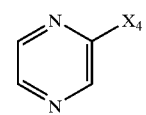 |
| 220 | —H | 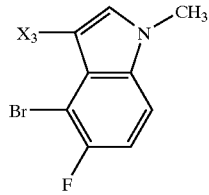 | 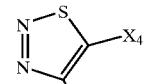 |
| 221 | —H | 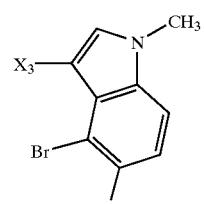 | 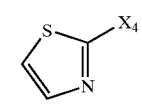 |
| 222 | —H | 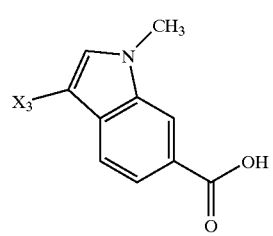 | 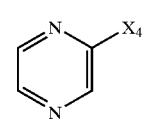 |
| 223 | —H | 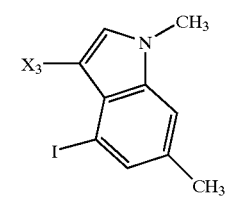 | 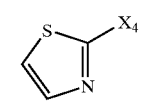 |

TABLE 1-continued
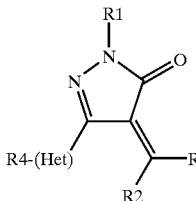
| Compound No. | R1 | R3 | R4-(Het) |
|---|---|---|---|
| 224 | —H | 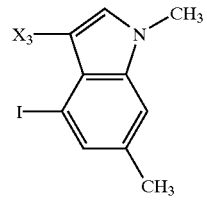 | 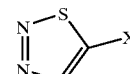 |
| 225 | —H | 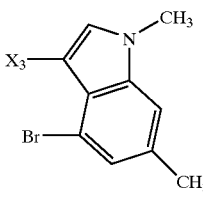 | 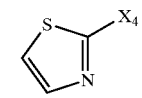 |
| 226 | —H | 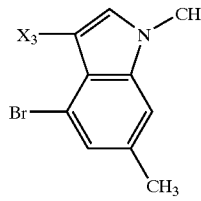 | 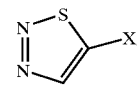 |
| 227 | —H | 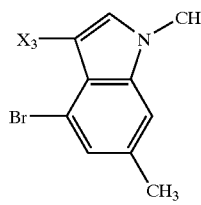 | 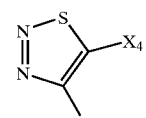 |
| 228 | —H | 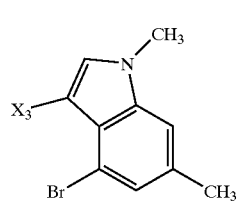 | 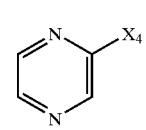 |
| 229 | —H | 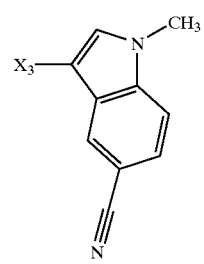 | 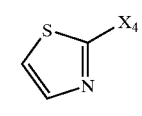 |

TABLE 1-continued
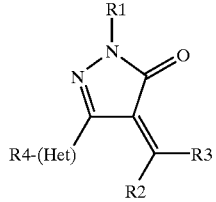
| Compound No. | R1 | R3 | R4-(Het) |
|---|---|---|---|
| 230 | —H |  | 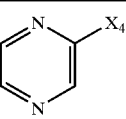 |
| 231 | —H | 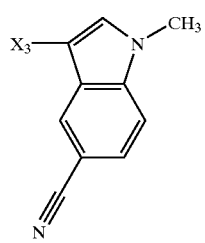 | 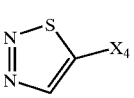 |
| 232 | —H | 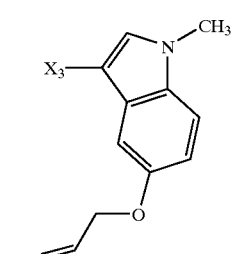 | 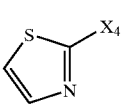 |
| 233 | —H | 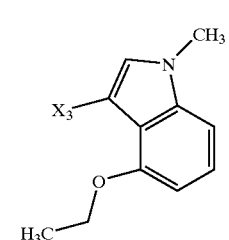 | 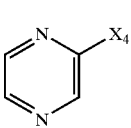 |
| 234 | —H | 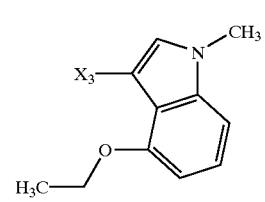 | 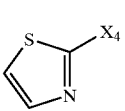 |
| 235 | —H | 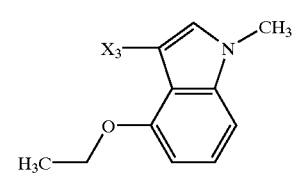 | 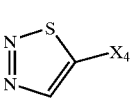 |

TABLE 1-continued
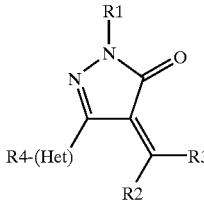
| Compound No. | R1 | R3 | R4-(Het) |
|---|---|---|---|
| 236 | —H | 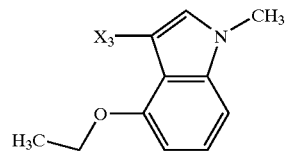 | 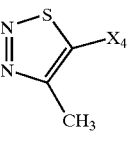 |
| 237 | —H | 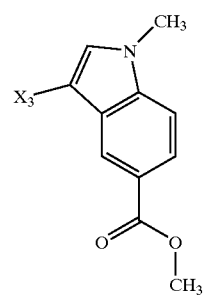 | 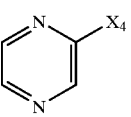 |
| 238 | —H | 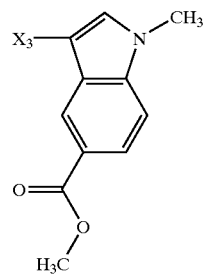 | 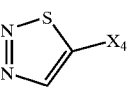 |
| 239 | —H | 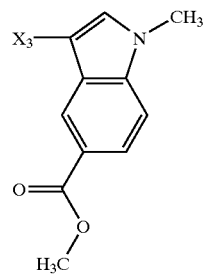 | 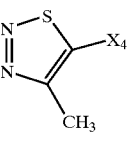 |
| 240 | —H | 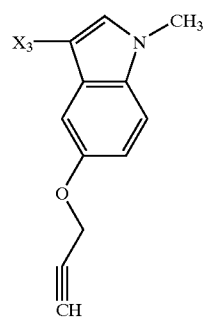 | 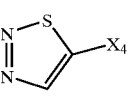 |

TABLE 1-continued
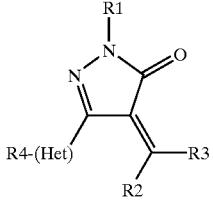
| Compound No. | R1 | R3 | R4-(Het) |
|---|---|---|---|
| 241 | —H | 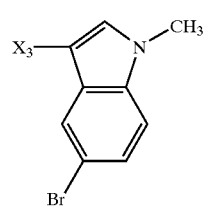 5-Br-1-methyl-indol-3-yl (X3) | 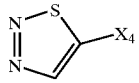 1,2,3-thiadiazol-5-yl (X4) |
| 242 | —H | 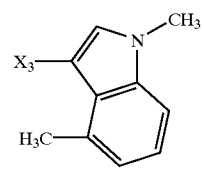 4-methyl-1-methyl-indol-3-yl (X3) | 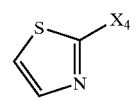 thiazol-2-yl (X4) |
| 243 | —H | 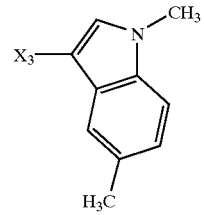 6-methyl-1-methyl-indol-3-yl (X3) | 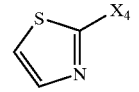 thiazol-2-yl (X4) |
| 244 | —H | 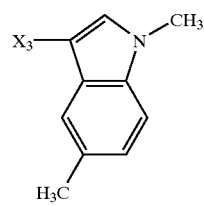 5-methyl-1-methyl-indol-3-yl (X3) | 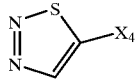 1,2,3-thiadiazol-5-yl (X4) |
| 245 | —H | 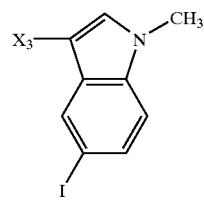 5-iodo-1-methyl-indol-3-yl (X3) | 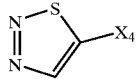 1,2,3-thiadiazol-5-yl (X4) |
| 246 | —H | 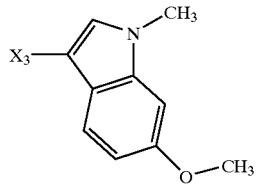 6-methoxy-1-methyl-indol-3-yl (X3) | 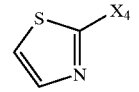 thiazol-2-yl (X4) |

TABLE 1-continued
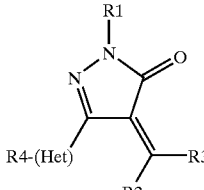
| Compound No. | R1 | R3 | R4-(Het) |
|---|---|---|---|
| 247 | —H | 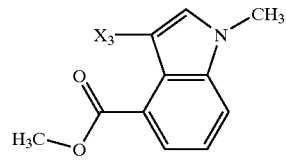 | 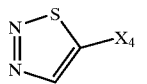 |
| 248 | —H | 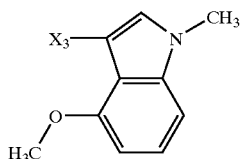 | 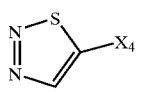 |
| 249 | —H | 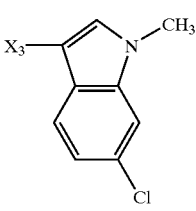 | 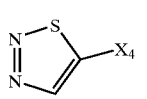 |
| 250 | —H | 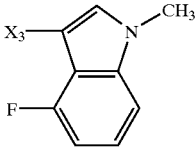 | 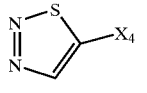 |
| 251 | —H | 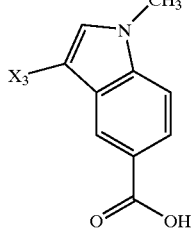 | 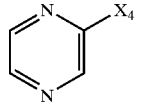 |
| 252 | —H | 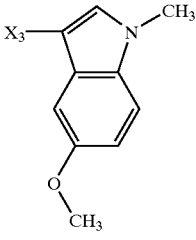 | 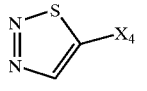 |

TABLE 1-continued
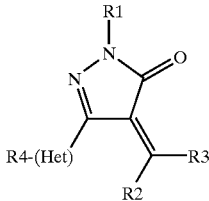
| Compound No. | R1 | R3 | R4-(Het) |
|---|---|---|---|
| 253 | —H | 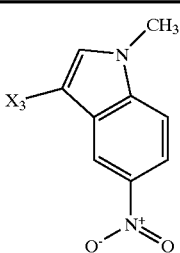 | 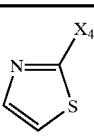 |
| 254 | —H | 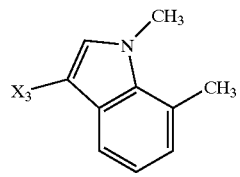 | 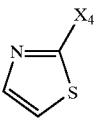 |
| 255 | —H | 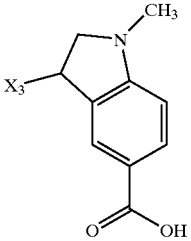 | 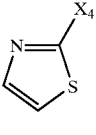 |
| 256 | —H | 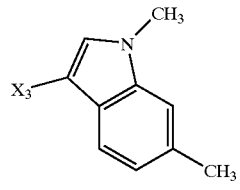 | 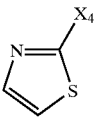 |
| 257 | —H | 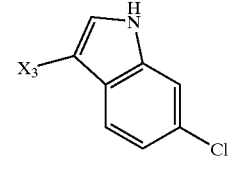 | 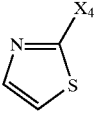 |
| 258 | —H | 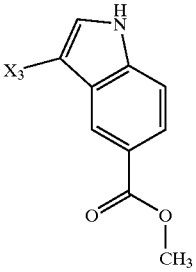 | 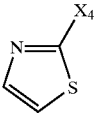 |

TABLE 1-continued
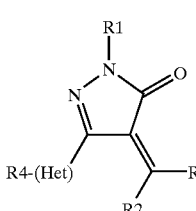
| Compound No. | R1 | R3 | R4-(Het) |
|---|---|---|---|
| 259 | —H | 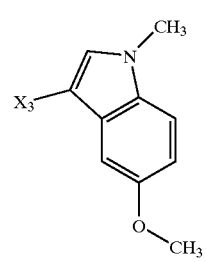 | 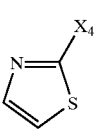 |
| 260 | —H | 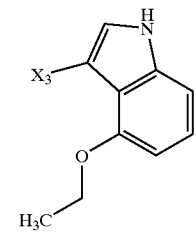 | 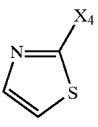 |
| 261 | —H | 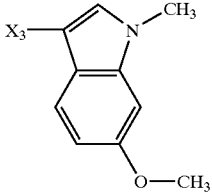 | 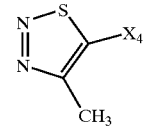 |
| 262 | —H | 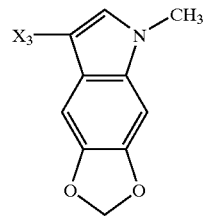 | 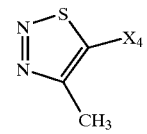 |
| 263 | —H | 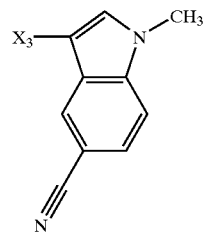 | 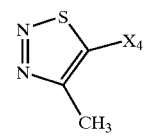 |

TABLE 1-continued
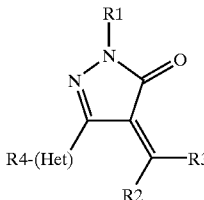
| Compound No. | R1 | R3 | R4-(Het) |
|---|---|---|---|
| 264 | —H | 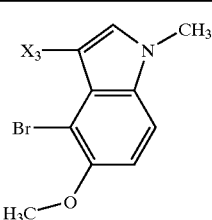 | 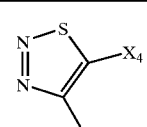 |
| 265 | —H | 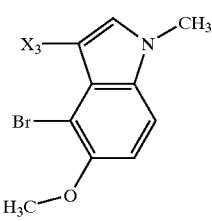 | 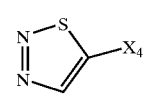 |
| 266 | —H | 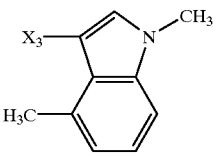 | 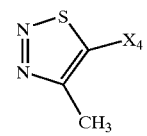 |
| 267 | —H | 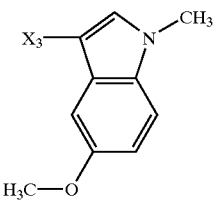 | 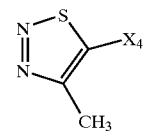 |
| 268 | —H | 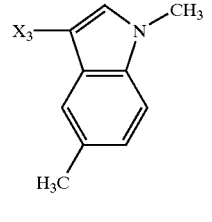 | 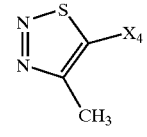 |
| 269 | —H | 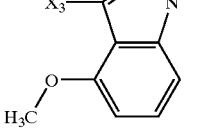 | 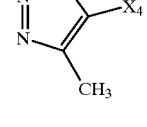 |

TABLE 1-continued
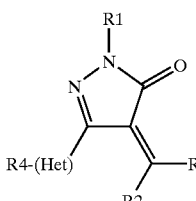
| Compound No. | R1 | R3 | R4-(Het) |
|---|---|---|---|
| 270 | —H | 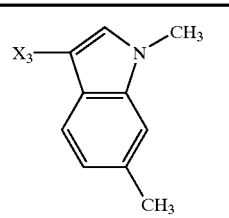 | 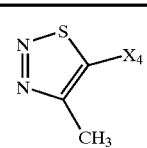 |
| 271 | —H | 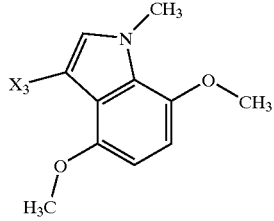 | 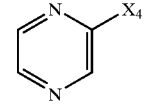 |
| 272 | —H | 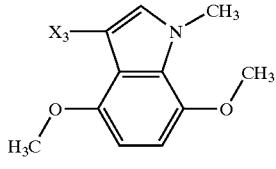 | 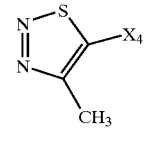 |
| 273 | —H | 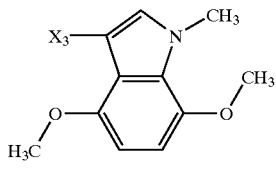 | 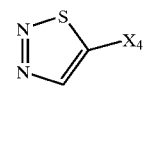 |
| 274 | —H | 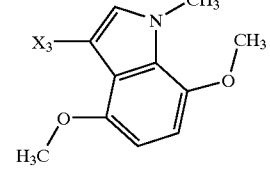 | 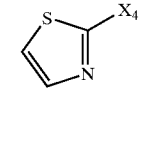 |
| 275 | —H | 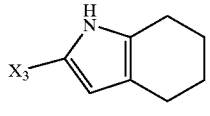 | 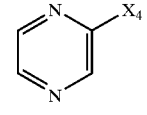 |
| 276 | —H | 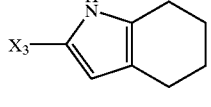 | 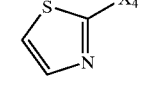 |

TABLE 1-continued
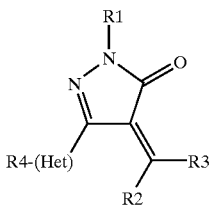
| Compound No. | R1 | R3 | R4-(Het) |
|---|---|---|---|
| 277 | —H | 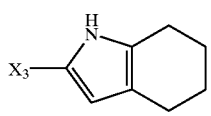 | 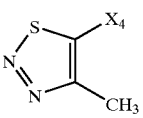 |
| 278 | —H | 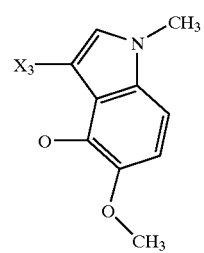 | 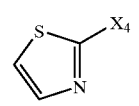 |
| 279 | —H | 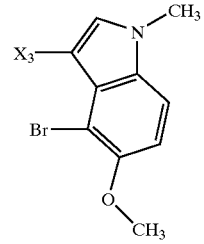 | 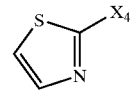 |
| 280 | —H | 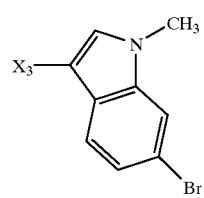 | 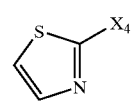 |
| 281 | —H | 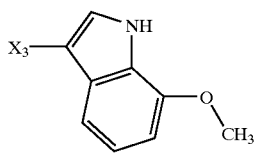 | 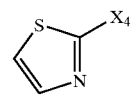 |
| 282 | —H | 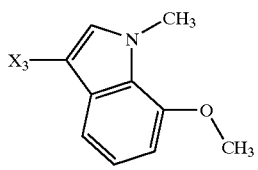 | 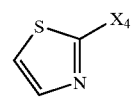 |

TABLE 1-continued
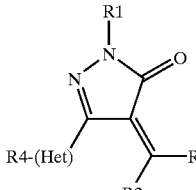
| Compound No. | R1 | R3 | R4-(Het) |
|---|---|---|---|
| 283 | —H | 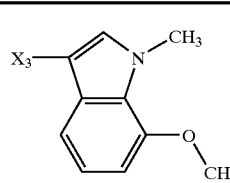 | 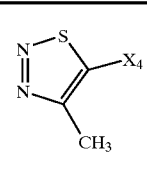 |
| 284 | —H | 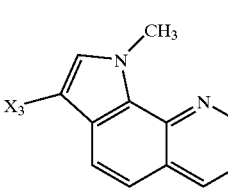 | 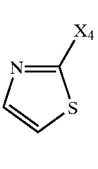 |
| 285 | —H | 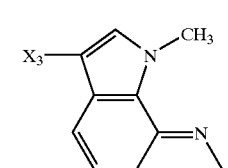 | 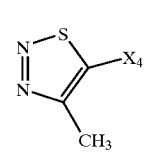 |
| 286 | —H | 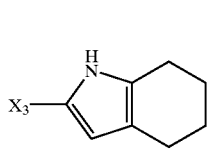 | 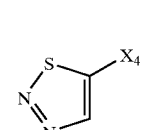 |
| 287 | —H | 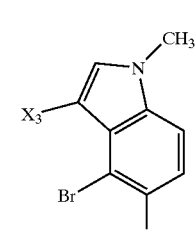 | 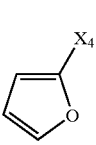 |
| 288 | —H | 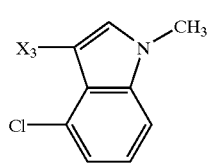 | 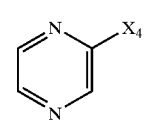 |

TABLE 1-continued
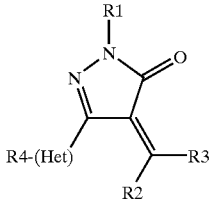
| Compound No. | R1 | R3 | R4-(Het) |
|---|---|---|---|
| 289 | —H | 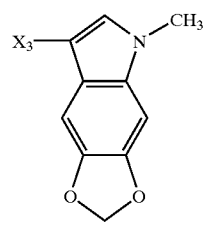 | 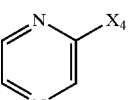 |
| 290 | —H | 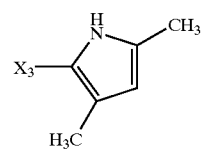 | 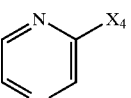 |
| 291 | —H | 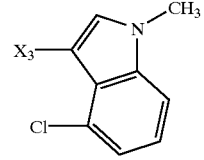 | 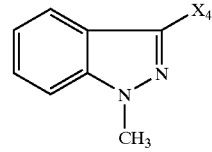 |
| 292 | —H | 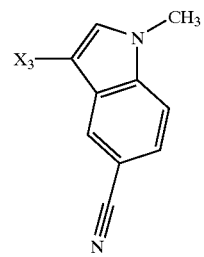 | 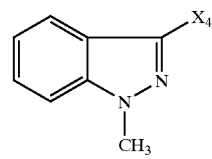 |
| 293 | —H | 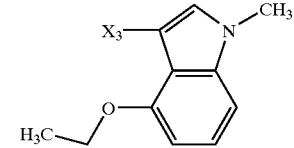 | 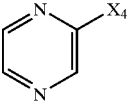 |
| 294 | —H | 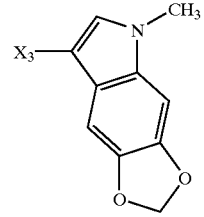 | 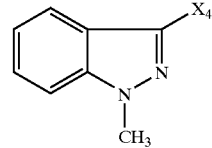 |

TABLE 1-continued
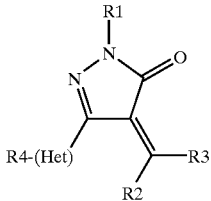
| Compound No. | R1 | R3 | R4-(Het) |
|---|---|---|---|
| 295 | —H | 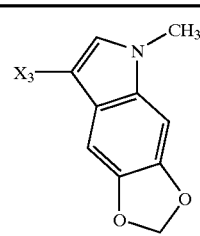 | 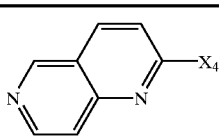 |
| 296 | —H | 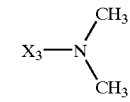 | 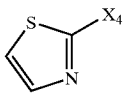 |
| 297 | —H | 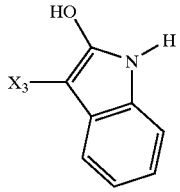 | 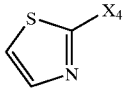 |
(a) $R_2$ and $R_3$ taken together represents the group show, i.e. R2 and R3 = [—CH2CH2—N(CH3)—CH2CH2—]
TABLE 1a
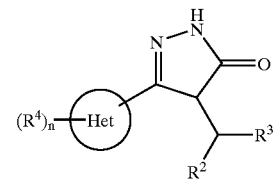
| Compound No. | R1 | R2 | R3 | R4-(Het) |
|---|---|---|---|---|
| 77 | —H | —H | 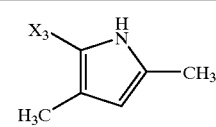 | 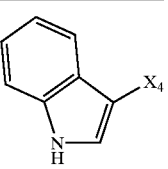 |
| 78 | —H | | 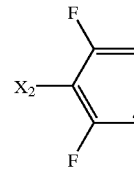 | 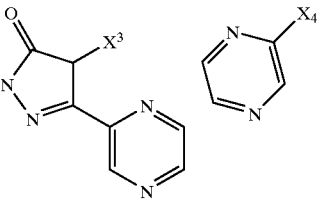 |

In Tables 1 and 1a the notations $X^1$, $X^2$, $X^3$, $X^4$ refers to the attachment point for substituents $R^1$, $R^2$, $R^3$, and $R^4$ respectively.

The compounds of Table 1 and 1a were characterized using Mass Spectroscopy (MS) and High Performance Liquid Chromatography (HPLC). The results are summarized in Table 2.

TABLE 2

| Compound No. | Mol. Wt. Calc. | Mol. Wt. Obs | HPLC Ret Time (min) | HPLC-Column and Gradient Conditions |
|---|---|---|---|---|
| 1 | 255 | 256 | 10.84 | A |
| 2 | 369 | 370 | 14.94 | A |
| 3 | 266 | 267 | 5.98 | A |
| 4 | 340 | 341 | 13.67 | B |
| 5 | 403 | 404 | 14.60 | B |
| 6 | 493 | 494 | 13.94 | B |
| 7 | 485 | 487 | 12.89 | B |
| 8 | 399 | 401 | 13.01 | B |
| 9 | 277 | 279 | 9.57 | B |
| 10 | 266 | 267 | 6.21 | A |
| 11 | 307 | 309 | 8.77 | B |
| 12 | 227 | 229 | 9.80 | A |
| 13 | 322 | 323 | 9.00 | A |
| 14 | 300 | 301 | 9.05 | A |
| 15 | 228 | 229 | 4.70 | A |
| 16 | 335 | 336 | 10.82 | A |
| 17 | 312 | 312 | 11.75 | A |
| 18 | 383 | 384 | 13.24 | A |
| 19 | 295 | 297 | 10.96 | A |
| 20 | 291 | 292 | 11.81 | A |
| 21 | 383 | 384 | 12.03 | A |
| 22 | 291 | 292 | 11.27 | A |
| 23 | 268 | 269 | 7.88 | B |
| 24 | 290 | 291 | 8.72 | B |
| 25 | 294 | 295 | 10.10 | B |
| 26 | 272 | 273 | 10.54 | B |
| 27 | 283 | 284 | 10.52 | B |
| 28 | 255 | 256 | 10.51 | B |
| 29 | 277 | 278 | 9.82 | B |
| 30 | 266 | 267 | 5.47 | B |
| 31 | 396 | 397 | 11.82 | A |
| 32 | 308 | — | 10.64 | A |
| 33 | 304 | — | 10.35 | A |
| 34 | 304 | — | 10.38 | A |
| 35 | 325 | 325 | 11.17 | A |
| 36 | 283 | 284 | 11.27 | B |
| 37 | 271 | 272 | 10.76 | B |
| 38 | 293 | 294 | 10.27 | B |
| 39 | 321 | 322 | 12.82 | B |
| 40 | 348 | 349 | 16.00 | B |
| 41 | 380 | 381 | 15.54 | B |
| 42 | 402 | 402 | 12.78 | B |
| 43 | 383 | 384 | 13.35 | A |
| 44 | 383 | 384 | 13.38 | A |
| 45 | 291 | 292 | 12.13 | A |
| 46 | 291 | 292 | 10.64 | B |
| 47 | 291 | 292 | 11.54 | A |
| 48 | 295 | 296 | 11.18 | A |
| 49 | 312 | 312 | 12.00 | A |
| 50 | 335 | 336 | 11.09 | A |
| 51 | 307 | 308 | 9.71 | B |
| 52 | 281 | 282 | 5.09 | B |
| 53 | 242 | 243 | 4.33 | B |
| 54 | 228 | 229 | 3.82 | B |
| 55 | 268 | 269 | 10.46 | B |
| 56 | 308 | 309 | 8.31 | B |
| 57 | 305 | 306 | 13.46 | B |
| 58 | 327 | 328 | 12.15 | B |
| 59 | 341 | 342 | 13.69 | B |
| 60 | 308 | 309 | 11.25 | B |
| 61 | 271 | 272 | 11.00 | B |
| 62 | 293 | 294 | 10.37 | B |
| 63 | 307 | 308 | 11.57 | B |
| 64 | 347 | 348 | 10.39 | B |
| 65 | 330 | 331 | 10.80 | A |
| 66 | 346 | 347 | 11.55 | A |
| 67 | 330 | 331 | 8.80 | A |
| 68 | 367 | 368 | 14.02 | A |
| 69 | 367 | 368 | 14.29 | A |
| 70 | 384 | 385 | 14.42 | A |
| 71 | 411 | 412 | 14.29 | A |
| 72 | 429 | 430 | 13.63 | B |
| 73 | 350 | 351 | 13.48 | B |
| 74 | 267 | 268 | 9.89 | B |
| 75 | 383 | 384 | 10.40 | B |
| 76 | 304 | 305 | 10.66 | B |
| 79 | 424 | 423, 425 | 4.92 | B |
| 80 | 317 | 318 | 13.95 | B |
| 81 | 353 | 354 | 10.77, 13.9 | B |
| 82 | 287 | 288 | 9.70 | B |
| 83 | 323 | 324 | 10.40 | B |
| 84 | 283 | 284 | 9.65 | B |
| 85 | 319 | 320 | 10.64 | B |
| 86 | 326 | 327 | 11.72 | B |
| 87 | 316 | 315 | 8.53 | A |
| 88 | 281 | 282 | 8.41 | B |
| 89 | 317 | 318 | 9.20 | B |
| 90 | 334 | 334, 336 | 10.36 | A |
| 91 | 273 | 273, 275 | 8.73 | B |
| 92 | 307 | 307, 309 | 9.36 | B |
| 93 | 298 | 299 | 7.91 | B |
| 94 | 298 | 299 | 7.73 | B |
| 95 | 256 | 257 | 8.02 | B |
| 96 | 373 | 374 | 10.2, 11.44 | A |
| 97 | 341 | 342 | 11.79 | A |
| 98 | 254 | 255 | 6.59 | B |
| 99 | 299 | 300 | 6.32 | B |
| 100 | 299 | 300 | 7.11 | B |
| 101 | 318 | 319 | 9.08 | B |
| 102 | 281 | 282 | 10.70 | B |
| 103 | 317 | 318 | 11.13 | B |
| 104 | 358 | 358, 360 | 11.53 | B |
| 105 | 343 | 343, 345 | 12.62 | B |
| 106 | 309 | 310 | 11.47 | B |
| 107 | 326 | 326 | 12.33 | B |
| 108 | 309 | 310 | 8.55 | B |
| 109 | 325 | 326 | 11.87 | B |
| 110 | 342 | 342, 344 | 12.74 | B |
| 111 | 325 | 326 | 11.90 | B |
| 112 | 342 | 342, 344 | 12.76 | B |
| 113 | 326 | 327 | 10.36 | B |
| 114 | 341 | 342 | 9.40 | B |
| 115 | 366 | 367 | 10.74 | B |
| 116 | 381 | 382 | 9.18 | B |
| 117 | 398 | 399 | 12.03 | B |
| 118 | 435 | 435 | 15.99 | B |
| 119 | 303 | 304 | 9.62 | B |
| 120 | 321 | 322 | 10.16 | B |
| 121 | 361 | 362 | 10.12 | B |
| 122 | 266 | 267 | 8.11 | B |
| 123 | 284 | 285 | 7.66 | B |
| 124 | 245 | 246 | 2.49 | B |
| 125 | 244 | 245 | 7.54 | B |
| 126 | 306 | 307 | 9.27 | B |
| 127 | 328 | 329 | 10.03 | B |
| 128 | 338 | 338, 340 | 11.81 | B |
| 129 | 321 | 322 | 10.97 | B |
| 130 | 333 | 334 | 10.97, 13.14 | B |
| 131 | 333 | 334 | 10.35 | B |
| 132 | 322 | 323 | 12.01 | B |
| 133 | 382 | 382, 384 | 12.21 | B |
| 134 | 321 | 322 | 10.80 | B |
| 135 | 254 | 255 | 3.90 | B |
| 136 | 316 | 317 | 8.65 | B |
| 137 | 326 | 327 | 11.51 | B |
| 138 | 317 | 318 | 11.34 | B |

TABLE 2-continued

| Compound No. | Mol. Wt. Calc. | Mol. Wt. Obs | HPLC Ret Time (min) | HPLC-Column and Gradient Conditions |
|---|---|---|---|---|
| 139 | 347 | 348 | 10.49 | B |
| 140 | 333 | 334 | 10.44 | B |
| 141 | 338 | 338, 340 | 11.59 | B |
| 142 | 338 | 339 | 11.26 | B |
| 143 | 343 | 343, 345 | 12.21 | B |
| 144 | 352 | 353 | 11.25 | B |
| 145 | 317 | 318 | 11.50 | B |
| 146 | 317 | 318 | 11.61 | B |
| 147 | 363 | 364 | 9.29 | B |
| 148 | 352 | 352, 354 | 12.66 | B |
| 149 | 364 | 364, 366 | 13.00 | B |
| 150 | 317 | 318 | 11.44 | B |
| 151 | 304 | 305 | 8.70 | B |
| 152 | 371 | 372 | 12.72 | B |
| 153 | 275 | 276 | 11.50 | A |
| 154 | 275 | 276 | 11.52 | A |
| 155 | 357 | 358 | 11.04 | B |
| 156 | 333 | 334 | 10.67 | B |
| 157 | 338 | 338, 340 | 12.16 | B |
| 158 | 382 | 382, 384 | 12.47 | B |
| 159 | 382 | 382, 384 | 11.72 | B |
| 160 | 429 | 430 | 12.68 | B |
| 161 | 409 | 410 | 12.94 | B |
| 162 | 339 | 340 | 11.44 | B |
| 163 | 343 | 343, 345 | 13.14 | B |
| 164 | 344 | 345 | 12.17 | B |
| 165 | 409 | 410 | 15.11 | B |
| 166 | 414 | 415 | 15.41 | B |
| 167 | 331 | 332 | 11.27 | B |
| 168 | 352 | 352, 354 | 11.66 | B |
| 169 | 396 | 396, 398 | 11.57 | B |
| 170 | 378 | 379 | 11.83 | B |
| 171 | 303 | 304 | 10.60 | B |
| 172 | 402 | 402, 404 | 12.18 | B |
| 173 | 341 | 342 | 11.48 | B |
| 174 | 309 | 310 | 9.76 | B |
| 175 | 344 | 342, 344 | 10.21 | B |
| 176 | 345 | 345, 347 | 12.39 | A |
| 177 | 387 | 387, 389 | 13.21 | A |
| 178 | 295 | 296 | 10.20 | A |
| 179 | 369 | — | 11.52 | A |
| 180 | 349 | 350 | 10.84 | A |
| 181 | 383 | 384 | 11.05, 7.82 | B |
| 182 | 398 | 399 | 10.57 | B |
| 183 | 327 | 328 | 10.52 | B |
| 184 | 281 | 282 | 11.47 | C |
| 185 | 317 | 318 | 12.06 | C |
| 186 | 344 | 344, 346 | 11.45 | B |
| 187 | 358 | 358, 359 | 12.31 | A |
| 188 | 374 | 374, 376 | 11.54 | A |
| 189 | 352 | 352, 354 | 13.58 | C |
| 190 | 352 | 353 | 9.43 | C |
| 191 | 370 | 371 | 9.83 | C |
| 192 | 391 | 392 | 11.73 | B |
| 193 | 388 | 388, 390 | 11.53 | B |
| 194 | 345 | 346 | 11.02 | B |
| 195 | 344 | 344, 346 | 11.35 | B |
| 196 | 323 | 324 | 11.17 | B |
| 197 | 431 | 431, 433 | 9.44 | C |
| 198 | 464 | 464, 466 | 13.17 | B |
| 199 | 459 | 460 | 11.72 | B |
| 200 | 348 | 349 | 10.85 | B |
| 201 | 323 | 324 | 10.94 | B |
| 202 | 379 | 380 | 12.13 | B |
| 203 | 412 | 412, 414 | 11.62 | B |
| 204 | 316 | 317 | 8.79 | B |
| 205 | 434 | 434, 436 | 14.97 | C |
| 206 | 373 | 374 | 14.37 | C |
| 207 | 355 | 356 | 13.84 | C |
| 208 | 319 | 320 | 13.41 | C |
| 209 | 353 | 354 | 10.14 | B |
| 210 | 348 | 349 | 9.98 | B |
| 211 | 361 | — | 9.40 | B |
| 212 | 464 | — | 13.28 | B |
| 213 | 467 | 468 | 12.74 | A |
| 214 | 447 | 448 | 12.94 | B |
| 215 | 379 | 380 | 14.79 | A |
| 216 | 443 | 444 | 12.84 | C |
| 217 | 463 | 464 | 14.22 | C |
| 218 | 406 | 406, 408 | 11.95 | C |
| 219 | 400 | 400, 402 | 11.53 | C |
| 220 | 420 | 420, 422 | 12.18 | C |
| 221 | 405 | 405, 407 | 13.24 | C |
| 222 | 347 | 348 | 8.43 | C |
| 223 | 448 | — | 12.37, 14.41 | C |
| 224 | 449 | — | 13.47 | C |
| 225 | 401 | 401, 403 | 14.27 | C |
| 226 | 402 | 402, 404 | 13.35 | C |
| 227 | 416 | 416, 418 | 13.54 | C |
| 228 | 396 | 396, 398 | 12.80 | C |
| 229 | 333 | 334 | 10.90 | B |
| 230 | 317 | 318 | 8.02 | B |
| 231 | 334 | 335 | 9.89 | B |
| 232 | 362 | 363 | 11.64 | B |
| 233 | 347 | 348 | 11.28 | B |
| 234 | 352 | 353 | 12.49 | B |
| 235 | 353 | 354 | 11.72 | B |
| 236 | 367 | 368 | 11.60 | B |
| 237 | 361 | 362 | 10.49 | B |
| 238 | 367 | 368 | 10.12 | B |
| 239 | 381 | 382 | 10.28 | B |
| 240 | 363 | 364 | 10.94 | B |
| 241 | 388 | 388, 390 | 11.85 | B |
| 242 | 322 | 323 | 12.83 | B |
| 243 | 322 | 323 | 12.75 | C |
| 244 | 323 | 324 | 11.11 | B |
| 245 | 435 | 436 | 11.95 | B |
| 246 | 338 | 339 | 11.39 | B |
| 247 | 367 | 368 | 10.82 | B |
| 248 | 339 | 340 | 11.12 | C |
| 249 | 344 | 344, 346 | 12.02 | C |
| 250 | 327 | 328 | 10.97 | C |
| 251 | 347 | 348 | 8.00 | C |
| 252 | 339 | 340 | 10.50 | C |
| 253 | 353 | 354 | 12.00 | C |
| 254 | 322 | 323 | 12.68 | C |
| 255 | 352 | 353 | 9.21 | C |
| 256 | 322 | 323 | 12.89 | C |
| 257 | 329 | 329, 331 | 12.31 | C |
| 258 | 352 | 353 | 10.64 | C |
| 259 | 338 | 339 | 11.45 | C |
| 260 | 338 | 339 | 11.20 | C |
| 261 | 353 | 354 | 10.51 | C |
| 262 | 367 | 368 | 10.45 | C |
| 263 | 348 | 349 | 10.22 | C |
| 264 | 432 | 432, 434 | — | — |
| 265 | 418 | 418, 420 | 11.45 | C |
| 266 | 337 | 338 | 11.16 | C |
| 267 | 353 | 354 | 10.49 | C |
| 268 | 337 | 338 | 11.39 | C |
| 269 | 353 | 354 | 11.12 | C |
| 270 | 337 | 338 | 11.72 | C |
| 271 | 363 | 364 | 11.19 | C |
| 272 | 383 | 384 | 12.54 | C |
| 273 | 369 | 370 | 12.49 | C |
| 274 | 368 | 369 | 12.61 | C |
| 275 | 293 | 294 | 11.38 | C |
| 276 | 298 | 299 | 12.86 | C |
| 277 | 313 | 314 | 11.68 | C |
| 278 | 464 | 465 | 12.09 | B |
| 279 | 417 | 417, 419 | 11.86 | B |
| 280 | 387 | 387, 389 | 13.08 | B |
| 281 | 324 | 325 | 11.10 | C |
| 282 | 338 | 339 | 12.41 | B |
| 283 | 353 | 354 | 11.42 | B |
| 284 | 359 | 360 | 13.73 | C |

TABLE 2-continued

| Compound No. | Mol. Wt. Calc. | Mol. Wt. Obs | HPLC Ret Time (min) | HPLC-Column and Gradient Conditions |
|---|---|---|---|---|
| 285 | 374 | 375 | 12.38 | C |
| 286 | 299 | 300 | 11.20 | C |
| 287 | 388 | 388 | 12.80 | C |
| 288 | 338 | 338, 340 | 9.71 | C |
| 289 | 347 | 348 | 8.42 | C |
| 290 | 267 | 268 | 7.78 | C |
| 291 | 390 | 390 | 14.95 | C |
| 292 | 380 | 381 | 13.67 | C |
| 293 | 347 | 348 | 9.70 | C |
| 294 | 399 | 400 | 13.68 | C |
| 295 | 397 | 398 | 7.81 | C |
| 296 | 222 | 223 | 5.01 | A |
| 297 | 310 | 311 | 11.19 | A |

Method A—Zorbax C8, 10% AcCN 90% $H_2O$; 100% AcCN over 20 min at 1.6 mL/min on HP 1100.
Method B—Zorbax C8, 10% AcCN 90% $H_2O$; 100% AcCN over 20 min at 1.6 mL/min on HP 1050.
Method C—Zorbax C8, 10% AcCN 90% $H_2O$; 100% AcCN over 20 min at 1.6 mL/min on HP 1090.

Example 12

Preparation of 4-[(1-methylindol-3-yl)methylene]-3-(4-(2-naphthyl)(1,3-thiazol-2-yl))-2-pyrazolin-5-one (Compound 118)

(a) Preparation of 3-(4-(2-naphthyl)-1,3-thiazol-2-yl)-2-pyrazolin-5-one, (VIg)

A mixture of bromoethyl-2-naphthyl ketone (1.78 g, 6.8 mmol), 2-thio-oxalamic acid ethyl ester (1 g, 7.5 mmol) in EtOH (absolute) was kept under reflux for 6 h. The mixture was cooled to room temperature. The product separated as a solid, which was filtered, washed with ethanol and dried to provide the desired ester, ethyl 4-(2-naphthyl)-1,3-thiazole-2-carboxylate, (IIIb) (0.862 g, 48% yield). MS: 284 (M+H). To a mixture of the ester, (IIIb) (800 mg, 2.82 mmol) in dry methylacetate (10 mL) was added NaH (60% dispersion in mineral oil, 135 mg, 3.37 mmol). The mixture was stirred at room temperature for 0.5 h and at reflux for 2 h. The mixture was poured into cold water and was neutralized with conc. HCl. After saturating the mixture with NaCl, the mixture was extracted from dichloromethane (twice). The combined extract was washed with brine. After drying over magnesium sulphate, solvent was evaporated to furnish the β-ketoester, ethyl 3-(4-(2-naphthyl)(1,3-thiazol-2-yl))-3-oxopropanoate, which was used for the next step without further purification. To the above β-ketoester was added absolute ethanol (10 mL) and hydrazine hydrate (1 mL, excess). The mixture was kept under reflux for 4 h. After cooling, solvent was evaporated from the reaction mixture. The resulting mixture was chromatographed over silica gel and was eluted with EtOAc. The product pyrazolone (VIg) was isolated as a solid which was further purified via washing with diethyl ether (i.e. stirring in ~50 mL of diethyl ether followed by filtration and washing with diethyl ether). Yield 287 mg, (35% in two steps). MS: 294 (M+H).

(b) Preparation of Compound 118

A mixture of the pyrazolone (VIg) (50 mg, 0.17 mmol), indole-3-carboxaldehyde (30 mg, 0.19 mmol) in absolute ethanol (1 mL) along with 2–3 drops of piperidine was stirred at 80–90° C. for 3 h. The product that separated as a solid was filtered and washed with ethanol. After drying, 52 mg of the compound 118 was isolated as a single geometrical isomer.

Example 13

Preparation of 4-[(5-methy(2H-1,3-dioxoleno[4,5-f]indol-7-yl))methylene]-3-(1,3-thiazol-2-yl)-2-pyrazolin-5-one (Compound 144)

(a) Preparation of 5,6-methylenedioxy-1-methyl-indole-3-carboxaldehyde:

To an ice cold solution of DMF (50 mL, excess) was added $POCl_3$ (8 mL, 85.7 mmol) in a drop wise fashion. After addition the mixture was stirred at 0° C. for 5 min and at room temperature for 45 min. The mixture was cooled to 0° C. and 5,6-methylenedioxy-indole (10 g, 62.1 mmol) was added in portion. After complete addition, the mixture was stirred at 0° C. for 10 min and at room temperature for 20 min and finally at 60° C. for 6 h. The mixture was cooled to room temperature and then to 0° C. followed by the addition of 1N NaOH solution (150 mL). The mixture was stirred at room temperature for 30 min as result a homogenous solution was obtained. To the mixture was added 100 mL of water and stirring was continued at room temperature overnight. The product, 5,6-methylenedioxy-indole-3-carboxaldehyde separated as a solid, which was filtered, washed (water followed by hexane) and dried. The filtrate also provided additional product upon extraction from ethyl acetate (3 times). The combined organic extractions were washed successively with water and brine. After drying over $MgSO_4$, solvent was evaporated. A solid was obtained which was suspended in 100 mL of diethyl ether, sonicated for few minutes and was filtered. The solid was further washed with diethyl ether and was dried. A combined crude yield of 8.08 g (69%) of the 5,6-methylenedioxy-indole-3-carboxaldehyde was obtained which was subjected to N-methylation without further purifications. To a cold (0° C.) solution of 5,6-methylenedioxy-indole-3-carboxaldehyde (see above) (8 g, 42.32 mmol) in dry DMF (40 mL) was added NaH (60% dispersion in mineral oil, 2.1 g, 52.5 mmol). The resulting mixture was stirred at 0° C. for 30 min. Iodomethane (5 mL, 80.3 mmol) was added dropwise to the reaction mixture. The mixture was stirred at 0° C. for 15 min and at room temperature for 2 h. The mixture was cooled to 0° C. and was quenched with water. The mixture was further diluted with water (~700 mL). The product, 5,6-methylenedioxy-1-methyl-indole-3-carboxaldehyde separated as a solid which was filtered, washed (water followed by hexane) and dried to provide 6.2 g (72% yield) of the desired product. MS: 204 (M+H).

(b) Preparation of Compound 144

A mixture of the pyrazolone (VIa) (0.030 g, 0.17 mmol), 5,6-methylenedioxy-N-methyl-indole-3-carboxaldehyde (0.040 g, 0.197 mmol) and ethanol (2 mL) in the presence of 2–3 drops of piperidine was heated to ~85° C. for about 1 h when a yellow-orange solid began to appear. The mixture cooled in ice bath and solid was filtered off, washed with ethanol and dried to provide the compound 144 (54 mg, 90% yield) as a yellow-orange solid.

Example 14

Preparation of 4-[(4-chloro-1-methylindol-3-yl)methylene]-3-pyrazin-2-yl-2-pyrazolin-5-one (Compound 189)

(a) Preparation of 3-pyrazin-2-yl-2-pyrazolin-5-one, (VIh)

A slurry of ethyl pyrazine-2-carboxylate (10 g, 66 mmol), in methyl acetate (40 mL) and NaH (60% dispersion in mineral oil, 3.7 g, 97 mmol, 1.47 equiv.) was refluxed for an hour. The reaction mixture was cooled to room temperature, neutralized with acetic acid and extracted with ethyl acetate. The solvent was evaporation to yield the β-ketoester (Vc) (6.35 g) as an off-white solid. [MS: 179, (M–H)]. A mixture of the ester (Vc) (0.5 g, 2.8 mmol), methyl hydrazine (0.16 g, 3.4 mmol) in ethanol (3 mL) was refluxed overnight. The resulting precipitate was filtered to provide the pyrazolone (VIh) as an orange solid (0.3 g, 1.7 mmol).

(b) Preparation of Compound 189

A mixture of the pyrazolone (VIh) (0.035 g, 0.2 mmol), piperidine (0.01 mmol), ethanol (1 mL), and 4-chloro-1-methylindole-3-carboxaldehyde (0.046 g, 0.24 mmol) was refluxed. The resulting precipitates were filtered to obtain compound 189 as a bright orange solid (0.036 g, 0.10 mmol).

Example 15

Preparation of 3-[5-(dimethylamino)(1,3,4-thiadiazol-2-yl)]-4-[(1-methylindol-3-yl)methylene]-2-pyrazolin-5-one (Compound 190)

(a) Preparation of the 3-[5-dimethylamino)-1,3,4-thiadiazol-2-yl]-2-pyrazolin-5-one (VIi)

A solution of 4,4-dimethyl-3-thiosemicarbazide (2.0 g, 16.8 mmol) and ethyl chloro-oxo-acetate (2.3 g, 16.8 mmol) were mixed under an inert atmosphere and cooled to 0° C. in an ice bath. Sulfuric acid (2 mL) was added slowly. After the effervescence ceased, the ice bath was removed and the reaction was allowed to warm to room temperature and stirred for 3 hours. To the white heterogeneous mixture, ethyl acetate (100 mL) was added and the organic layer was washed twice with 2% sodium bicarbonate solution and brine. The organic layer was dried over anhydrous magnesium sulfate and evaporated. The residual solid was dissolved in ethyl acetate and the desired compound was precipitated with ether to yield the ethyl 5-(dimethylamino)-1,3,4-thiadiazole-2-carboxylate (IIIc) (1.9 g, 9.4 mmol). The ester, (IIIc) was dissolved in anhydrous methyl acetate (4 mL) and solution purged with an inert atmosphere. To this yellow solution sodium hydride (60% dispersion in mineral oil, 0.53 g, 13.25 mmol) was added providing a light yellow precipitate. The reaction mixture was then heated to 65° C. and it turned to a light green precipitate. Additional methyl acetate (4 mL) was added and in ten minutes the reaction mixture became a tan solid. The reaction was removed from the heat and an additional methyl acetate (20 mL) was added. The mixture was neutralized with acetic acid. The solid was filtered off and the filtrate was evaporated. The solid from the filtrate was washed with ether to yield the desired β-ketoester, ethyl 3-[5-(dimethylamino)(1,3,4-thiadiazol-2-yl)]-3-oxopropanoate, (Vd) (5.2 mmol) as a yellow solid. A mixture of the β-ketoester (Vd) (1.2 g, 1.31 mmol), ethanol (2 mL) and hydrazine hydrate (0.063 g, 1.96 mmol) was heated to 65° C. for two hours. The precipitate was filtered to obtain the pyrazolone (VIi) (0.075 g, 0.36 mmol) as a light yellow solid.

(b) Preparation of Compound 190

A mixture of the pyrazolone (VIi) (0.035 g, 0.166 mmol), 1-methyl indole-3-carboxaldehyde (0.032 g, 0.2 mmol) and ethanol (1 mL) was heated to 65° C. and stirred overnight. The orange precipitate that formed was filtered to obtain compound 190 (0.024 g, 0.068 mmol).

Example 16

Preparation of 4-[(1-methyl-4-phenylindol-3-yl)methylene]-3-pyrazin-2-yl-2-pyrazolin-5-one (Compound 202)

(a) Preparation of the 4-phenyl-1-methyl-indole-3-carboxaldehyde

To an ice cold solution of DMF (5 mL, excess) was added POCl$_3$ (0.8 mL, 8.57 mmol) in a drop wise fashion. After addition the mixture was stirred at 0° C. for 5 min and at room temperature for 45 min. The mixture was cooled to 0° C. and 4-bromoindole (1 g) was added in portion. After complete addition, the mixture was stirred at 0° C. for 10 min and at room temperature for 20 min and finally at 60° C. for 6 h. The mixture was cooled to room temperature and then to 0° C. followed by the addition of 1N NaOH solution (15 mL). The mixture was stirred at room temperature for 30 min, when a solid was formed during the aqueous work up, which did not go into solution up on brief warming. The solid was filtered, washed with and dried to yield 0.77 g of the product, which was subjected to N-methylation without further purifications.

To a cold solution (0° C.) of 4-bromo-indole-3-carboxaldehyde (0.767 g, 3.4 mmol) in dry DMF (2 mL) was added NaH (60% dispersion in mineral oil, 173 mg, 4.37 mmol). The resulting mixture was stirred at 0° C. for 20 min. Iodomethane (0.8 mL, excess) was added to the reaction mixture in a drop wise fashion. The cooling bath was removed and the resulting mixture was stirred at room temperature for 1.5 h. The mixture was quenched with water and was extracted repeatedly from EtOAc. The combined organic extracts were washed with water (twice) and brine. After drying over magnesium sulfate, solvent was removed. The resulting solid was taken in hexane and sonicated for 30 min, filtered to provide the product, 4-bromo-1-methyl-indole-3-carboxaldehyde (0.687 g, 85% yield). A mixture of 4-bromo-1-methyl-indole-3-carboxaldehyde (109 mg, 0.45 mmol), phenyl boronic acid (85 mg, 0.69 mmol) in DMF (4 mL) was degassed (argon). To the mixture was added bis(triphenylphosphine)-palladium II chloride (25 mg, 0.035 mmol) followed by addition of 2M Na$_2$CO$_3$ solution (2 mL, 4 mmol) and the mixture was stirred under argon at 100° C. for 18.5 h and then at reflux for 3 h. The mixture was cooled to room temperature. The reaction mixture was diluted with water and extracted repeatedly with ethyl acetate. The combined extract was washed with water (twice) and brine. After drying over anhydrous magnesium sulfate, solvent was removed in vacuo and the crude product was purified by flash chromatography (hexane:EtOAc 1:1). The desired product was isolated as syrup (79% yield). MS: 236, 238.

(b) Preparation of Compound 202

A mixture of the pyrazolone (VIe) (40 mg, 0.24 mmol), 4-phenyl-1-methyl-indole-3-carboxaldehyde (84 mg, 0.35 mmol) in absolute ethanol (2 mL) along with 2–3 drops of piperidine was stirred at 80–90° C. for 2 h. The product that separated as a solid was filtered and washed with ethanol. After drying, 81 mg of the compound 202 was isolated as a single geometrical isomer.

Example 17

Preparation of 4-[(4-bromo-1-methylindol-3-yl)methylene]-3-(1-methyl(1H-indazol-3-yl))-2-pyrazolin-5-one (Compound 205)

(a) Preparation of the 3-(1-methyl-1H-indazol-3-yl)-2-pyrazolin-5-one, (VIj)

A mixture of indazole-3-carboxylic acid (5 g, 31 mmol), chlorotrimethylsilane (34 g, 310 mmol), and methanol (50 mL) was allowed to stir overnight. The solvent was evaporated to obtain a yellow product (4 g, 74% yield). A slurry of the methyl ester (4 g, 23 mmol), NaH (1.3 g, 35 mmol), iodomethane (33 g, 230 mmol), and THF (60 mL) was mixed overnight. The mixture was neutralized and extracted with ethyl acetate. The desired product (IIId) was collected as a yellow solid (4 g, 21 mmol). A slurry of the ester (IIId) (4 g, 21 mmol), NaH (1.2 g, 32 mmol), and methyl acetate (40 mL) was refluxed for four hours. The mixture was neutralized with acetic acid and the product was extracted with ethyl acetate, concentrated in vacuo to provide the desired β-ketoester, ethyl 3-(1-methyl(1H-indazol-3-yl))-3-oxopropanoate, (Ve) as an orange gum (4.6 g). A mixture of β-ketoester (Ve) (4.6 g, 20 mmol), hydrazine hydrate (0.77 g, 24 mmol), and ethanol (10 mL) was refluxed overnight. The resulting precipitate was filtered to obtain the pyrazolone (VIj) as a white solid (1.2 g, 30% yield).

(b) Preparation of Compound 205

A mixture of the pyrazolone (VIj) (0.043 g, 0.2 mmol), 4-bromo-1-methylindole-3-carboxaldehyde (0.052 g, 0.22 mmol), piperidine (0.01 mmol) and ethanol (1 mL) was refluxed for 3.5 h. The resulting precipitate was filtered to obtain a bright orange solid (0.052 g, 60% yield).

Example 18

Preparation of 4-[(4-iodo-1,6-dimethylindol-3-yl) methylene]-3-(1,3-thiazol-2-yl)-2-pyrazolin-5-one Compound (223)

(a) Preparation of 6-methyl-4-iodo-indole-3-carboxaldehyde

A solution of thallium (III) trifluoroacetate (1 g, 1.84 mmol) in trifluoroacetic acid (15 mL) was added to 6-methyl-indole-3-carboxaldehyde (200 mg, 1.25 mmol) and the resulting mixture was stirred at 30° C. for 2 h. The solvent was removed under vacuum (rotary evaporator). To the residue was added an aqueous solution of potassium iodide (2 g, 12 mmol, in 20 mL of water) and the mixture was stirred at room temperature overnight. Solid sodium meta-bisulfite was added to the reaction mixture until it turned yellow. The mixture was basified with aqueous NaOH solution and was extracted repeatedly from diethyl ether. The combined organic was washed with brine and was dried over magnesium sulfate. Evaporation of solvent gave the crude product, which was purified by flash chromatography by using EtOAc as eluent. The product, 6-methyl-4-iodo-indole-3-carboxaldehyde was isolated as solid to yield 283 mg (79%) of the desired product. MS: 286.

(b) Preparation of 1,6-dimethyl-4-iodo-indole-3-carboxaldehyde

To a cold solution (0° C.) of 6-methyl-4-iodo-indole-3-carboxaldehyde (265 mg, 0.92 mmol) in dry DMF (2 mL) was added NaH (60% dispersion in mineral oil, 50 mg, 1.25 mmol). The resulting mixture was stirred at 0° C. for 20 min. Iodomethane (0.5 mL, excess) was added to the reaction mixture in a drop wise fashion. The cooling bath was removed and the resulting mixture was stirred at room temperature for 1.5 h. The mixture was quenched with water and was extracted repeatedly from EtOAc. Combined organic was washed with water (twice) and brine. After drying over magnesium sulfate, solvent was removed. The product, 1,6-dimethyl-4-iodo-indole-3-carboxaldehyde was obtained as a solid was which was suspended in hexane, stirred for few minutes and was filtered. The product was further washed with more hexane and was dried to yield 213 mg (77%) of the desired product. MS: 300 (M+H), 322 (M+Na).

(c) Preparation of Compound 223

A mixture of the pyrazolone (VIa) (0.010 g, 0.059 mmol), 1,6-dimethyl-4-iodo-indole-3-carboxaldehyde (0.020 g, 0.06 mmol) and ethanol (2 mL) in the presence of 2–3 drops of piperidine was heated to ~85° C. for about 2 h. The mixture cooled in ice bath and the solid was filtered off, washed with ethanol and dried to provide the compound 223 (21 mg) as a 70:30 mixture of (E:Z) isomers. HPLC:$R_t$ 14.41 min. and 12.37 min (method C).

Example 19

Preparation of 4-[(1-methyl-4-phenylindol-3-yl) methylene]-3-pyridino[3,4-e]pyridin-2-yl-2-pyrazolin-5-one (Compound 295)

(a) Preparation of the 3-pyridino[3,4-e]pyridin-2-yl-2-pyrazolin-5-one (VIk)

To a mixture of 1,6-naphthyridine-2-carboxylic acid (1 g, 5.7 mmol) and 100 mL of methanol was added carefully ~0.5 mL of conc. $H_2SO_4$. The mixture was kept under reflux overnight. The mixture was cooled to room temperature and solvent was evaporated. To the residue was added carefully (carbon dioxide evolution) half saturated sodium bicarbonate solution to neutralize the acid. The mixture was extracted from ethyl acetate (3 times) and the combined organic was washed with brine. After drying over anhydrous $MgSO_4$, solvent was evaporated. The product, 1,6-naphthyridine-2-carboxylic acid methyl ester, (IIIe) was isolated as a solid (932 mg, 87% yield), which was used for the next step without further purification. A mixture of ester (IIIe) (322 mg, 1.71 mmol) and methylacetate (dry, 10 mL) was treated with NaH (60% dispersion in mineral oil, 100 mg, 2.5 mmol) and the resulting mixture was kept under reflux for 2 h, during which a cake formation was noticed. The reaction mixture was cooled to room temperature and solvent was evaporated. The residue was treated ~20 mL of water. The mixture was neutralized with conc. HCl. A solid was obtained which was filtered, washed (water followed by hexane) and dried. Yield: 158 mg (40%). The product, ethyl 3-oxo-3-pyridino[3,4-e]pyridin-2-yl-propanoate, (Vf) was used for the next step without further purification.

A mixture of the above β-ketoester (Vf) (153 mg, 0.66 mmol), hydrazine hydrate (25 μl, 0.8 mmol) and absolute ethanol (5 mL) was kept under reflux. After 1 h, more hydrazine hydrate (75 μL, 2.4 mmol) was added and reflux was continued. A solid separated out. After 3 h, the mixture was cooled (ice bath) and the solid was filtered, washed (cold ethanol) and dried to isolate the product, 1,6-naphthyridinyl pyrazolone, (VIk), 66 mg (47% yield). MS: 213.

(b) Preparation of Compound 295

A mixture of the above pyrazolone, (VIk) (10 mg, 0.047 mmol), 5,6-methylenedioxy-1-methyl-indole-3-carboxaldehyde (11 mg, 0.054 mmol) in 1 mL of absolute ethanol along with a drop of piperidine was kept under stirring at 85–90° C. A solid separated. After 2 h the mixture was cooled to room temperature and the solid was filtered, washed with ethanol and dried to isolate the product (11 mg, 59% yield). MS: 398 (M+H).

Example 20

Preparation of 4-[(dimethylamino)methylene]-3-(1,3-thiazol-2-yl)-2-pyrazolin-5-one. (Compound 296)

To a solution of the pyrazolone (VIa), (250 mg, 1.5 mmol) in dry THF (12 mL) was added N,N-dimethylformamide di-tert-butyl acetal (0.319 g, 1.05 equiv) and the reaction mixture was heated under reflux for 15 min. TLC (10% methanol-chloroform) showed complete conversion of the pyrazolone ($R_f$=0.08) to a new product ($R_f$=0.17). Concentration of the reaction gave compound 296 as a solid. $^1$H-HMR (d$_6$-DMSO) δ 11.26 (s, 1H, enolic), 8.69 (s, 1H, =CH), 7.86 (s, 1H), 7.67 (s, 1H), 3.79 (s, 3H), 3.33 (s, 3H); electrospray MS, m/z 223 [M+1]$^+$ base peak; HPLC Rt=5.01 min. versus Rt=4.06 min. for the pyrazolone (VIa), (method A).

Example 21

Preparation of 4-[(2-hydroxyindol-3-yl)methylene]-3-(1,3-thiazol-2-yl)-2-pyrazolin-5-one. (Compound 297)

Compound 296 was taken up in dry ethanol (18 mL) and potassium tert-butoxide (0.5 mL of a 1.0 M solution in THF) was added, followed by oxindole (200 mg, 1.5 mmol) and the reaction was stirred under reflux and monitored by HPLC and by TLC (10% methanol-chloroform). HPLC after 4.5 h showed a new component with a retention time of 11.20 min, (method A). The reaction was stopped after 46 h, and the reaction mixture was concentrated to provide the crude product (215 mg) as a dark red solid: electrospray MS, m/z 311, [M+1]$^+$. A sample of the crude product (35 mg) was purified by chromatography on a C8 SEP-PAK cartridge (35 cc size) using a 15% acetonitrile-water to a 60% acetonitrile-water gradient. Evaporation of solvent from the fraction containing the product provided compound 297 (11 mg) as a reddish-yellow solid. $^1$H-NMR (DMSO-d$_6$) δ 13.22 (bs, 1H), 11.61 (s, 1H), 8.94 (s, 1H), 8.05 (s, 1H), 7.80 (s, 1H), 7.5 (m, 1H), 7.22 (m, 1H), 7.11 (m, 1H), 7.00 (m, 1H), 3.66 (bs, 1H), $^{13}$C NMR (DMSO-d6) δ 171.2, 163.0, 159.2, 157.0, 146.6, 144.8, 138.7, 131.7, 128.4, 127.3, 123.7, 121.6, 119.5, 117.9, 112.0. MS 311 (M+H), HPLC: Rt=111.19 min (method A).

The starting heterocyclic methyl ketones or esters were either purchased from the commercial sources or the corresponding commercially available acids were converted to the corresponding methyl or ethyl esters by standard procedure (e.g. Fischer esterification, alcohol and TMS chloride (Example 17), using TMS-diazomethane or diazomethane etc.). The following heterocyclic ester derivatives, [1,2,3]thiadiazole-5-carboxylic acid ethyl ester and 4-phenyl-[1,2,3]thiadiazole-5-carboxylic acid ethyl ester, were prepared according to the literature procedure of Shafiee, A. Lalezari, I.; Mirrashed, M.; Nercesian, D. *J. Heterocyclic Chem.* 1977, 14, 567–571 and were used for the syntheses of compounds 183, 186, 193, 194, 195, 196, 201, 209, 218, 224, 226, 231,235, 238, 240, 241, 244, 245, 247, 248, 249, 250, 252, 265, 273, 286 and 198, respectively, as per schemes (1), (2) and (3) and following a procedure analogous to that described in example 8. The [1,2,3]Selenadiazole-5-carboxylic acid ethyl ester was prepared as per the literature procedure of Lalezari, I.; Shafiee, A.; Yalpani, M. *J. Org. Chem.* 1971, 36, 2836 and it was used for the syntheses of compounds 188 and 192 following a procedure analogous to that described in example 8. The 1-methyl-5-methoxy-4-nitro-indole-3-carboxaldehyde was prepared according to Naylor, M.; Jaffar, M.; Nolan, J.; Stephens, M. A.; Butler, S.; Patel, K. B.; Everett, S. A.; Adams, G. E.; Stratford, I. J., *J. Med. Chem.* 1997, 40, 2335 was used for the preparation of compounds 170, 180 and 182 as described in example 1.

By employing thallium chemistry, the 4-iodo-5-methoxy-indole-3-carboxaldehyde was prepared according to the procedure of Moody, C. J.; Swann, E. *J. Chem. Soc. Perkin I* 1993, 21, 2561 and the 5-chloro-4-iodo-indole-3-carboxaldehyde according to the procedure of Ohta, T.; Yamato, Y.; Tahira, H.; Somei M., *Heterocycles* 1987, 11, 2817 (and references therein). These derivatives were subsequently reacted with NaH and iodomethane in DMF to provide the corresponding N-methyl derivatives, which were then used for the preparation of compounds 190, 280 and 212 following a procedure analogous to that described in example 1. Following the general procedure of Ohta, T.; Yamato, Y.; Tahira, H.; Somei M., *Heterocycles* 1987, 11, 2817 (and references therein), as used above for the preparation of the 5-chloro-4-iodo-indole-3-carboxaldehyde, the 4-halogenated derivatives for a number of commercially available 5 or 6 substituted indole-3-carboxyladehydes were prepared via thallium-mediated chemistry, using (i) reaction with thallium tris-trifluoro acetate, followed by (ii) reaction an electrophile, such as KI or CuBr$_2$. The resulting 4,5$^-$ or 4,6$^-$ disubstituted indole-3-carboxaldehydes were subsequently methylated at the indole N-position, as described in examples 13 and 16. The products were used for condensation with appropriate pyrazolones as described in example 1, to provide the desired compounds. Compounds 203, 266, 267, 281, 214, 221, 220, 222, 223, 289, 218, 219, 225, 226, 227, 228, 229, and 230 were derived following the sequence of steps described above.

The 1-(2-cyanoethyl)-indole-3-carboxaldehyde was prepared according to the procedure of Blume, R. C.; Lindwall, H. G. *J. Org. Chem.* 1945, 255 and was used for the preparation of compounds 64, 65, 66 and 67 following a procedure analogous to that described in example 1. The 4,5,6,7-tetrahydro-indole-2-carboxaldehyde was prepared according to the procedure of Sun, Li.; Tran, N.; Liang, C.; Hubbard., S.; Tang, F.; Lipson, K.; Schreck, R.; Zhou, Y.; McMahon, G.; Tang, C. *J. Med. Chem.* 1994, 25, 4307 and it was used for the preparation of compounds 277, 278, 279 and 288.

The indole-3-carboxaldehyde was functionalized using a variety of electrophiles at the indole nitrogen using NaH/DMF according to the general procedure as used for example 13. The 5-chloro-indole-3-carboxaldehyde was used to prepare the N-ethyl and N-allyl derivatives, which were used for the preparation of compounds 132, 148 and Compound 149, respectively. A general procedure, as described by Güngör, T.; Malabre P.; Teulon, J-M.; Camborde, F.; Meignen, J.; Hertz, F.; Virone-Oddos, A.; Caussade, F.; Cloarec, A. *J. Med. Chem.* 1994, 25, 4307, using K$_2$CO$_3$/DMF was used to prepare (a) the N—CH$_2$CH$_2$—OBn analog which was used for the preparation compounds 71 and 72; (b) the N-iso-butyl analog, which was used for the preparation compound 73, following a procedure analogous to as described in example 1.

The 5-hydroxy indole underwent selective O-alkylation with propargyl bromide using Cs$_2$CO$_3$ in acetone at room temperature, according to the procedure of Macor, J. E.; Blank, D. H.; Post, R. *J. Tetrahedron Lett.* 1994, 35, 45, which was then converted to the N-methyl and 3-formyl derivative using methods described in Examples 13 and 16. This aldehyde was used for the preparation of compound 155, following a procedure analogous to as described in example 1. Similarly, a number of 4-, 5-, 6- or 7-alkoxy substituted indole derivatives were prepared and used for syntheses of corresponding pyrazolone analogs (see Table 1).

The 6-phenyl-1-methyl-indole-3-carboxaldehyde was prepared from the 6-bromo-indole following a procedure similar to the one described above in example 16, and it was used for the synthesis of compound 215.

The 5- and 6-carbomethoxy-indoles were converted to the corresponding N-methyl-3-carboxaldehyde derivatives analogous to the method described in examples 13 and 16, and these esters were subsequently hydrolyzed to the corresponding carboxylic acids. The 5-COOMe carboxaldehyde derivative was used for the synthesis of compounds 237, 238, 239 and 255. The corresponding 5-COOH carboxaldehyde was used for the synthesis of compounds 251 and 255. Similarly, 6-COOMe carboxaldehyde derivative was used for the synthesis of compounds 115, 116, and 117 and the corresponding 6-COOH carboxaldehyde was used for the synthesis of compound 222.

A number of tricyclic derived indoles, e.g. 5,6-methylenedioxy-1-methyl-indole and 1H-pyrrrolo[3,2-H]quinoline were converted to corresponding to N-methyl and C-formyl (i.e. carboxaldehyde) derivatives and were used to prepare pyrazolone derivatives. The former was used to prepare compounds 139, 144, 209, 262, 289, 294 and 295; and the latter aldehyde was used to prepare compounds 284 and 285, respectively.

The heterocyclic substituted pyrazolones of the present invention are useful, inter alia, as therapeutic agents. Particularly, the compounds are useful for protein kinase inhibition. The heterocyclic substituted pyrazolones may inhibit, for example, kinases selected from abl, AKT, bcr-abl, Blk, Brk, Btk, c-kit, c-met, c-src, CDK1, CDK2, CDK4, CDK6, chk1, chk2, cRaf1, CSF1R, CSK, EGFR, ErbB2, ErbB3, ErbB4, ERK (Eph), Fak, fes, FGFR1, FGFR2, FGFR3, FGFR4, FGFR5, MLK1, MLK2, MLK3, DLK, trkA, trkB, trkC, Fgr, FLK-4, flt-1, Fps, Frk, Fyn, GSK, Hck, IGF-1R, INS-R, Jak, JNK, VEGFR1, VEGFR2, VEGFR3, Lck, Lyn, MEK, p38, PDGFR, PIK PKC, PYK2, ros, tie$_1$, tie$_2$, UL97, Yes and Zap70.

Thus, the properties of the compounds of the present invention are beneficial in therapeutic settings. The activities of the heterocyclic substituted pyrazolones toward certain enzymes can be exploited to combat the deleterious consequences of these enzymes. For example, inhibition of the Vascular Endothelial Growth Factor Receptor (VEGFR) implies utility in, for example, diseases where angiogenesis plays important roles, such as cancer of solid tumors, endometriosis, diabetic retinopathy, psoriasis, hemangioblastoma, as well as other ocular diseases and cancers. Inhibition of trk implies utility in, for example, diseases of the prostate such as prostate cancer and benign prostate hyperplasia, and treatment of inflammatory pain. Inhibition of the Platelet Derived Growth Factor Receptor (PDGFR) implies utility in, for example, various forms of neoplasia, rheumatoid arthritis, pulmonary fibrosis, myelofibrosis, abnormal wound healing, diseases with cardiovascular end points, such as atherosclerosis, restenosis, post-angioplasty restenosis, and the like. Inhibition of mixed lineage kinase (MLK) implies utility in, for example, Alzheimer's disease; motor neuron disorders (e.g. amyotrophic lateral sclerosis); Parkinson's disease; cerebrovascular disorders (e.g., stroke, ischaemia); Huntington's disease; AIDS dementia; epilepsy; multiple sclerosis; peripheral europathies (e.g., those affecting DRG neurons in chemotherapy-associated peripheral neuropathy) including diabetic neuropathy; disorders induced by excitatory amino acids; and disorders associated with concussive or penetrating injuries of the brain or spinal cord.

Inhibition of fibroplast growth factor receptor kinase (FGFR) implies utility in, for example, restenosis, post-angioplasty restenosis, atherosclerosis, pulmonary fibrosis, various cancers including, but not limited to, prostate cancer, breast cancer, abnormal wound healing, and benign prosthetic hypertrophy.

The activities of heterocyclic substituted pyrazolones may also have positive effects on the function and survival of trophic factor responsive cells by promoting the survival of neurons. With respect to the survival of a cholinergic neuron, for example, the compound may preserve the survival of a cholinergic neuronal population at risk of dying (due to, e.g., injury, a disease condition, a degenerative condition or natural progression) when compared to a cholinergic neuronal population not presented with such compound, if the treated population has a comparatively greater period of functionality than the non-treated population.

A variety of neurological disorders are characterized by neuronal cells which are dying, injured, functionally compromised, undergoing axonal degeneration, at risk of dying, etc. These disorders include, but are not limited to, Alzheimer's disease; motor neuron disorders (e.g. amyotrophic lateral sclerosis); Parkinson's disease; cerebrovascular disorders (e.g., stroke, ischaemia); Huntington's disease; AIDS dementia; epilepsy; multiple sclerosis; peripheral neuropathies (e.g., those affecting DRG neurons in chemotherapy-associated peripheral neuropathy) including diabetic neuropathy; disorders induced by excitatory amino acids; and disorders associated with concussive or penetrating injuries of the brain or spinal cord.

The compounds may function as survival promoting agents for other neuronal cell types, e.g., dopaminergic or glutamatergic. Growth factor may regulate survival of neurons by signaling cascades downstream of the small GTP binding proteins ras, rac, and cdc42 (Denhardt, D. T., Biochem. J., 1996, 318, 729). Specifically, activation of ras leads to phosphorylation and activation of extracellular receptor-activated kinase (ERK), which has been linked to biological growth and differentiation processes.

Stimulation of rac/cdc42 leads to an increase in activation of JNK and p38, responses that are associated with stress, apoptosis, and inflammation. Although growth factor responses are primarily via the ERK pathway, affecting these latter processes may lead to alternative mechanisms of neuronal survival which may mimic growth factor enhancing survival properties (Xia et al., Science, 1995, 270, 1326). The compounds may also function as survival promoting agents for neuronal and non-neuronal cells by mechanisms related to, but also distinct from, growth factor mediated survival, for example, inhibition of the JNK and p38 MAPK pathways which may lead to survival by inhibition of apoptotic cell death processes.

The present compounds may be useful in the treatment of disorders associated with decreased ChAT activity or the death, injury to spinal cord motoneurons, and also have utility in, for example, diseases associated with apoptotic cell death of the central and peripheral nervous system, immune system and in inflammatory diseases. ChAT catalyzes the synthesis of the neurotransmitter acetylcholine, and it is considered an enzymatic marker for a functional cholinergic neuron. A functional neuron is also capable of survival. Neuron survival is assayed by quantitation of the specific uptake and enzymatic conversion of a dye (e.g., calcein AM) by living neurons. The compounds described herein may also find utility in the treatment of disease states involving malignant cell proliferation, such as many cancers.

Additionally, inhibition of Src, raf, and the cyclin-dependent kinases (CDK) 1, 2, and 4 may be useful for the treatment of cancer. Regulation of CDK2 kinase may be useful for the treatment of restenosis. Regulation of one or more of CDK5 or GSK3 kinases may be useful for the treatment of Alzheimers. Regulation of one or more of c-Src kinase may be useful for the treatment of osteoporosis.

Regulation of one or more of GSK-3 kinase may be useful for the treatment of type-2 diabetes. Regulation of one or more of p38 kinase may be useful for the treatment of inflammation. Regulation of one or more of TIE-1, or TIE-2 kinases may be useful for the treatment of angiogenesis. Regulation of one or more of UL97 kinase may be useful for the treatment of viral infections. Regulation of one or more of CSF-1R kinase may be useful for the treatment of bone and hematopoetic diseases. Regulation of one or more of and Lck kinase may be useful for the treatment autoimmune diseases and transplant rejection. Regulation of topoisomerases Topo-I or Topo II may be useful for the treatment of cancer.

Because of their varied utilities, the properties of heterocyclic substituted pyrazolones may be exploited in other settings, such as research. For example, the compounds can be used in the development of in vitro models of neuronal cell survival, function, identification, or for the screening of other synthetic compounds which have activities similar to that of the of heterocyclic substituted pyrazolone compounds. Thus, the compounds provided by this invention are useful as standard or reference compounds for use in tests or assays for determining the activity of an agent in a pharmaceutical research program.

The compounds can also be utilized to investigate, define and determine molecular targets associated with functional responses. For example, by radio-labelling an heterocyclic substituted pyrazolone compound associated with a specific cellular function (e.g., mitogenesis), the target entity to which the derivative binds can be identified, isolated, and purified for characterization. By way of further illustration, compounds may be used in the development of assays and models for further enhancement of the understanding of the roles that inhibition play in the mechanistic aspects of the associated disorders and diseases. Thus, the compounds of the present invention are useful as diagnostic reagents in diagnostic assays such as the assays described herein.

The inhibition of enzymatic activity by the heterocyclic substituted pyrazolones of the present invention can be determined using, for example, the following assays:

1. Vascular Endothelial Growth Factor Receptor-1 kinase inhibition assay (VEGFR1)
2. Vascular Endothelial Growth Factor Receptor-2 kinase inhibition assay (VEGFR2)
3. trkA tyrosine kinase (trkA) inhibition assay
4. Mixed Lineage Kinase-1 (MLK1) inhibition assay
5. Mixed Lineage Kinase-2 (MLK2) inhibition assay
6. Mixed Lineage Kinase-3 (MLK3) inhibition assay
7. Fibroplast Growth Factor Receptor (FGFR1) inhibition assay.

Descriptions of these assays, and the results obtained therein, are set below. The results are intended to be illustrative and not to be construed as limiting the scope of the disclosure. For convenience, certain abbreviations are used to delineate the results which are defined in the body of the text. Others are defined as follows: "$\mu$g" for microgram, "mg" for milligram, "g" for gram, "$\mu$L" for microliter, "mL" for milliliter, "L" for liter, "nM" for nanomolar, "$\mu$M" for micromolar, "mM" for millimolar, "M" for molar, and "nm" for nanometer. The compounds of the present invention preferably demonstrate measurable inhibition in the assays described herein at a concentration of about 100 $\mu$M to about 10 $\mu$M. More preferably, compounds of the present invention demonstrate measurable inhibition at concentrations of about 10 $\mu$M to about 1 $\mu$M. Even more preferably, compounds of the present invention demonstrate measurable inhibition at concentrations which are lower than 1 $\mu$M.

Inhibition of Vascular Endothelial Growth Factor Receptor-1 Kinase Activity

The VEGFR1 kinase activity assay utilizes an ELISA-based format in a 96-well FluoroNUNC Maxisorp plate with a time-resolved fluorescence readout. The plate was coated with 100 $\mu$l/well of substrate solution (recombinant human PLC-$\gamma$/GST) at a concentration of 40 $\mu$g/ml in Tris buffered saline (TBS). The VEGFR1 activity was assayed in 100-$\mu$l assay micture containing 50 mM HEPES (pH 7.4), 30 $\mu$M ATP, 10 mM $MnCl_2$, 0.1% BSA, 2% DMSO, and 300 ng/ml prephosphorylated recombinant human baculovirus-expressed VEGFR1 cytoplasmic domain. Compounds were screened for inhibition of the VEGFR1 kinase activity at a concentration of 1 $\mu$M. The kinase reaction was allowed to proceed at 37° C. for 15 minutes. The detection antibody, europium-labeled anti-phosphotyrosine antibody (Wallac #CR04-100), was added at 1:5000 dilution in block buffer (3% BSA in TBST). After a 1-hour incubation at 37° C., 100 $\mu$l of enhancement solution (Wallac #1244-105) was added and the plate was gently agitated. After 5 min, the fluorescence of the resulting solution was measured using the BMG Fluostar (Model # 403). The results are summarized in Table 3.

TABLE 3

Inhibitory Effects of Heterocyclic Substituted Pyrazolones on VEGF-1 Receptor Kinase Activity

| Compound Number | VEGFR-1 kinase % inhibition @ 1 uM |
|---|---|
| 1 | 35 |
| 2 | 9 |
| 3 | 22 |
| 4 | 20 |
| 5 | 10 |
| 6 | 14 |
| 7 | 13 |
| 8 | 21 |
| 9 | 51 |
| 10 | 41 |
| 11 | 23 |
| 12 | 29 |
| 13 | 39 |
| 14 | 8 |
| 15 | 12 |
| 16 | 18 |
| 17 | 17 |
| 18 | 9 |
| 19 | 30 |
| 20 | 45 |
| 21 | 0 |
| 22 | 23 |
| 23 | 2 |
| 24 | 39 |
| 25 | 66 |
| 26 | 64 |
| 27 | 11 |
| 28 | 36 |
| 29 | 53 |
| 30 | 41 |
| 31 | 10 |
| 32 | 48 |
| 33 | 36 |
| 34 | 30 |
| 35 | 10 |
| 36 | 14 |
| 37 | 14 |
| 38 | 28 |
| 39 | 4 |
| 40 | 16 |
| 41 | 5 |

TABLE 3-continued

Inhibitory Effects of Heterocyclic Substituted Pyrazolones on VEGF-1 Receptor Kinase Activity

| Compound Number | VEGFR-1 kinase % inhibition @ 1 uM |
|---|---|
| 42 | 13 |
| 43 | −2 |
| 44 | 2 |
| 45 | 46 |
| 46 | 41 |
| 47 | 40 |
| 48 | 54 |
| 49 | 32 |
| 50 | 31 |
| 51 | 25 |
| 52 | 0 |
| 53 | 21 |
| 54 | 5 |
| 55 | 20 |
| 56 | 5 |
| 57 | 7 |
| 58 | 51 |
| 59 | −2 |
| 60 | 63 |
| 61 | 44 |
| 62 | 38 |
| 63 | 40 |
| 64 | 26 |
| 65 | 22 |
| 66 | 24 |
| 67 | 22 |
| 68 | 11 |
| 69 | 5 |
| 70 | 1 |
| 71 | 12 |
| 72 | 12 |
| 73 | 12 |
| 74 | 74 |
| 75 | 5 |

Inhibition of Vascular Endothelial Growth Factor Receptor-2 Kinase Activity

Assay were performed as described for trkA kinase below. The 96-well microtiter plate (FluoroNUNC Maxisorp) was coated with 40 µg/ml recombinant human phospholipase C-γ1/glutathione S-transferase fusion protein. Inhibition studies were performed in 100 µl assay mixtures containing 50 mM HEPES, pH 7.4, 30 µM ATP, 10 mM $MnCl_2$, 0.1% BSA, 2% DMSO, and 1 µM of test compound. The reaction was initiated by adding prephosphorylated recombinant human baculoviral VEGFR2 cyctoplasmic domain. The reaction was allowed to proceed for 15 minutes at 37° C. The detection antibody, eurpium-labeled anti-phosphotyrosine antibody (Wallac #CR04-100), was added at 1:5000 dilution in block buffer (3% BSA in TBST). After a 1-hour incubation at 37° C., 100 µL of enhancement solution (Wallac #1244-105) was added and the plate was gently agitated. After 5 min, the fluorescence of the resulting solution was measured using the BMG Fluostar (Model # 403). The results are summarized in Table 4.

TABLE 4

Inhibitory Effects of Heterocyclic Substituted Pyrazolones on VEGF-2 Receptor Kinase Activity

| Compound Number | VEGFR-2 kinase % inhibition @ 1 uM |
|---|---|
| 1 | 65 |
| 2 | 21 |
| 3 | 39 |
| 4 | 33 |
| 5 | −5 |
| 6 | 9 |
| 7 | −3 |
| 8 | 35 |
| 9 | 49 |
| 10 | 64 |
| 11 | 50 |
| 12 | 26 |
| 13 | 25 |
| 14 | 13 |
| 15 | 11 |
| 16 | 34 |
| 17 | 48 |
| 18 | 12 |
| 19 | 44 |
| 20 | 67 |
| 21 | 12 |
| 22 | 41 |
| 23 | 7 |
| 24 | 32 |
| 25 | 64 |
| 26 | 76 |
| 27 | 40 |
| 28 | 80 |
| 29 | 68 |
| 30 | 68 |
| 31 | 16 |
| 32 | 47 |
| 33 | 25 |
| 34 | 32 |
| 35 | 19 |
| 36 | 27 |
| 37 | 62 |
| 38 | 42 |
| 39 | 13 |
| 40 | 26 |
| 41 | 13 |
| 42 | 28 |
| 43 | 25 |
| 44 | 18 |
| 45 | 72 |
| 46 | 71 |
| 47 | 64 |
| 48 | 58 |
| 49 | 50 |
| 50 | 44 |
| 51 | 55 |
| 52 | 19 |
| 53 | 34 |
| 54 | 4 |
| 55 | 38 |
| 56 | 8 |
| 57 | 30 |
| 58 | 47 |
| 59 | 14 |
| 60 | 88 |
| 61 | 75 |
| 62 | 52 |
| 63 | 75 |
| 64 | 43 |
| 65 | 43 |
| 66 | 32 |
| 67 | 20 |
| 68 | 26 |
| 69 | 5 |
| 70 | 51 |
| 71 | −1 |
| 72 | 3 |
| 73 | 15 |
| 74 | 88 |
| 75 | 32 |

TABLE 4-continued

Inhibitory Effects of Heterocyclic Substituted Pyrazolones on VEGF-2 Receptor Kinase Activity

| Compound Number | VEGFR-2 kinase % inhibition @ 1 uM |
|---|---|
| 76 | 39 |
| 77 | 21 |
| 78 | 63 |

Inhibition of trkA Tyrosine Kinase Activity

Selected heterocyclic substituted pyrazolones were tested for their ability to inhibit the kinase activity of baculovirus-expressed human trkA cytoplasmic domain using an ELISA-based assay as previously described (Angeles et al., Anal. Biochem. 236: 49–55, 1996). Briefly, a 96-well microtiter plate was coated with substrate solution (recombinant human phospholipase C-γ1/glutathione S-transferase fusion protein (Rotin et al., EMBO J., 11: 559–567, 1992). Inhibition studies were performed in 100 μl assay mixtures containing 50 mM Hepes, pH 7.4, 40 μM ATP, 10 mM MnCl$_2$, 0.1% BSA, 2% DMSO, and various concentrations of inhibitor. The reaction was initiated by addition of trkA kinase and allowed to proceed for 15 minutes at 37° C. An antibody to phosphotyrosine (UBI) was then added, followed by a secondary enzyme-conjugated antibody, alkaline phosphatase-labelled goat anti-mouse IgG (Bio-Rad). The activity of the bound enzyme was measured via an amplified detection system (Gibco-BRL). Inhibition data were analyzed using the sigmoidal dose-response (variable slope) equation in GraphPad Prism. The results are summarized in Table 5.

TABLE 5

Inhibitory Effects of Heterocyclic Substituted Pyrazolones on trkA Kinase Activity

| Compound Number | trkA % inhibition @ 1 uM |
|---|---|
| 1 | 24 |
| 2 | 39 |
| 3 | 60 |
| 4 | 53 |
| 5 | 2 |
| 6 | 31 |
| 7 | 33 |
| 8 | 20 |
| 9 | 41 |
| 10 | 26 |
| 11 | 65 |
| 12 | 44 |
| 13 | 45 |
| 14 | 35 |
| 15 | 15 |
| 16 | 29 |
| 17 | 52 |
| 18 | 70 |
| 19 | 45 |
| 20 | 60 |
| 21 | 56 |
| 22 | 44 |
| 23 | 26 |
| 24 | 22 |
| 25 | 65 |
| 26 | 42 |
| 27 | 49 |
| 28 | 34 |
| 29 | 43 |
| 30 | 22 |
| 31 | 39 |
| 32 | 8 |
| 33 | 32 |
| 34 | 25 |
| 35 | 23 |
| 36 | 40 |
| 37 | 28 |
| 38 | 40 |
| 39 | 31 |
| 40 | 27 |
| 41 | 17 |
| 42 | 29 |
| 43 | 42 |
| 44 | 23 |
| 45 | 39 |
| 46 | 29 |
| 47 | 37 |
| 48 | 47 |
| 49 | 56 |
| 50 | 28 |
| 51 | 56 |
| 52 | 10 |
| 53 | 20 |
| 54 | 20 |
| 55 | 47 |
| 56 | 48 |
| 57 | 33 |
| 58 | 30 |
| 59 | 40 |
| 60 | 71 |
| 61 | 35 |
| 62 | 45 |
| 63 | 60 |
| 64 | 10 |
| 65 | 22 |
| 66 | 32 |
| 67 | 40 |
| 68 | 42 |
| 69 | 35 |
| 70 | 32 |
| 71 | 15 |
| 72 | 38 |
| 73 | 8 |
| 74 | 53 |
| 75 | 23 |

Inhibition of Platelet Derived Growth Factor Receptor Kinase Activity Kinase Activity The heterocyclic substituted pyrazolones may be probed for their inhibitory effects on the kinase activity of baculovirus-expressed PDGFβ receptor kinase domain using the trkA kinase ELISA described above. Assays were performed in substrate (PLC-γ/GST)-coated 96-well microtiter plates. Each 100-μl reaction mixture contained 50 mM HEPES, pH 7.4, 20 μM ATP, 10 mM MnCl$_2$, 0.1% BSA, 2% DMSO, and various concentrations of inhibitor. The reaction was initiated by addition of prephosphorylated recombinant human enzyme (10 ng/ml PDGFRβ) and allowed to proceed for 15 minutes at 37° C. The prephosphorylated enzyme was prepared prior to use by incubation of the kinase in buffer containing 20 μM ATP and 10 mM MnCl$_2$ for 1 hour at 4° C. Detection of phosphorylated product was done by adding horseradish peroxidase (HRP)-conjugated anti-phosphotyrosine antibody (UBI). The HRP substrate solution containing 3,3',5,5'-tetramethylbenzidine and hydrogen peroxide was later added and the plates were incubated for 10 minutes at room temperature. The reaction was quenched with acid and the resulting absorbance was read at 450 nm using a Microplate Bio-kinetics Reader (Bio-Tek Instrument EL 312e). Inhibition data were analyzed using the sigmoidal dose-response (variable slope) equation in GraphPad Prism.

Inhibition of Mixed Lineage Kinase-1 Activity

The kinase activity of MLK1 was assessed using the Millipore Multiscreen TCA "in-plate" format as described for protein kinase C (Pitt & Lee, *J. Biomol. Screening*, 1: 47–51, 1996). Briefly, each 50-µl assay mixture contained 20 mM Hepes, pH 7.0, 1 mM EGTA, 10 mM MgCl$_2$, 1 mM DTT, 25 mM β-glycerophosphate, 60 µM ATP, 0.25 µCi [γ-$^{32}$P]ATP, 0.1% BSA, 500 µg/ml myelin basic protein (UBI #13-104), 2% DMSO, 1 µM of test compound, and 1 µg/ml of baculoviral GST-MLK1$_{KD}$. Samples were incubated for 15 min at 37° C. The reaction was stopped by adding ice cold 50% TCA and the protein were allowed to precipitate for 30 min at 4° C. The plates were then washed with ice cold 25% TCA. Supermix scintillation cocktail was added, and the plates were allowed to equilibrate for 1–2 hours prior to counting using the Wallac MicroBeta 1450 PLUS scintillation counter. The results are summarized in Table 6.

TABLE 6

Inhibitory Effects of Heterocyclic Substituted Pyrazolones on MLK-1 Kinase Activity

| Compound Number | MLK-1 Kinase % inhibition @ 1 uM |
| --- | --- |
| 1 | 12 |
| 2 | -8 |
| 3 | 2 |
| 4 | 9 |
| 5 | 14 |
| 6 | 25 |
| 7 | 9 |
| 8 | 15 |
| 9 | 22 |
| 10 | 22 |
| 11 | 21 |
| 12 | 27 |
| 13 | 10 |
| 14 | 8 |
| 15 | -3 |
| 16 | 18 |
| 17 | 6 |
| 18 | 14 |
| 19 | 4 |
| 20 | 21 |
| 21 | 4 |
| 22 | 1 |
| 23 | 30 |
| 24 | 10 |
| 25 | 11 |
| 26 | 10 |
| 27 | 6 |
| 28 | 2 |
| 29 | 21 |
| 30 | 2 |
| 31 | 27 |
| 32 | 5 |
| 33 | 8 |
| 34 | 17 |
| 35 | 7 |
| 36 | -9 |
| 37 | 15 |
| 38 | 16 |
| 39 | 4 |
| 40 | 33 |
| 41 | 13 |
| 42 | -9 |
| 43 | 13 |
| 44 | 25 |
| 45 | 24 |
| 46 | 13 |
| 47 | 33 |
| 48 | 2 |
| 49 | -10 |
| 50 | 11 |
| 51 | 26 |
| 52 | 5 |
| 53 | 7 |
| 54 | -12 |
| 55 | -5 |
| 56 | -22 |
| 57 | 44 |
| 58 | 44 |
| 59 | 41 |
| 60 | 37 |
| 61 | 8 |
| 62 | 15 |
| 63 | 14 |
| 64 | 10 |
| 65 | 10 |
| 66 | 11 |
| 67 | 3 |
| 68 | 17 |
| 69 | 21 |
| 70 | 21 |
| 71 | 9 |
| 72 | 14 |
| 73 | -1 |
| 74 | 44 |
| 75 | 5 |

Inhibition of Mixed Lineage Kinase-2 Activity

Assays were performed using the Millipore Multiscreen plate format as described for MLK1. Each 50-µl assay mixture contained 20 mM Hepes, pH 7, 1 mM EGTA, 10 mM MgCl$_2$, 1 mM DTT, 25 mM β-glycerophosphate, 100 µM ATP, 0.25 µCi [γ-$^{32}$P]ATP, 0.1% BSA, 500 µg/ml myelin basic protein (UBI #13-104), 2% DMSO, various concentrations of test compound, and 3 µg/ml of baculoviral GST-MLK2$_{KDLZ}$. Samples were incubated for 15 min. at 37° C. The reaction was stopped by adding ice cold 50% TCA and the proteins were allowed to precipitate for 30 min at 4° C. The plates were then washed with ice cold 25% TCA Supermix scintillation cocktail was added, and the plates were allowed to equilibrate for 1–2 hours prior to counting. The results are summarized in Table 7.

TABLE 7

Inhibitory Effects of Heterocyclic Substituted Pyrazolones on MLK-2 Kinase Activity

| Compound Number | MLK-2 Kinase % inhibition @ 1 uM |
| --- | --- |
| 1 | 7 |
| 2 | -10 |
| 3 | -1 |
| 4 | -10 |
| 5 | 9 |
| 6 | 6 |
| 7 | -12 |
| 8 | 0 |
| 9 | 15 |
| 10 | -9 |
| 11 | 7 |
| 12 | -7 |
| 13 | -17 |
| 14 | -18 |
| 15 | -12 |
| 16 | 7 |

TABLE 7-continued

Inhibitory Effects of Heterocyclic Substituted
Pyrazolones on MLK-2 Kinase Activity

| Compound Number | MLK-2 Kinase % inhibition @ 1 uM |
|---|---|
| 17 | −8 |
| 18 | −2 |
| 19 | −5 |
| 20 | −3 |
| 21 | −13 |
| 22 | −13 |
| 23 | −6 |
| 24 | 4 |
| 25 | −4 |
| 26 | −7 |
| 27 | −4 |
| 28 | 10 |
| 29 | 2 |
| 30 | 1 |
| 31 | 0 |
| 32 | −14 |
| 33 | −13 |
| 34 | 1 |
| 35 | −15 |
| 36 | −18 |
| 37 | 12 |
| 38 | 2 |
| 39 | −7 |
| 40 | −8 |
| 41 | −15 |
| 42 | −10 |
| 43 | 2 |
| 44 | −3 |
| 45 | −22 |
| 46 | 2 |
| 47 | −2 |
| 48 | 3 |
| 49 | 3 |
| 50 | −1 |
| 51 | 3 |
| 52 | 5 |
| 53 | −13 |
| 54 | −48 |
| 55 | 2 |
| 56 | −14 |
| 57 | 5 |
| 58 | 4 |
| 59 | −8 |
| 60 | 9 |
| 61 | −4 |
| 62 | −21 |
| 63 | 1 |
| 64 | 9 |
| 65 | −3 |
| 66 | 5 |
| 67 | −1 |
| 68 | 16 |
| 69 | 4 |
| 70 | 5 |
| 71 | 3 |
| 72 | 3 |
| 73 | 12 |
| 74 | 17 |
| 75 | −5 |

Inhibition of Mixed Lineage Kinase-3 Activity

Assays were performed using the Millipore Multiscreen plate format as described for MLK1. Briefly, each 50-μl assay mixture contained 20 mM Hepes, pH 7, 1 mM EGTA, 10 mM MgCl$_2$, 1 mM DTT, 25 mM β-glycerophosphate, 100 μM ATP, 0.25 μCi [γ-$^{32}$P]ATP, 0.1% BSA, 500 μg/ml myelin basic protein (UBI #13-104), 2% DMSO, various concentrations of test compound, and 2 μg/ml of baculoviral GST-MLK3$_{KD}$. Samples were incubated for 15 min at 37° C. The reaction was stopped by adding ice cold 50% TCA and the proteins were allowed to precipitate for 30 min at 4° C. The plates were then washed with ice cold 25% TCA. Supermix scintillation cocktail was added, and the plates were allowed to equilibrate for 1–2 hours prior to counting. The results are summarized in Table 8.

TABLE 8

Inhibitory Effects of Heterocyclic Substituted
Pyrazolones on MLK-3 Kinase Activity

| Compound Number | MLK-3 Kinase % inhibition @ 1 uM |
|---|---|
| 1 | 28 |
| 2 | −11 |
| 3 | 12 |
| 4 | −6 |
| 5 | −9 |
| 6 | 3 |
| 7 | 7 |
| 8 | 10 |
| 9 | 27 |
| 10 | 44 |
| 11 | 31 |
| 12 | 29 |
| 13 | 17 |
| 14 | 14 |
| 15 | −17 |
| 16 | 12 |
| 17 | 19 |
| 18 | 47 |
| 19 | 11 |
| 20 | 57 |
| 21 | 24 |
| 22 | 24 |
| 23 | 69 |
| 24 | 38 |
| 25 | 48 |
| 26 | 57 |
| 27 | 44 |
| 28 | 50 |
| 29 | 38 |
| 30 | 46 |
| 31 | 49 |
| 32 | 42 |
| 33 | 28 |
| 34 | 32 |
| 35 | 34 |
| 36 | 25 |
| 37 | 79 |
| 38 | 38 |
| 39 | 55 |
| 40 | 22 |
| 41 | 10 |
| 42 | 21 |
| 43 | 21 |
| 44 | 28 |
| 45 | 56 |
| 46 | 36 |
| 47 | 31 |
| 48 | 31 |
| 49 | 21 |
| 50 | 15 |
| 51 | 47 |
| 52 | 19 |
| 53 | 12 |
| 54 | 0 |
| 55 | 26 |
| 56 | −1 |
| 57 | 67 |
| 58 | 43 |
| 59 | 47 |
| 60 | 58 |
| 61 | 72 |
| 62 | 45 |
| 63 | 78 |
| 64 | 15 |
| 65 | 7 |
| 66 | 11 |
| 67 | 8 |
| 68 | 20 |

TABLE 8-continued

Inhibitory Effects of Heterocyclic Substituted
Pyrazolones on MLK-3 Kinase Activity

| Compound Number | MLK-3 Kinase % inhibition @ 1 uM |
|---|---|
| 69 | 9 |
| 70 | 15 |
| 71 | 9 |
| 72 | 28 |
| 73 | 5 |
| 74 | 72 |
| 75 | 24 |

Inhibition of Fibroblast Growth Factor Receptor-1 (FGFR1) Kinase Activity

The FGFR1 kinase activity was measured using an ELISA-based format in a 96-well FluoroNUNC Maxisorp plate with a time-resolved fluorescence readout as described for trkA kinase. The plate was coated with 100 µl/well of substrate solution (recombinant human PLC-γ/GST) at a concentration of 10 µg/ml in Tris buffered saline (TBS). The FDGFR1 activity was assayed in 100-µl assay micture containing 50 mM HEPES (pH 7.4), 20 µM ATP, 10 mM MnCl$_2$, 0.1% BSA, 2% DMSO, and 15 ng/ml recombinant human baculovirus-expressed FGFR1 cytoplasmic domain (prephosphorylated prior to use). Compounds were screened for inhibition of the FGFR1 kinase activity at a conentration of 1 µM. The kinase reaction was allowed to proceed at 37° C. for 15 minutes. The detection antibody, europium-labeled anti-phosphotyrosine antibody (Wallace #CR04-100), was added at 1:5000 dilution in block buffer (3% BSA in TBST). After a 1-hour incubation at 37° C., 100 µl of enhancement solution (Wallac #1244-105) and the plate was gently agitated. After 5 min, the fluorescence of the resulting solutions measured using the BMG Fluostar (Model # 403). The results are summarized in Table 9.

TABLE 9

Inhibitory Effects of Heterocyclic Substituted
Pyrazolones on Fibroplast Growth Factor Activity

| Compound Number | FGFR1 % inhibition @ 1 uM |
|---|---|
| 1 | 6 |
| 2 | 33 |
| 3 | 29 |
| 4 | 20 |
| 5 | −2 |
| 6 | 20 |
| 7 | 28 |
| 8 | 24 |
| 9 | 17 |
| 10 | 14 |
| 11 | 24 |
| 12 | 39 |
| 13 | 30 |
| 14 | 22 |
| 15 | 10 |
| 16 | 1 |
| 17 | 13 |
| 18 | 22 |
| 19 | 23 |
| 20 | 27 |
| 21 | 15 |
| 22 | 22 |
| 23 | 31 |
| 24 | 39 |
| 25 | 52 |
| 26 | 46 |
| 27 | 36 |
| 28 | 37 |
| 29 | 41 |
| 30 | 27 |
| 31 | 17 |
| 32 | 4 |
| 33 | 27 |
| 34 | 34 |
| 35 | 29 |
| 36 | 31 |
| 37 | 32 |
| 38 | 28 |
| 39 | 13 |
| 40 | 22 |
| 41 | 21 |
| 42 | 32 |
| 43 | 26 |
| 44 | 10 |
| 45 | 8 |
| 46 | 25 |
| 47 | 32 |
| 48 | 43 |
| 49 | 39 |
| 50 | 20 |
| 51 | 9 |
| 52 | 10 |
| 53 | 50 |
| 54 | 45 |
| 55 | 36 |
| 56 | 30 |
| 57 | −2 |
| 58 | 24 |
| 59 | 29 |
| 60 | 66 |
| 61 | 35 |
| 62 | 37 |
| 63 | 38 |
| 64 | 7 |
| 65 | 21 |
| 66 | 29 |
| 67 | 23 |
| 68 | 27 |
| 69 | 30 |
| 70 | 21 |
| 71 | 26 |
| 72 | 29 |
| 73 | 19 |
| 74 | 48 |
| 75 | 26 |

Dosage and Formulation

For therapeutic purposes, the compounds of the present invention can be administered by any means that results in the contact of the active agent with the agent's site of action in the body of a mammal. The compounds may be administered by any conventional means available for use in conjunction with pharmaceuticals, either as individual therapeutic agents or in a combination of therapeutic agents. They are preferably administered as the sole active agent in a pharmaceutical composition, but alternatively, they can be used in combination with other active ingredients, e.g., other growth factors which facilitate neuronal survival or axonal regeneration in diseases or disorders. The compounds are preferably combined with a pharmaceutical carrier selected on the basis of the chosen route of administration and standard pharmaceutical practice.

The compounds can be formulated into pharmaceutical compositions, for example, by admixture with pharmaceutically acceptable nontoxic excipients and carriers. Such compositions can be prepared for use in parenteral administration, particularly in the form of liquid solutions or suspensions; or oral administration, particularly in the form of tablets or capsules; or intranasally, particularly in the form of powders, nasal drops, or aerosols; or dermally, via, for example, trans-dermal patches.

The composition can be conveniently administered in unit dosage form and may be prepared by any of the methods well known in the pharmaceutical art, for example, as described in Remington's Pharmaceutical Sciences (Mack Pub. Co., Easton, Pa., 1980). Formulations for parenteral administration may contain as common excipients sterile water or saline, polyalkylene glycols such as polyethylene glycol, oils and vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds.

Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for trans-dermal patches are preferably lipophilic emulsions.

Compounds of Formula I and pharmaceutically acceptable salts thereof can be administered orally or non-orally, e.g., as an ointment or an injection. The concentrations of the compounds of this invention in a therapeutic composition can vary. The concentration will depend upon factors such as the total dosage of the drug to be administered, the chemical characteristics (e.g., hydrophobicity) of the compounds employed, the route of administration, the age, body weight and symptoms of a patient, etc. The compounds of this invention may be provided in an aqueous physiological buffer solution containing about 0.1 to 10% w/v compound for parenteral administration. Typical dose ranges are from about 1 mg to about 1 µg/kg of body weight per day; a preferred dose range is from about 0.01 mg/kg to 100 mg/kg of body weight per day, and preferably about 0.1 to 20 mg/kg once to four times per day. A preferred dosage of drug to be administered is likely to depend on variables such as the type and extent of progression of the disease or disorder, the overall health status of the particular patient, the relative biological efficacy of the compound selected, and formulation of the compound excipient, and its route of administration.

The pharmaceutical compositions in accordance with the present invention can be prepared by uniformly mixing an effective amount of a compound of Formula I or a pharmaceutically acceptable salt thereof, as an active ingredient, with a pharmaceutically acceptable carrier. The carrier may take a wide range of forms according to the forms of composition suitable for administration. It is desired that such pharmaceutical compositions are prepared in a unit dose form suitable for oral or non-oral administration. The forms for non-oral administration include ointment and injection.

Tablets can be prepared using excipients such as lactose, glucose, sucrose, mannitol and methyl cellulose, disintegrating agents such as starch, sodium alginate, calcium carboxymethyl cellulose and crystalline cellulose, lubricants such as magnesium stearate and talc, binders such as gelatin, polyvinyl alcohol, polyvinyl pyrrolidone, hydroxypropyl cellulose and methyl cellulose, surfactants such as sucrose fatty acid ester and sorbitol fatty acid ester, and the like in a conventional manner. It is preferred that each tablet contains 15–300 mg of the active ingredient.

Granules can be prepared using excipients such as lactose and sucrose, disintegrating agents such as starch, binders such as gelatin, and the like in a conventional manner. Powders can be prepared using excipients such as lactose and mannitot and the like in a conventional manner. Capsules can be prepared using gelatin, water, sucrose, gum arabic, sorbitol, glycerin, crystalline cellulose, magnesium stearate, talc, and the like in a conventional manner. It is preferred that each capsule contains 15–300 mg of the active ingredient.

Syrup preparations can be prepared using sugars such as sucrose, water, ethanol, and the like in a conventional manner.

Ointment can be prepared using ointment bases such as vaseline, liquid paraffin, lanolin and macrogol, emulsifiers such as sodium lauryl lactate, benzalkonium chloride, sorbitan mono-fatty acid ester, sodium carboxymethyl cellulose and gum arabic, and the like in a conventional manner.

Injectable preparations can be prepared using solvents such as water, physiological saline, vegetable oils (e.g., olive oil and peanut oil), ethyl oleate and propylene glycol, solubilizing agents such as sodium benzoate, sodium salicylate and urethane, isotonicity agents such as sodium chloride and glucose, preservatives such as phenol, cresol, p-hydroxybenzoic ester and chlorobutanol, antioxidants such as ascorbic acid and sodium pyrosulfite, and the like in a conventional manner.

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

What is claimed is:

1. A compound of Formula I:

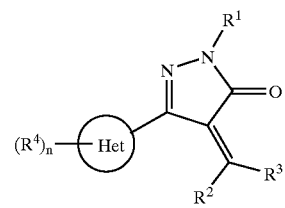

or a stereoisomer or pharmaceutically acceptable salt thereof, wherein: Het is a heterocycle selected from:

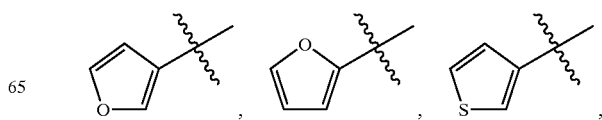

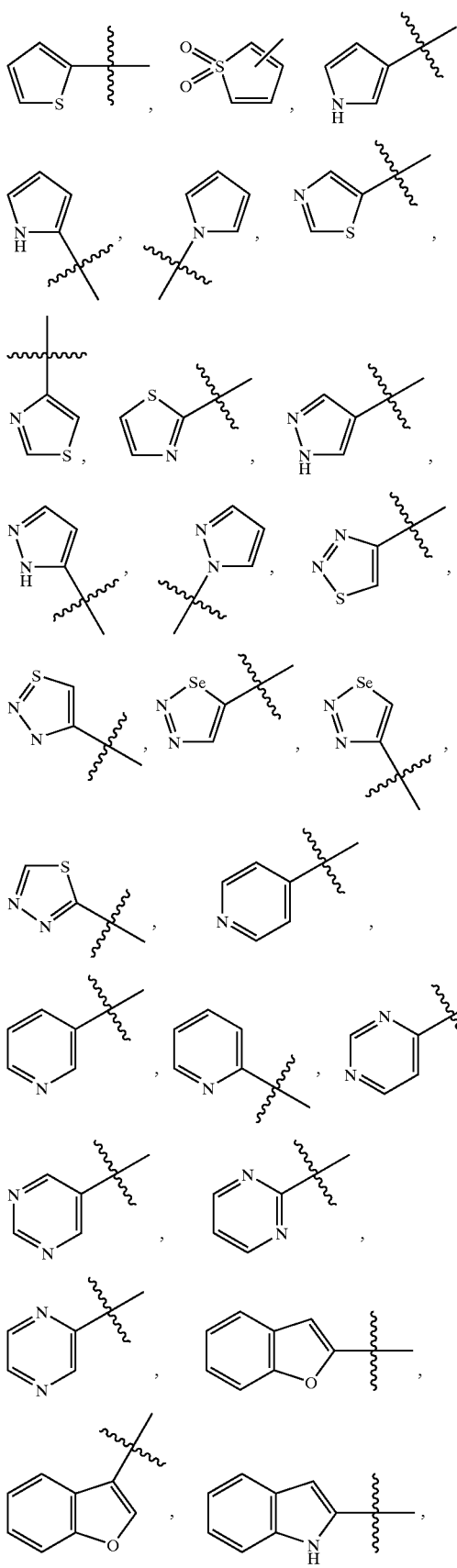

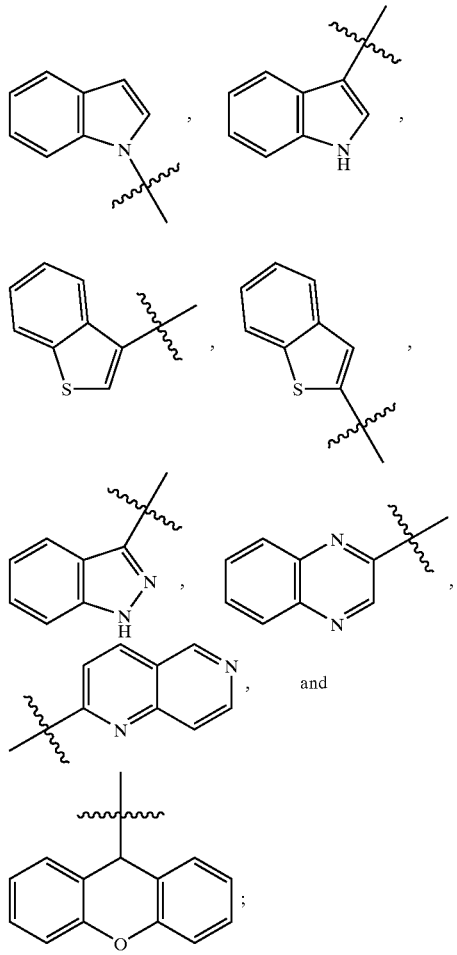

$R^1$ is selected from H, $C_{1-10}$ alkyl substituted with 0–5 $R^6$, $C_{2-8}$ alkenyl substituted with 0–5 $R^6$, $C_{2-8}$ alkynyl substituted with 0–5 $R^6$, $NR^aR^a$, $C(=O)R^b$, $C(=O)NHR^a$, $CO_2R^c$, and heterocycle substituted with 0–5 $R^6$;

with the provisos that when $R^1$ and Het are both 2-pyridinyl, $R^2$ and $R^3$ are other than 4-diethylamino-2-phenyl or phenyl subsituted with methyl or diisopropylamino; and when $R^1$ is 4-carboxy-phenethyl, Het and either $R^2$ or $R^3$ are other than both dimethylamino-thiophene; and when $R^1$ and $R^2$ are alkyl, Het is other than furanyl, thienyl or pyrrolyl;

$R^2$ and $R^3$ are independently selected from H, $C_{1-2}$ alkyl substituted with 1–5 $R^6$, $C_{3-10}$ alkyl substituted with 0–5 $R^6$, $C_{2-8}$ alkenyl substituted with 0–5 $R^i$, $C_{2-6}$ alkynyl, Cl, Br, I, CN, $(CH_2)_rNR^aR^a$, $(CH_2)_rOR^c$, $(CH_2)_rSR^c$, $(CH_2)_rC(=O)R^b$, $(CH_2)_rCO_2R^c$, $(CH_2)_rOC(=O)R^b$, $(CH_2)_rC(=O)NR^aR^a$, $(CH_2)_rNR^aC(=O)R^b$, $(CH_2)_rNR^aC(=O)OR^b$, $(CH_2)_rOC(=O)NHR^a$, $(CH_2)_rNR^aS(=O)_2R^b$, $(CH_2)_rS(=O)_2NR^aR^a$, $(CH_2)_rS(O)_pR^b$, $(CH_2)_r$carbocycle substituted with 0–5 $R^4$, and $CH_2)_r$heterocycle substituted with 0–5 $R^4$;

alternatively, $R^2$ and $R^3$ join to form a heterocycle substituted with 0–4 $R^4$, with the provisos that the heterocycle is other than 2-thiazolidinyl or 5-methyl-2-oxazolidinyl; and when Het is furanyl, $R^2$ and $R^3$ are not joined to form a heterocycle;

with the provisos that $R^2$ and $R^3$ are other than both H or both $SCH_3$; and when $R^2$ is H, and $R^3$ is phenyl, Het is other than 2-furanyl; and when $R^2$ is H and $R^3$ is $(CH_2)_rNR^aR^a$, r is other than 0;

$R^4$, at each occurrence, is independently selected from H, F, Cl, Br, I, CN, $CF_2CF_3$, $CF_3$, $NO_2$, CN, OH, $NR^aR^a$, $OR^c$, $C(=O)R^b$, $CO_2R^c$, $OC(=O)R^b$, $NR^aC(=O)R^b$, $C(=O)NR^aR^a$, $OC(=O)NR^aR^a$, $NR^aC(=O)OR^b$, $NR^aS(=O)_2R^b$, $S(=O)_2NR^aR^a$, $NR^aC(=S)R^b$, $C(=S)NR^aR^a$, $NR^aC(=O)NR^aR^a$, $NR^aC(=S)NR^aR^a$, $CH=NOR^c$, $CH=NR^a$, $CH=NNR^aR^a$, $(CH_2)_rS(O)_pR^b$, $O(CH_2)_qNR^aR^a$, $O(CH_2)_qOR^c$, $(CH_2)_rOR^{d'}$, $(CH_2)_rC(=O)R^{d'}$, $(CH_2)_rNHR^d$, $(CH_2)_rS(O)_pR^{d'}$, $C_{1-10}$ alkyl subsituted with 0–5 $R^6$, $C_{2-8}$ alkenyl substituted with 0–5 $R^6$, $C_{2-8}$ alkynyl substituted with 0–5 $R^6$; carbocycle substituted with 0–5 $R^6$, and heterocycle substituted with 0–5 $R^6$;

$R^6$, at each occurrence, is independently selected from $C_{1-6}$ alkyl substituted with 0–5 $R^h$, $C_{2-8}$ alkenyl, substituted with 0–5 $R^h$, $C_{2-8}$ alkynyl substituted with 0–5 $R^h$, F, Cl, Br, I, CN, $CF_2CF_3$, $CF_3$, $NO_2$, CN, $NR^fR^f$, $OR^f$, $C(=O)R^f$, $CO_2R^f$, $OC(=O)R^g$, $NR^fC(=O)R^f$, $C(=O)NR^fR^f$, $OC(=O)NR^fR^f$, $NR^eC(=O)OR^g$, $NR^fS(=O)_2R^g$, $S(=O)_2NR^fR^f$, $NR^aC(=S)R^g$, $C(=S)NR^fR^f$, $NR^fC(=O)NR^fR^f$, $NR^fC(=S)NR^fR^f$, $CH=NOR^e$, $CH=NR^e$, $CH=NNR^eR^e$, $S(O)_pR^f$, $O(CH_2)_pNR^fR^f$, $O(CH_2)_pOR^f$, $OR^d$, $NHR^d$, $C(=O)R^{d'}$, $S(O)_pR^{d'}$, carbocycle substituted with 0–5 $R^h$, heterocycle substituted with 0–5 $R^h$, $P(=O)(OR^e)_2$, and a $C_{5-7}$ monosaccharide wherein each hydroxyl group of the monosaccharide is unsubstituted or replaced by a group selected from H, $C_{1-4}$ alkyl, $C_{1-4}$ alkoxy, and $OC(=O)C_{1-4}$ alkyl;

$R^a$, at each occurrence, is independently selected from H, $C_{1-6}$ alkyl, $C_{2-6}$ alkenyl, $C_{2-6}$ alkynyl, $(CH_2)_rC_{3-6}$ cycloalkyl, and $(CH_2)_r$phenyl, wherein when $R^a$ is other than H, $R^a$ is substituted with 0–5 $R^h$;

alternatively, two $R^a$ may join to form a linker selected from $(CH_2)_qO(CH_2)_q$, $(CH_2)_qS(CH_2)_q$, and $(CH_2)_m$, wherein the linker is substituted with 0–5 $R^h$;

$R^b$, at each occurrence, is independently selected from $C_{1-6}$ alkyl, $C_{2-6}$ alkenyl, $C_{2-6}$ alkynyl, $(CH_2)_r$phenyl, and $(CH_2)_r$heterocycle, wherein $R^b$ is substituted with 0–5 $R^h$;

$R^c$, at each occurrence, is independently selected from H, $C_{1-6}$ alkyl, $C_{2-6}$ alkenyl, $C_{2-6}$ alkynyl, $C_{3-6}$ cycloalkyl, and $(CH_2)_r$phenyl, wherein when $R^c$ is other than H, $R^c$ is substituted with 0–5 $R^h$;

$R^d$, at each occurrence, is independently selected from the residue of an amino acid after the hydroxyl group of the carboxyl group is removed;

$R^{d'}$, at each occurrence, is independently selected from the residue of an amino acid after the hydrogen of the amine is removed;

$R^e$, at each occurrence, is independently selected from H and $C_{1-6}$ alkyl;

$R^f$, at each occurrence, is selected from H, $C_{1-6}$ alkyl substituted with 0–5 $R^h$, and $(CH_2)_r$phenyl substituted with 0–5 $R^h$;

$R^g$, at each occurrence, is independently selected from $C^{1-6}$ alkyl substituted with 0–5 $R^h$ and $(CH_2)_r$phenyl substituted with 0–5 $R^h$;

$R^h$, at each occurrence, is selected from F, Cl, Br, I, OH, $NO_2$, CN, $CF_3$, $CF_2CF_3$, $C_{1-4}$ alkyl, $C_{2-6}$ alkenyl, $C_{2-6}$ alkynyl, alkoxy, $C_{3-7}$ cycloalkyl, carboxyl, formyl, acetyl, propanoyl, butyryl, valeryl, pivaloyl, hexanoyl, acetamido, acetate, carbamyl, carboxy, $NH_2$, monoalkylamino, dialkylamino, phenyl, benzyl, phenethyl, napthyl, heterocycle, and keto;

$R^i$, at each occurrence, is selected from F, Cl, Br, I, OH, $NO_2$, CN, $CF_3$, $CF_2CF_3$, $C_{1-4}$ alkyl, $C_{2-6}$ alkenyl, $C_{2-6}$ alkynyl, alkoxy, $C_{3-7}$ cycloalkyl, carboxyl, formyl, acetyl, propanoyl, butyryl, valeryl, pivaloyl, hexanoyl, acetamido, carbamyl, $NH_2$, monoalkylamino, dialkylamino, phenyl, benzyl, and phenethyl;

m, at each occurrence, is independently selected from 2, 3, 4, and 5;

n, at each occurrence, is selected from 0, 1, 2, 3, 4, and 5;

p, at each occurrence, is independently selected from 0, 1, and 2;

q, at each occurrence, is independently selected from 1, 2, 3, and 4; and r, at each occurrence, is independently selected from 0, 1, 2, 3 and 4.

2. The compound of claim 1 wherein $R^1$ is H or alkyl.

3. The compound according to claim 1 wherein one of $R^2$ or $R^3$ is each independently selected from:

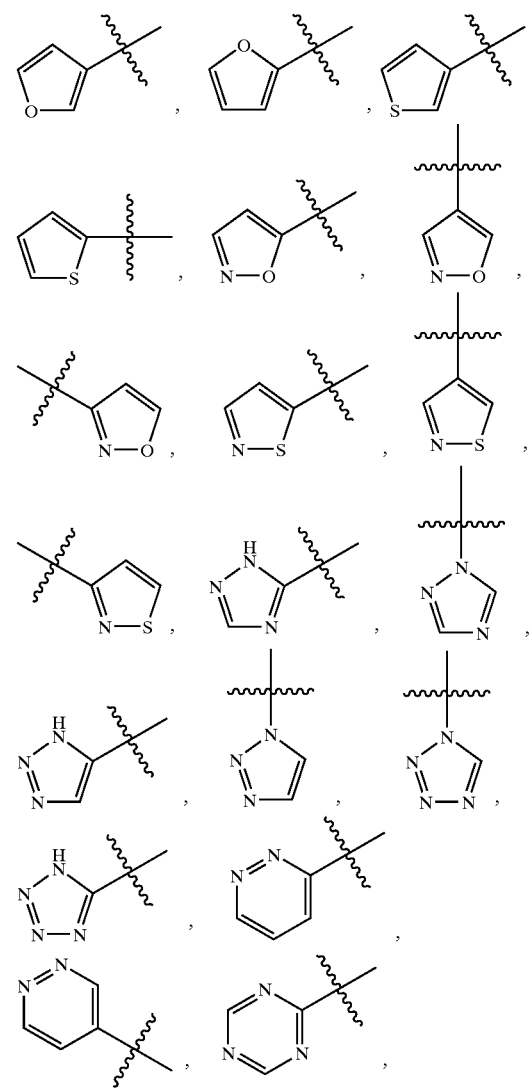

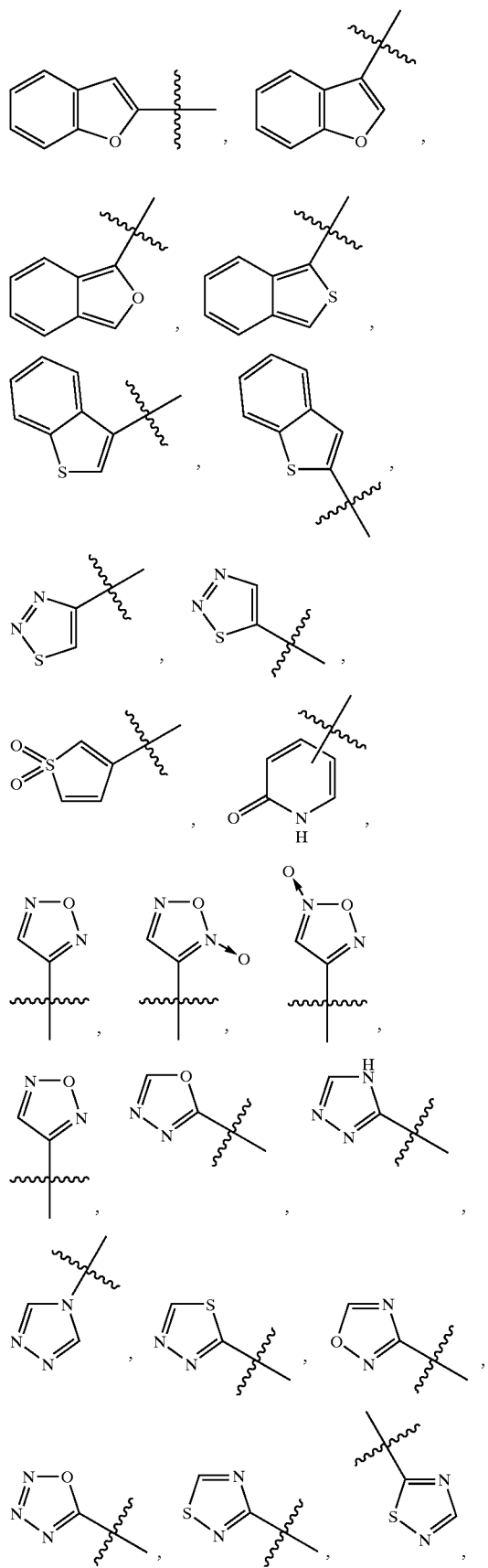
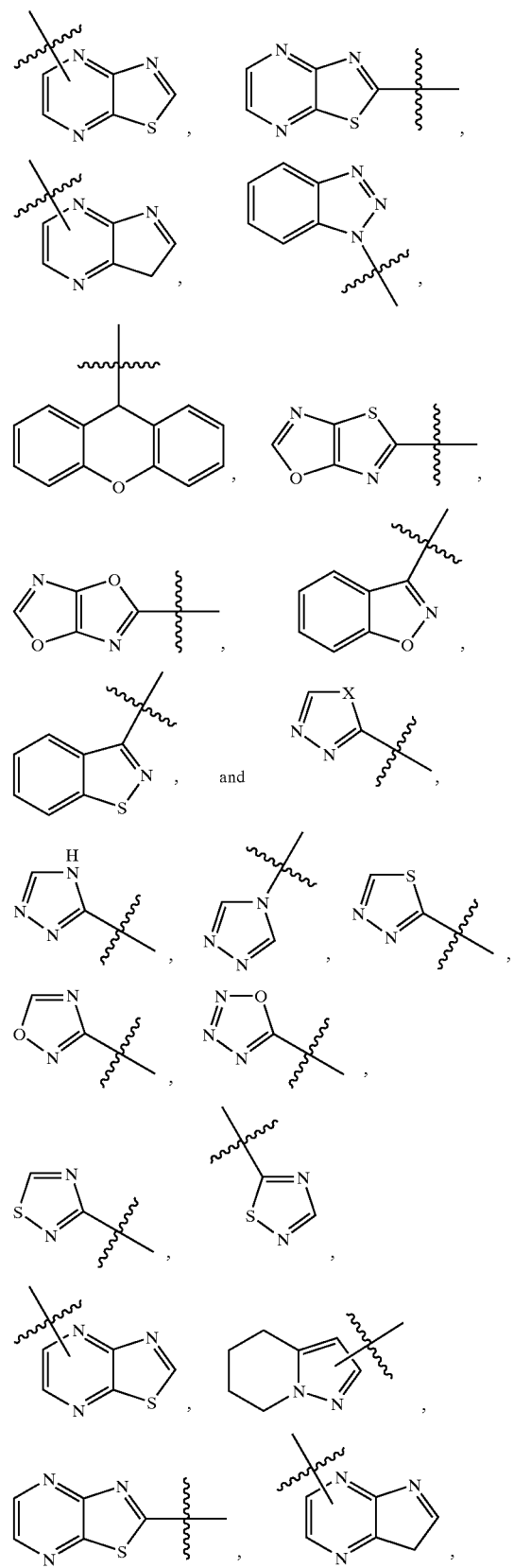

-continued
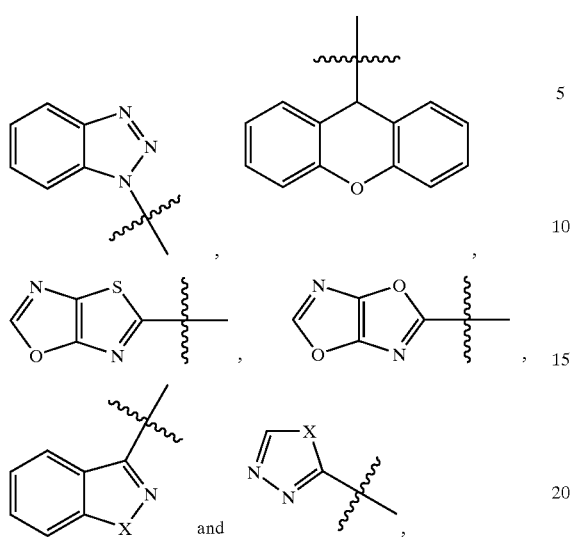
wherein X is N-alkyl.
4. The compound according to claim 1 wherein one of $R^2$ or $R^3$ is each independently selected from:
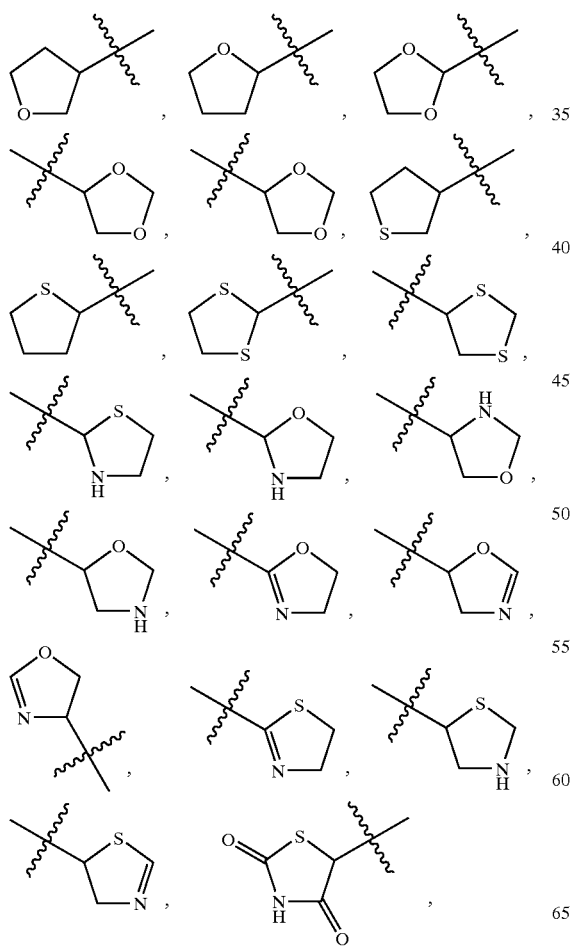
-continued
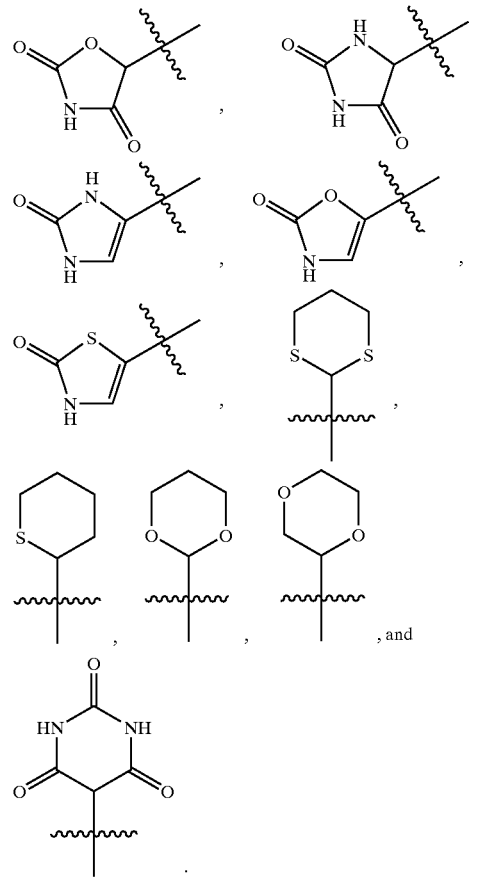
5. The compound according to claim 1 wherein Het is selected from:
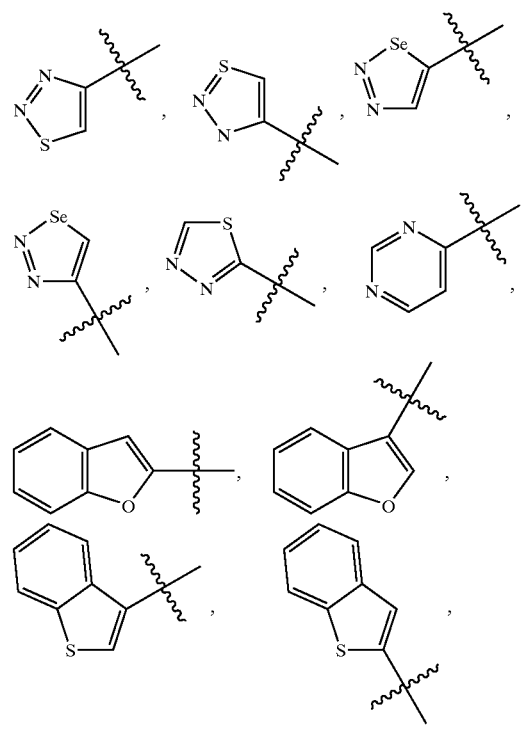

-continued
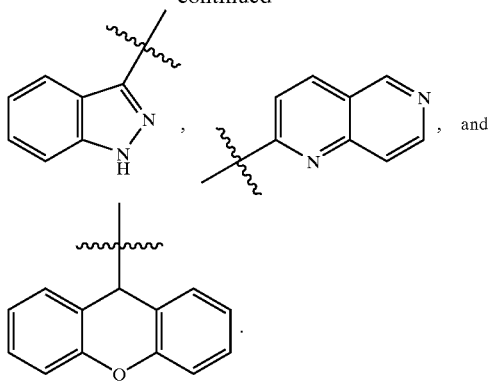
6. The compound according to claim 1 wherein $R^2$ and $R^3$ are independently selected from:
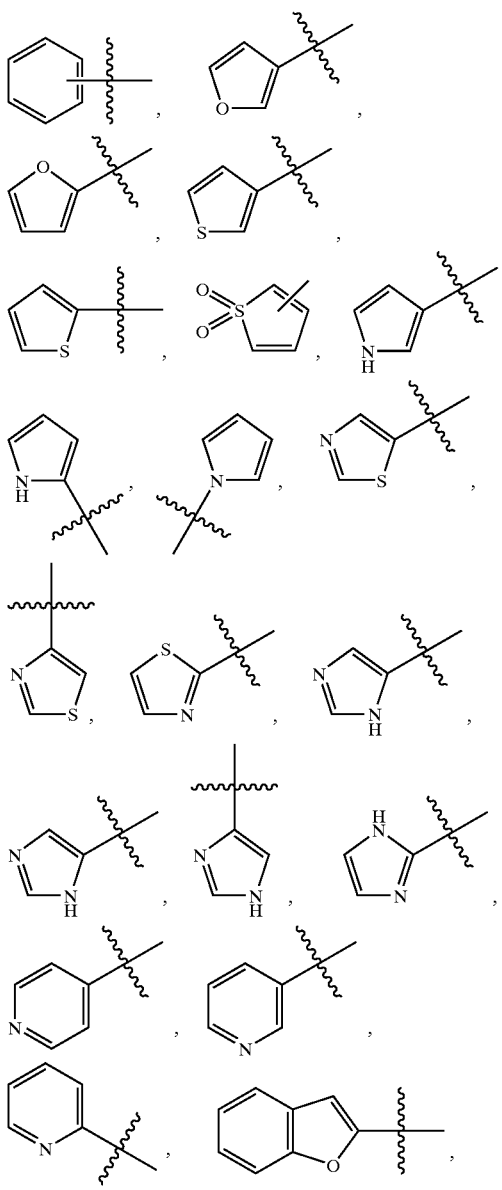
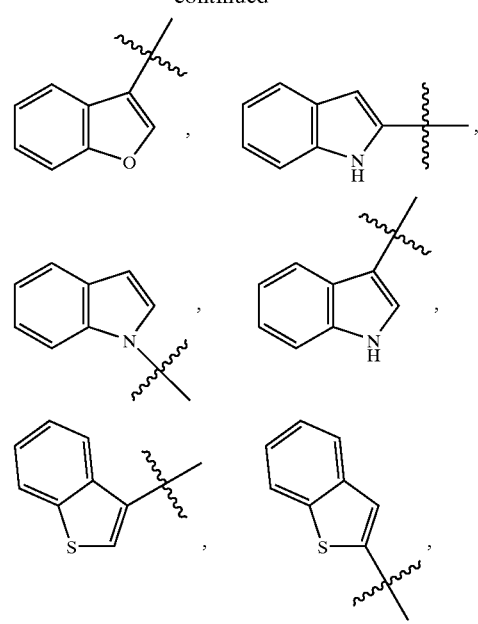
alternatively $R^2$ and $R^3$ can combine to form —$(CH_2)_2$N$(CH_3)(CH_2)_2$—.
7. The compound according to claim 6 wherein $R^2$ and $R^3$ are independently selected from:
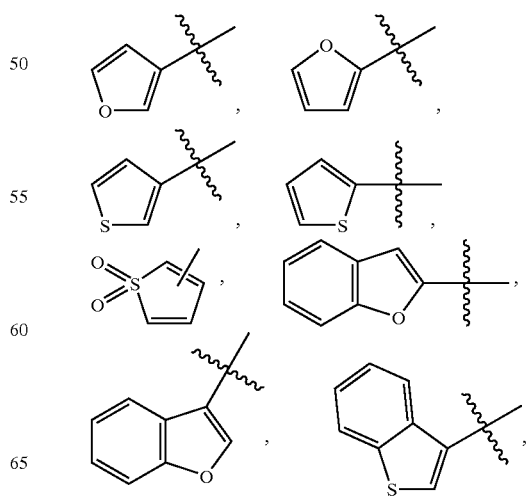

-continued alternatively R² and R³ can combine to form —(CH₂)₂N(CH₃)(CH₂)₂—.

8. The compound according to claim 1 wherein Het is selected from:

-continued

R² and R³ are independently selected from:

-continued

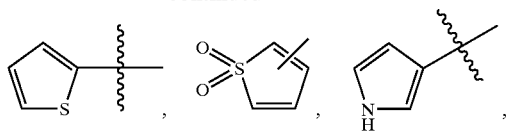

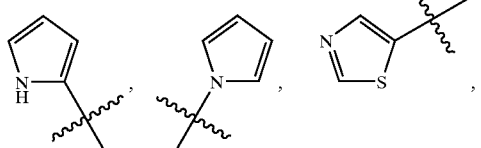

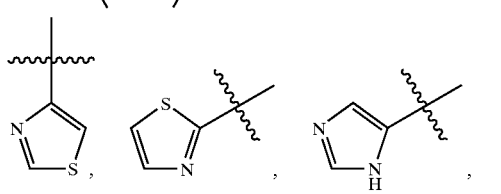

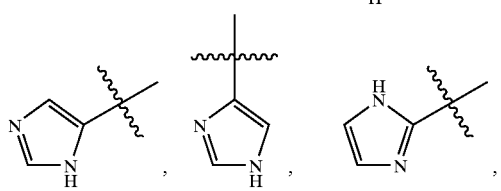

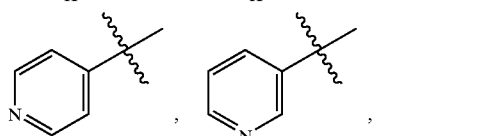

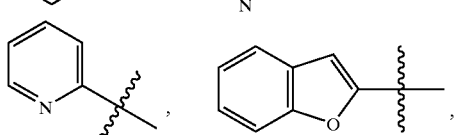

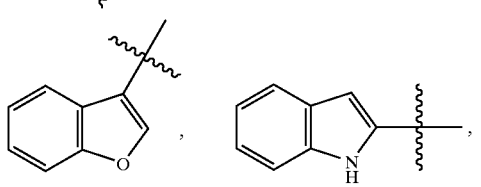

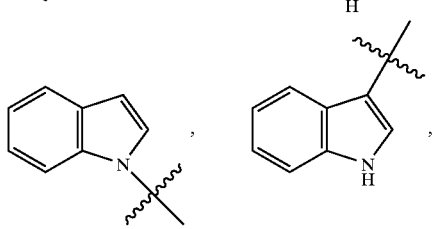

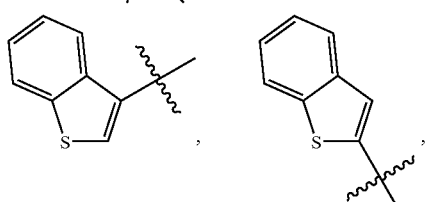

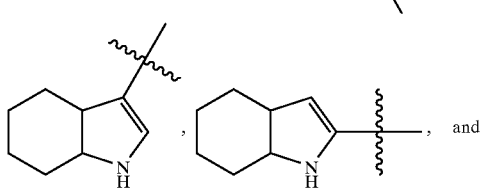

-continued

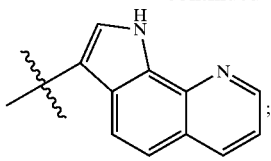

alternatively $R^2$ and $R^3$ can combine to form —$(CH_2)_2$N$(CH_3)(CH_2)_2$—.

9. The compound according to claim 8 wherein $R^4$ is selected from F, Cl, Br, I, OH, $NO_2$, CN, $CF_3$, methyl, ethyl, propyl, iso-propyl, butyl, sec-butyl, t-butyl, pentyl, ethenyl, propenyl, butenyl, ethynyl, propynyl, butynyl, methoxy, ethoxy, n-propoxy, i-propoxy, n-butoxy, s-butoxy, t-butoxy, phenyl, cyclopropyl, cyclobutyl, cyclopentyl, cyclohexyl, $CO_2H$, formyl, acetyl, propanoyl, butyryl, $NH_2$, mono-alkylamino, di-alkylamino, phenyl, and heteroaryl; and n is selected from 0, 1, and 2.

10. The compound according to claim 1 wherein Het is selected from:

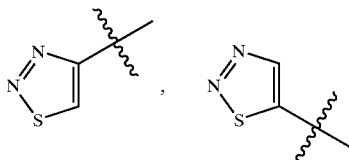

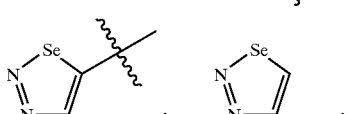

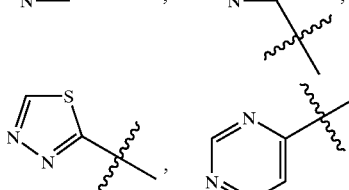

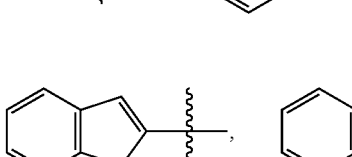

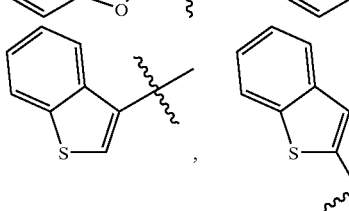

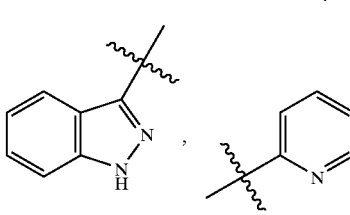, and

-continued
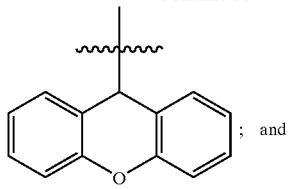; and
R² and R³ are independently selected from:
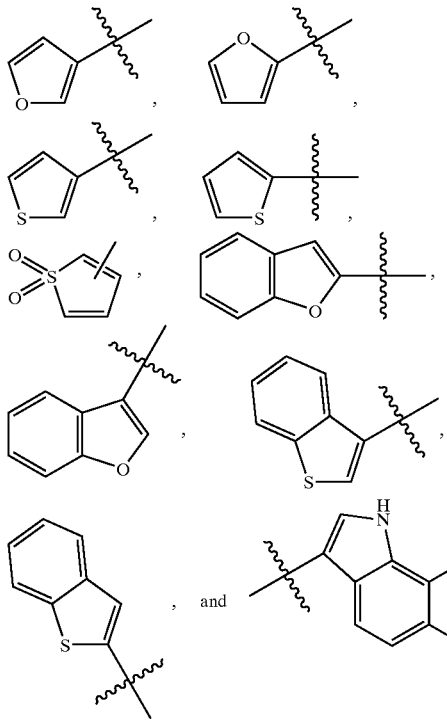
alternatively R² and R³ can combine to form —(CH₂)₂N(CH₃)(CH₂)₂—.
11. A compound of the formula:
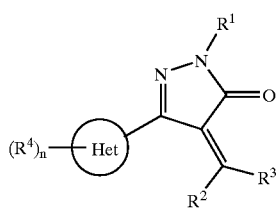
or a stereoisomer or pharmaceutically acceptable salt thereof, wherein: Het is a heterocycle selected from:
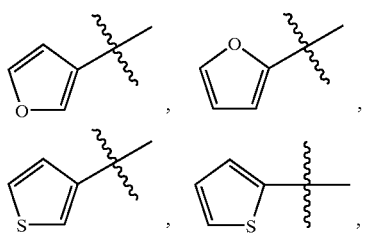
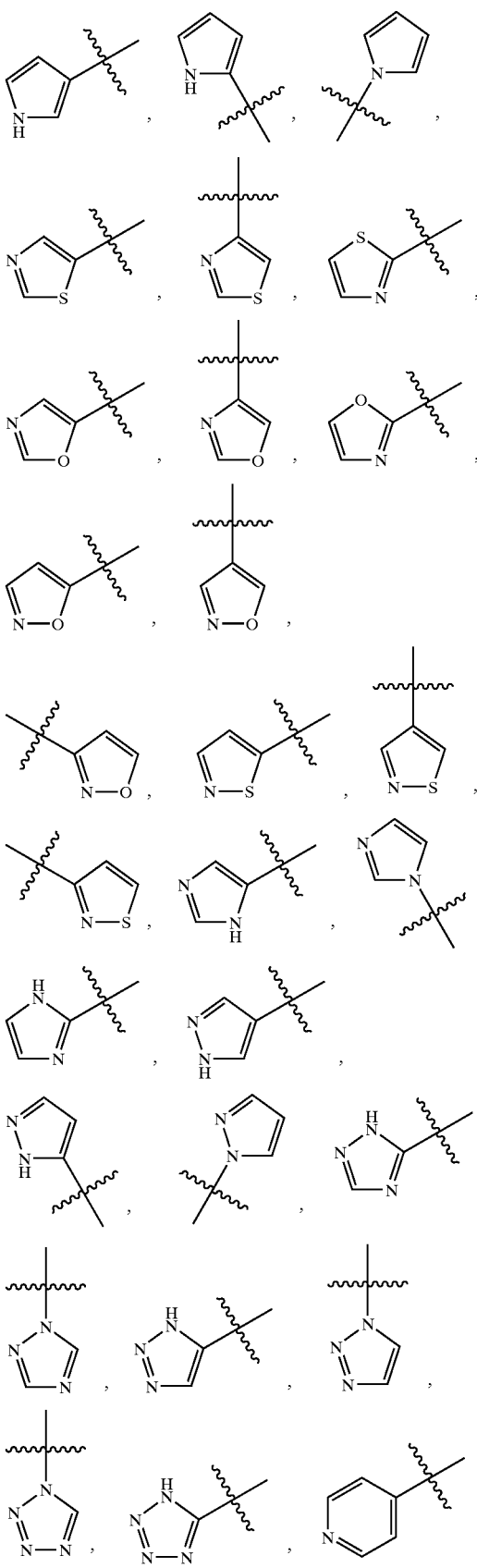

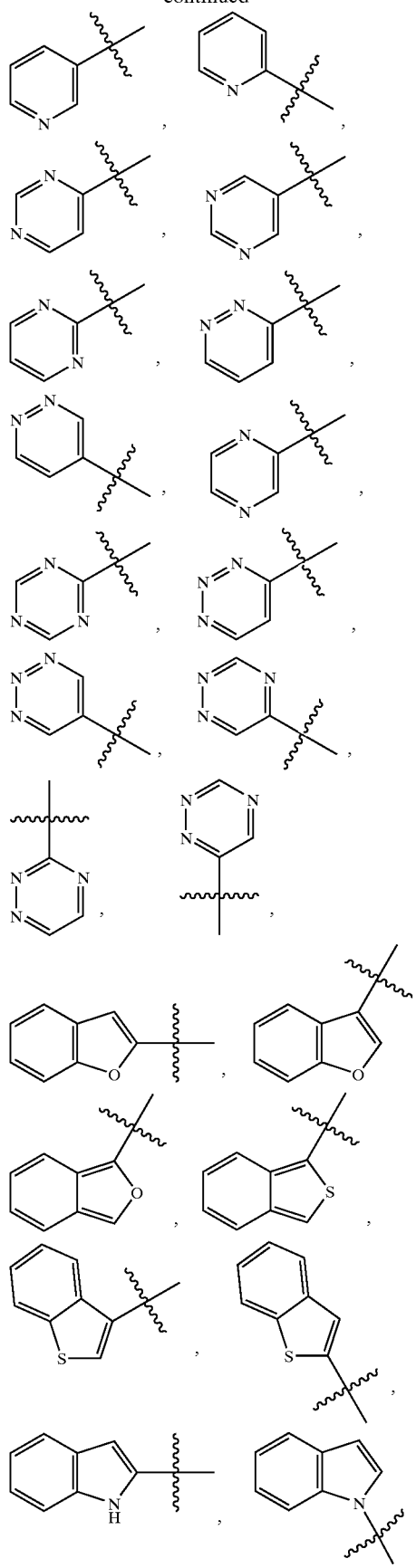
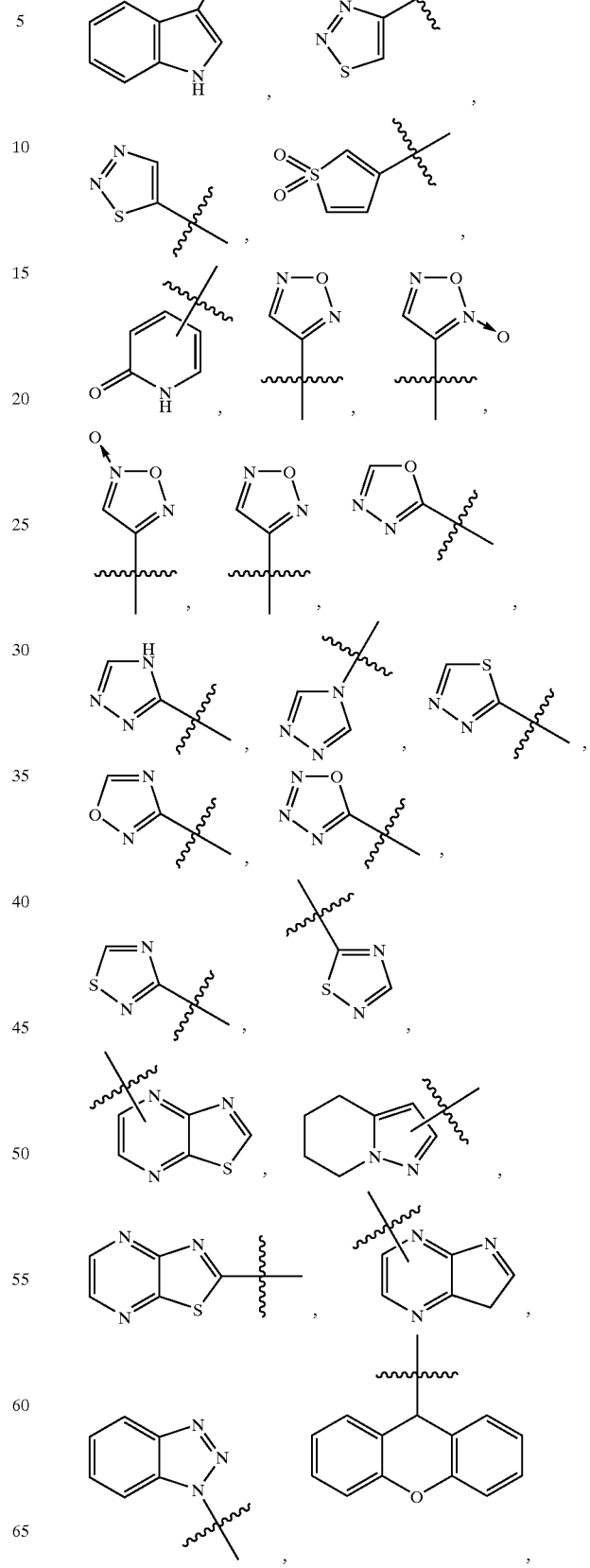

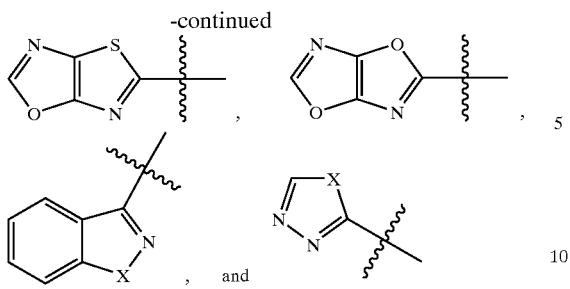

wherein X is selected from O, S, NH, and N-alkyl;

$R^1$ is selected from H, $C_{1-6}$ alkyl;

$R^2$ and $R^3$ are independently selected from H and $(CH_2)_r$heterocycle substituted with 0–5 $R^4$, with the proviso that both $R^2$ and $R^3$ cannot be H;

$R^4$ at each occurrence, is independently selected from H, F, Cl, Br, I, CN, $CF_2CF_3$, $CF_3$, $NO_2$, CN, OH, $NR^aR^a$, $OR^c$, $C(=O)R^b$, $CO_2R^c$, $OC(=O)R^b$, $NR^aC(=O)R^b$, $C(=O)NR^aR^a$, $OC(=O)NR^aR^a$, $NR^aC(=O)OR^b$, $NR^aS(=O)_2R^b$, $S(=O)_2NR^aR^a$, $NR^aC(=S)R^b$, $C(=S)NR^aR^a$, $NR^aC(=O)NR^aR^a$, $NR^aC(=S)NR^aR^a$, $CH=NOR^c$, $CH=NR^a$, $CH=NNR^aR^a$, $(CH_2)_rS(O)_pR^b$, $O(CH_2)_qNR^aR^a$, $O(CH_2)_qOR^c$, $(CH_2)_rOR^{d'}$, $(CH_2)_rC(=O)R^{d'}$, $(CH_2)_rNHR^d$, $(CH_2)_rS(O)_pR^{d'}$, $C_{1-10}$ alkyl substituted with 0–5 $R^6$, $C_{2-8}$ alkenyl substituted with 0–5 $R^6$, $C_{2-8}$ alkynyl substituted with 0–5 $R^6$, carbocycle substituted with 0–5 $R^6$, and heterocycle substituted with 0–5 $R^6$;

$R^6$, at each occurrence, is independently selected from $C_{1-6}$ alkyl substituted with 0–5 $R^h$, $C_{2-8}$ alkenyl substituted with 0–5 $R^h$, $C_{2-8}$ alkynyl substituted with 0–5 $R^h$, F, Cl, Br, I, CN, $CF_2CF_3$, $CF_3$, $NO_2$, CN, $NR^fR^f$, $OR^f$, $C(=O)R^f$, $CO_2R^f$, $OC(=O)R^g$, $NR^fC(=O)R^f$, $C(=O)NR^fR^f$, $OC(=O)NR^fR^f$, $NR^eC(=O)OR^g$, $NR^eS(=O)_2R^g$, $S(=O)_2NR^fR^f$, $NR^aC(=S)R^g$, $C(=S)NR^fR^f$, $NR^fC(=O)NR^fR^f$, $NR^fC(=S)NR^fR^f$, $CH=NOR^e$, $CH=NR^e$, $CH=NNR^eR^e$, $S(O)_pR^f$, $O(CH_2)_pNR^fR^f$, $O(CH_2)_pOR^f$, $OR^{d'}$, $NHR^d$, $C(=O)R^{d'}$, $S(O)_pR^{d'}$, carbocycle substituted with 0–5 $R^h$, heterocycle substituted with 0–5 $R^h$, $P(=O)(OR^c)_2$, and a $C_{5-7}$ monosaccharide wherein each hydroxyl group of the monosaccharide is unsubstituted or replaced by a group selected from H, $C_{1-4}$ alkyl, $C_{1-4}$ alkoxy, and $OC(=O)C_{1-4}$ alkyl;

$R^a$, at each occurrence, is independently selected from H, $C_{1-6}$ alkyl, $C_{2-6}$ alkenyl, $C_{2-6}$ alkynyl, $(CH_2)_rC_{3-6}$ cycloalkyl, and $(CH_2)_r$phenyl, wherein when $R^a$ is other than H, $R^a$ is substituted with 0–5 $R^h$;

alternatively, two $R^a$ may join to form a linker selected from $(CH_2)_qO(CH_2)_q$, $(CH_2)_qS(CH_2)_q$, and $(CH_2)_m$, wherein the linker is substituted with 0–5 $R^h$;

$R^b$, at each occurrence, is independently selected from $C_{1-6}$ alkyl, $C_{2-6}$ alkenyl, $C_{2-6}$ alkynyl, $(CH_2)_r$phenyl, and $(CH_2)_r$heterocycle, wherein $R^b$ is substituted with 0–5 $R^h$;

$R^c$, at each occurrence, is independently selected from H, $C_{1-6}$ alkyl, $C_{2-6}$ alkenyl, $C_{2-6}$ alkynyl, $C_{3-6}$ cycloalkyl, and $(CH_2)_r$phenyl, wherein when $R^c$ is other than H, $R^c$ is substituted with 0–5 $R^h$;

$R^d$, at each occurrence, is independently selected from the residue of an amino acid after the hydroxyl group of the carboxyl group is removed;

$R^{d'}$, at each occurrence, is independently selected from the residue of an amino acid after the hydrogen of the amine is removed;

$R^e$, at each occurrence, is independently selected from H and $C_{1-6}$ alkyl;

$R^f$, at each occurrence, is selected from H, $C_{1-6}$ alkyl substituted with 0–5 $R^h$, and $(CH_2)_r$phenyl substituted with 0–5 $R^h$;

$R^g$, at each occurrence, is independently selected from $C_{1-6}$ alkyl substituted with 0–5 $R^h$ and $(CH_2)_r$phenyl substituted with 0–5 $R^h$;

$R^h$, at each occurrence, is selected from F, Cl, Br, I, OH, $NO_2$, CN, $CF_3$, $CF_2CF_3$, $C_{1-4}$ alkyl, $C_{2-6}$ alkenyl, $C_{2-6}$ alkynyl, alkoxy, $C_{3-7}$ cycloalkyl, carboxyl, formyl, acetyl, propanoyl, butyryl, valeryl, pivaloyl, hexanoyl, acetamido, carbamyl, $NH_2$, monoalkylamino, dialkylamino, phenyl, benzyl, phenethyl, naphthyl, heterocycle, and keto;

$R^i$, at each occurrence, is selected from F, Cl, Br, I, OH, $NO_2$, CN, $CF_3$, $CF_2CF_3$, $C_{1-4}$ alkyl, $C_{2-6}$ alkenyl, $C_{2-6}$ alkynyl, alkoxy, $C_{3-7}$ cycloalkyl, carboxyl, formyl, acetyl, propanoyl, butyryl, valeryl, pivaloyl, hexanoyl, acetamido, carbamyl, $NH_2$, monoalkylamino, dialkylamino, phenyl, benzyl, and phenethyl;

m, at each occurrence, is independently selected from 2, 3, 4, and 5;

n, at each occurrence, is independently is selected from 0, 1, 2, 3, 4, and 5;

p, at each occurrence, is independently selected from 0, 1, and 2;

q, at each occurrence, is independently selected from 1, 2, 3, and 4; and r, at each occurrence, is independently selected from 0, 1, 2, 3 and 4.

12. The compound according to claim 11 wherein $R^2$ and $R^3$ are independently selected from:

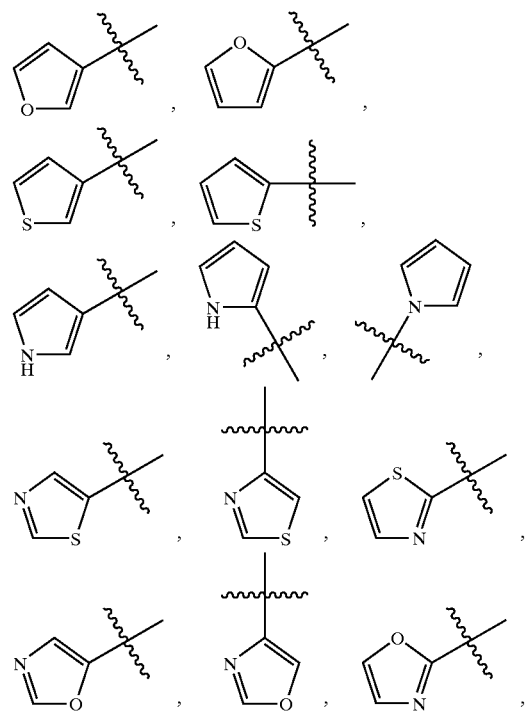

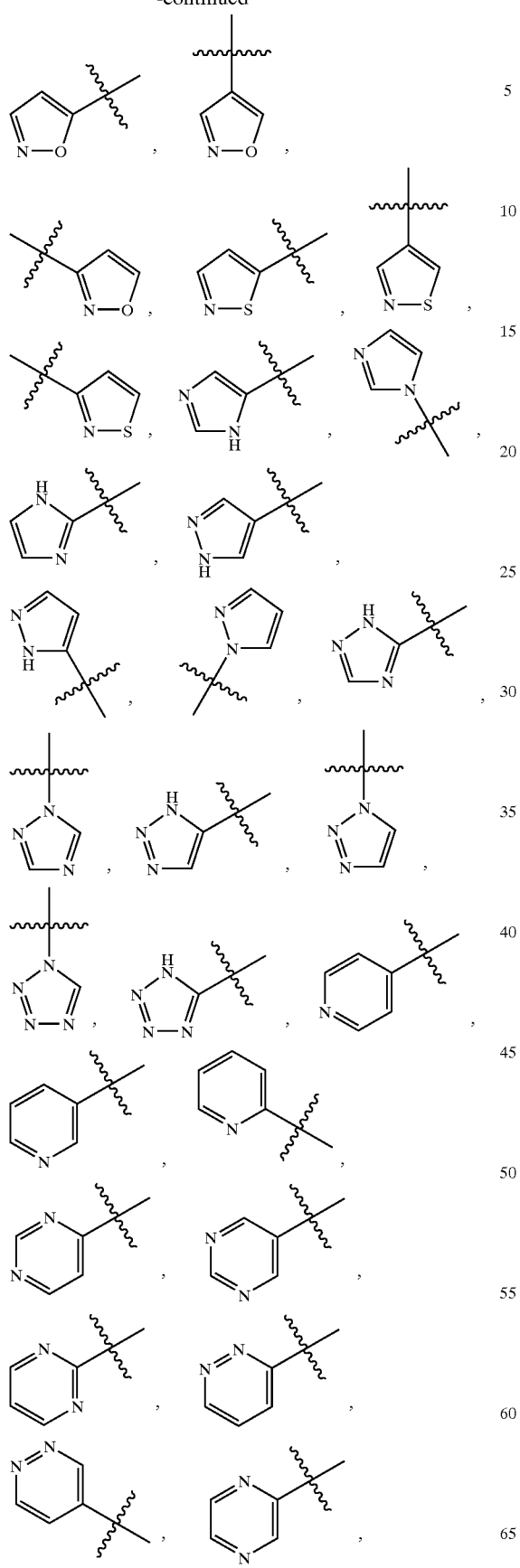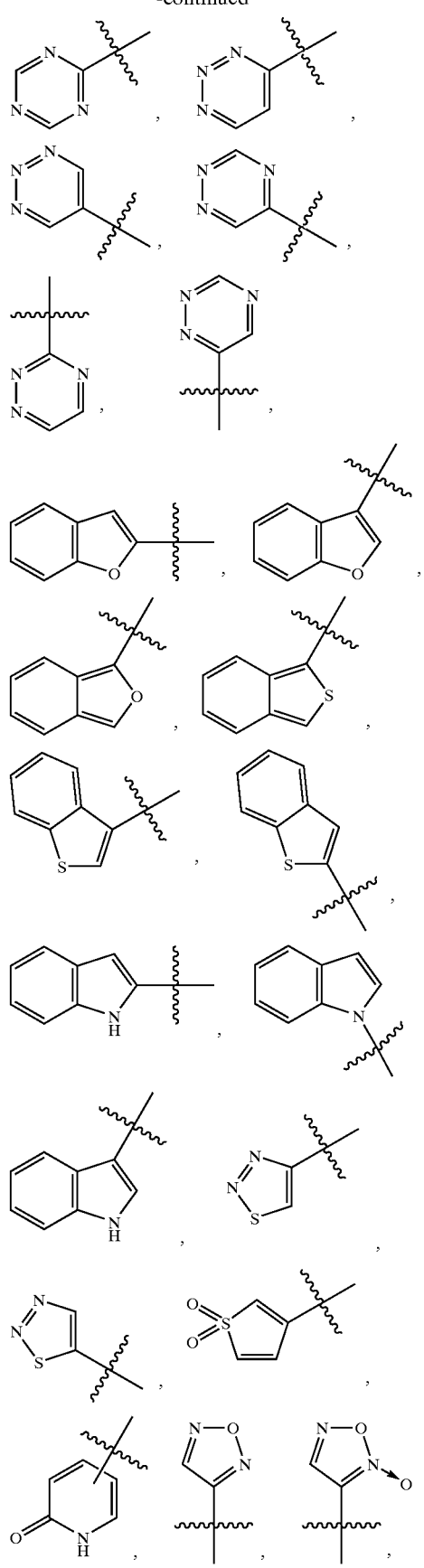

-continued
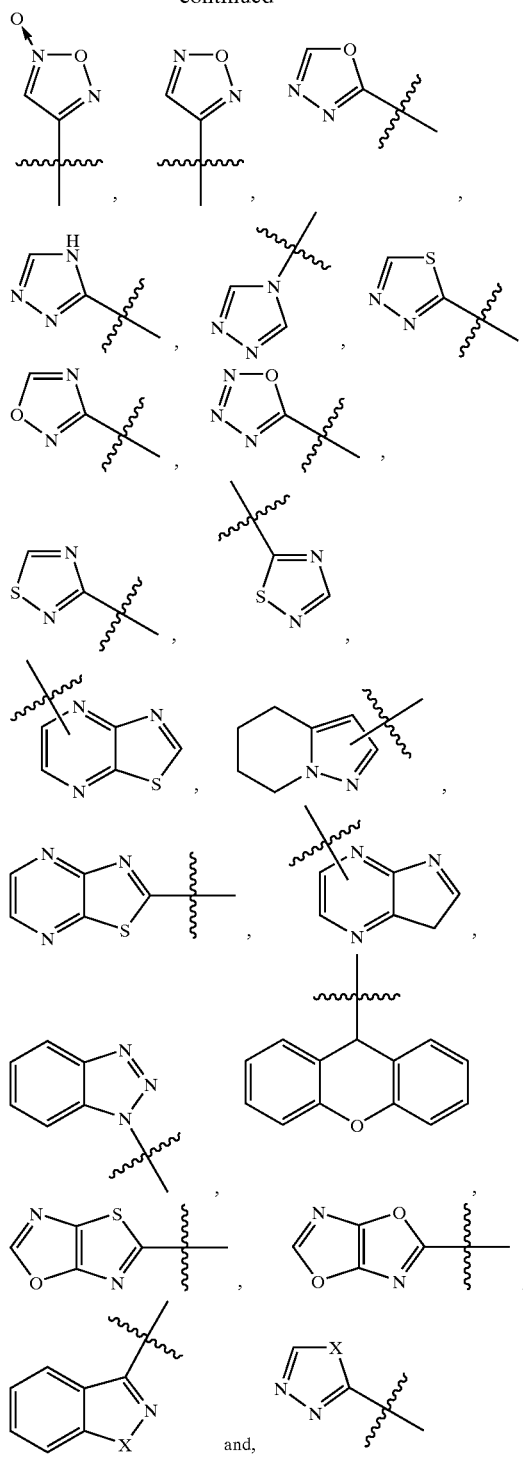
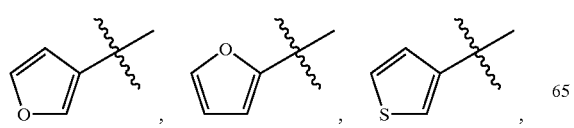
wherein X is selected from O, S, NH, and N-alkyl.
13. A compound according to claim 11 wherein Het is selected from:
-continued
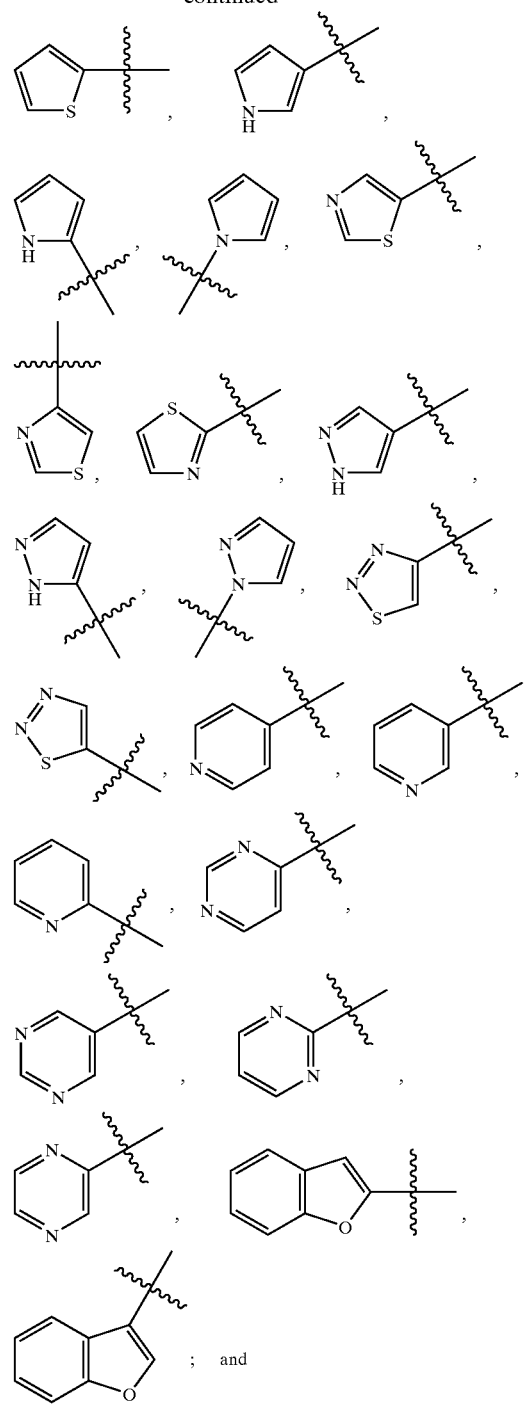
$R^2$ and $R^3$ are independently selected from:
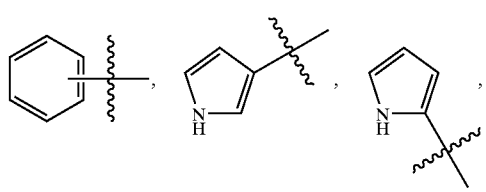

-continued

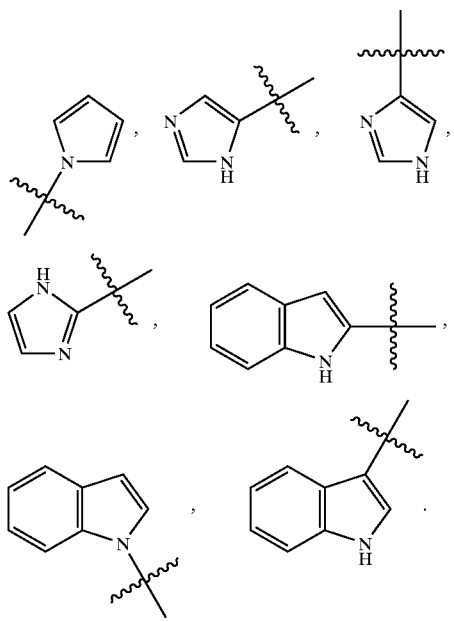

14. The compound according to claim 13 wherein $R^4$ is selected from F, Cl, Br, I, OH, $NO_2$, CN, $CF_3$, methyl, ethyl, propyl, iso-propyl, butyl, sec-butyl, t-butyl, pentyl, ethenyl, propenyl, butenyl, ethynyl, propynyl, butynyl, methoxy, ethoxy, n-propoxy, i-propoxy, n-butoxy, s-butoxy, t-butoxy, phenyl, cyclopropyl, cyclobutyl, cyclopentyl, cyclohexyl, $CO_2H$, formyl, acetyl, propanoyl, butyryl, $NH_2$, mono-alkylamino, di-alkylamino, phenyl, and heteroaryl; and n is selected from 0, 1, and 2.

15. The compound according to claim 11 wherein Het is selected from:

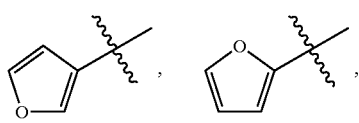

-continued

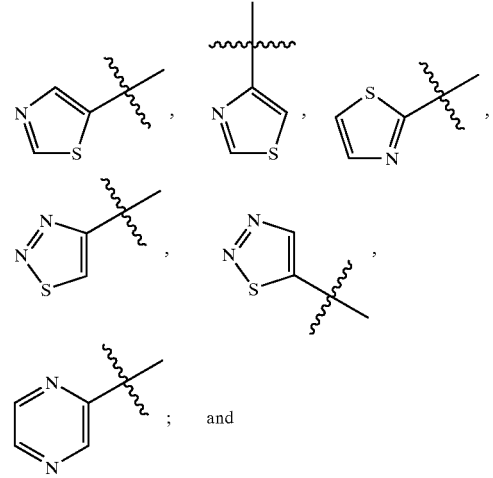

; and $R^2$ and $R^3$ are independently selected from:

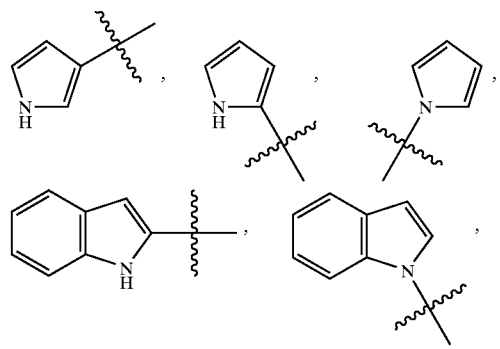

16. A compound selected in accordance with the following table:

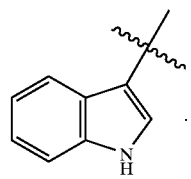

| Compound No. | $R^2$ | $R^3$ | $R^4$-(Het) |
|---|---|---|---|
| 1 | H | 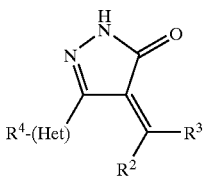 | 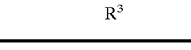 |

-continued
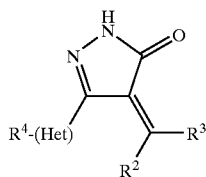
| Compound No. | R² | R³ | R⁴-(Het) |
|---|---|---|---|
| 4 | H | X₃-CH=C(Ph)(Ph) | 3-furyl-X₄ |
| 5 | H | ethyl/methyl-substituted pyrrole-2-carboxylate benzyl ester with X₃ | 3-furyl-X₄ |
| 6 | H | diiodo-methyl pyrrole with X₃ | 3-furyl-X₄ |
| 7 | H | pyrrole with ethyl ester, ethyl acetate and ethyl propanoate substituents, X₃ | 3-furyl-X₄ |
| 8 | H | 3,4-dibromo-5-methyl pyrrole with X₃ | 3-furyl-X₄ |
| 9 | H | 1H-indol-3-yl with X₃ | 3-furyl-X₄ |

-continued
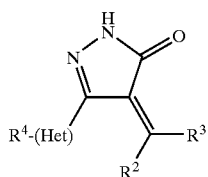
| Compound No. | R² | R³ | R⁴-(Het) |
|---|---|---|---|
| 11 | H | X₃-(5-methoxy-1H-indol-3-yl) | 3-furyl-X₄ |
| 12 | H | X₃-(1H-pyrrol-2-yl) | 3-furyl-X₄ |
| 15 | H | X₃-(1H-imidazol-2-yl) | 3-furyl-X₄ |
| 16 | H | X₃-(6-methoxycarbonyl-1H-indol-3-yl) | 3-furyl-X₄ |
| 17 | H | X₃-(5-chloro-1H-indol-3-yl) | 3-furyl-X₄ |
| 18 | H | X₃-(4-benzyloxy-1H-indol-3-yl) | 3-furyl-X₄ |

-continued

|  |  |  |  |
|---|---|---|---|
| Compound No. | R² | R³ | R⁴-(Het) |
| 19 | H | 5-fluoro-1H-indol-3-yl (X₃ at 3-position) | furan-3-yl (X₄) |
| 20 | H | 1-methyl-1H-indol-3-yl (X₃ at 3-position) | furan-3-yl (X₄) |
| 21 | H | 5-benzyloxy-1H-indol-3-yl (X₃ at 3-position) | furan-3-yl (X₄) |
| 22 | H | 7-methyl-1H-indol-3-yl (X₃ at 3-position) | furan-3-yl (X₄) |
| 27 | H | 2,5-dimethyl-1H-pyrrol-3-yl (X₃ at 3-position, 4-CH₃) | 2,4-dimethylfuran-3-yl (X₄) |
| 28 | H | 2-methyl-1H-pyrrol-3-yl (X₃, 4-CH₃) | furan-2-yl (X₄) |
| 29 | H | 1H-indol-3-yl (X₃ at 3-position) | furan-2-yl (X₄) |

-continued
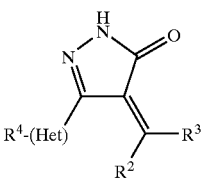
| Compound No. | R² | R³ | R⁴-(Het) |
|---|---|---|---|
| 36 | H | 2,4-dimethyl-1H-pyrrol-3-yl (X₃ at 2-position, NH, CH₃ at 5, H₃C at 3) | 2,5-dimethylfuran-3-yl (X₄ at 3, CH₃ at 5, H₃C at 2) |
| 41 | H | 2,4-dimethyl-1H-pyrrol-3-yl | 5-(4-chlorophenyl)-2-methylfuran-3-yl (X₄) |
| 42 | H | 1H-indol-3-yl (X₃) | 5-(4-chlorophenyl)-2-methylfuran-3-yl (X₄) |
| 43 | H | 5-(benzyloxy)-1H-indol-3-yl (X₃) | furan-2-yl (X₄) |
| 44 | H | 4-(benzyloxy)-1H-indol-3-yl (X₃) | furan-2-yl (X₄) |
| 45 | H | 1-methyl-1H-indol-3-yl (X₃) | furan-2-yl (X₄) |

-continued
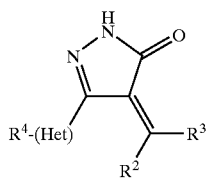
| Compound No. | R² | R³ | R⁴-(Het) |
|---|---|---|---|
| 46 | H | X₃-(3-yl)-6-methyl-1H-indole | 2-furyl-X₄ |
| 47 | H | X₃-(3-yl)-7-methyl-1H-indole | 2-furyl-X₄ |
| 48 | H | X₃-(3-yl)-5-fluoro-1H-indole | 2-furyl-X₄ |
| 49 | H | X₃-(3-yl)-5-chloro-1H-indole | 2-furyl-X₄ |
| 50 | H | X₃-(3-yl)-6-(methoxycarbonyl)-1H-indole | 2-furyl-X₄ |
| 51 | H | X₃-(3-yl)-5-methoxy-1H-indole | 2-furyl-X₄ |

-continued
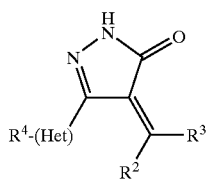
| Compound No. | R² | R³ | R⁴-(Het) |
|---|---|---|---|
| 52 | H | X₃-C₆H₄-N(CH₃)₂ | 2-furyl-X₄ |
| 53 | H | 4-methyl-5-X₃-1H-imidazol-yl | 2-furyl-X₄ |
| 54 | H | 2-X₃-1H-imidazol-yl | 2-furyl-X₄ |
| 57 | H | 2-methyl-4-X₃-3-methyl-1H-pyrrol-yl | 2-benzofuryl-X₄ |
| 58 | H | 3-X₃-1H-indol-yl | 2-benzofuryl-X₄ |
| 59 | H | 3-X₃-1-methyl-1H-indol-yl | 2-benzofuryl-X₄ |
| 65 | H | 3-X₃-1-(2-cyanoethyl)-1H-indol-yl | 3-furyl-X₄ |
| 67 | H | 3-X₃-1-(2-cyanoethyl)-1H-indol-yl | 2-furyl-X₄ |

-continued
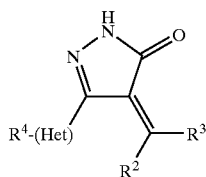
| Compound No. | R² | R³ | R⁴-(Het) |
|---|---|---|---|
| 68 | H | X₃-(1-benzyl-indol-3-yl) | 3-furyl-X₄ |
| 69 | H | X₃-(1-benzyl-indol-3-yl) | 2-furyl-X₄ |
| 71 | H | X₃-[1-(2-benzyloxyethyl)-indol-3-yl] | 2-furyl-X₄ |
| 91 | H | X₃-(4-chlorophenyl) | 2-furyl-X₄ |
| 92 | H | X₃-(3,4-dichlorophenyl) | 2-furyl-X₄ |
| 93 | H | X₃-(3,5-dimethoxyphenyl) | 2-furyl-X₄ |
| 94 | H | X₃-(2,5-dimethoxyphenyl) | 2-furyl-X₄ |
| 95 | H | X₃-(4-fluorophenyl) | 2-furyl-X₄ |

-continued
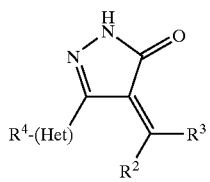
| Compound No. | R² | R³ | R⁴-(Het) |
|---|---|---|---|
| 98 | H | 3-X₃-phenyl with OH | 2-X₄-furan |
| 99 | H | 2-X₃-4-nitro-phenol | 2-X₄-furan |
| 100 | H | 3-X₃-4-nitro-phenol | 2-X₄-furan |
| 101 | H | 4-X₃-1-methoxynaphthalene | 2-X₄-furan |
| 106 | H | 3-X₃-1-methyl-5-fluoroindole | 2-X⁴-furan |
| 107 | H | 3-X₃-1-methyl-5-chloroindole | 2-X₄-furan |

-continued
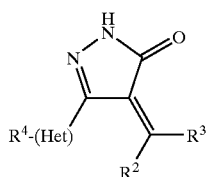
| Compound No. | R² | R³ | R⁴-(Het) |
|---|---|---|---|
| 108 | H | X₃-substituted 1-methyl-5-fluoro-indol-3-yl | 3-furyl-X₄ |
| 122 | H | X₃-(4-ethylphenyl) | 2-furyl-X₄ |
| 123 | H | X₃-(4-methylthiophenyl) | 2-furyl-X₄ |
| 124 | | R² and R³ combined to form: X₃-(1-methylpiperidin-4-ylidene) | 2-furyl-X₄ |
| 125 | H | X₃-(thiophen-2-yl) | 2-furyl-X₄ |
| 126 | H | X₃-(4-trifluoromethylphenyl) | 2-furyl-X₄ |
| 287 | H | X₃-substituted 1-methyl-4-bromo-5-fluoro-indol-3-yl | 2-furyl-X₄ | wherein $X^3$ and $X^4$ are the attachment point for substituents $R^3$ and $R^4$, respectively.
17. A compound in accordance with the following table:
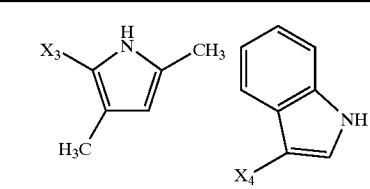
| Compound No. | $R^2$ | $R^3$ | Het |
|---|---|---|---|
| 77 | H | 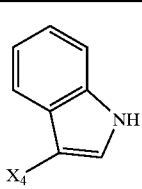 | 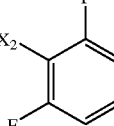 |
| 78 | 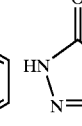 | 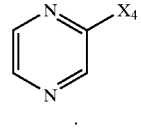 | 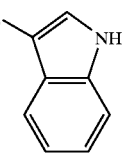 |
18. A compound selected in accordance with the following table:
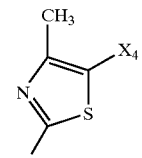
| Compound No. | $R^2$ | $R^3$ | $R^4$-(Het) |
|---|---|---|---|
| 13 | H | 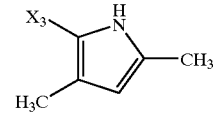 | 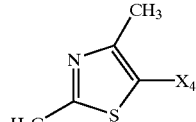 |
| 14 | H | 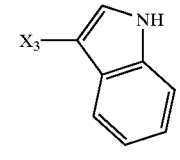 | 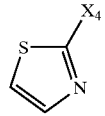 |
| 25 | H | 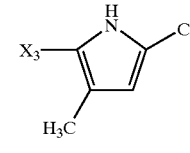 | 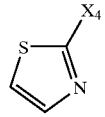 |
| 26 | H |  |  |

-continued

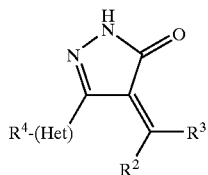

| Compound No. | R² | R³ | R⁴-(Het) |
|---|---|---|---|
| 40 | H | (1H-pyrrole, 2,5-dimethyl, X₃ at 2-position) | (2-phenyl-thiazole, X₄ at 4-position) |
| 60 | H | (1-methyl-indole, X₃ at 3-position) | (thiazole, X₄ at 2-position) |
| 64 | H | (1-(2-cyanoethyl)-indole, X₃ at 3-position) | (thiazole, X₄ at 2-position) |
| 70 | H | (1-benzyl-indole, X₃ at 3-position) | (thiazole, X₄ at 2-position) |
| 72 | H | (1-(2-benzyloxyethyl)-indole, X₃ at 3-position) | (thiazole, X₄ at 2-position) |
| 73 | H | (1-isobutyl-indole, X₃ at 3-position) | (thiazole, X₄ at 2-position) |
| 86 | H | (1-methyl-5-fluoro-indole, X₃ at 3-position) | (thiazole, X₄ at 2-position) |

-continued
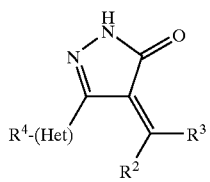
| Compound No. | R² | R³ | R⁴-(Het) |
|---|---|---|---|
| 87 | H | 3-X₃-4-nitro-6-hydroxyphenyl | 2-X₄-thiazole |
| 90 | H | 2-X₃-6-bromophenyl | 2-X₄-thiazole |
| 105 | H | 3-X₃-1-methyl-5-chloroindole | 2-X₄-thiazole |
| 113 | H | 3-X₃-1-methyl-6-fluoroindole | 2-X₄-thiazole |
| 115 | H | 3-X₃-1-methyl-6-(methoxycarbonyl)indole | 2-X₄-thiazole |
| 117 | H | 2-X₃-3,5-dimethyl-1H-pyrrole | 4-(naphthalen-2-yl)-2-X₄-thiazole |

-continued
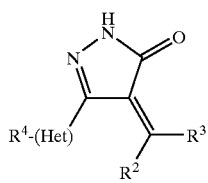
| Compound No. | R² | R³ | R⁴-(Het) |
|---|---|---|---|
| 118 | H | 1-methyl-indol-3-yl (X₃) | 2-(naphthalen-2-yl)thiazol-4-yl linked via X₄ |
| 130 | H | 1-methyl-5-cyano-indol-3-yl (X₃) | thiazol-2-yl (X₄) |
| 132 | H | 1-ethyl-indol-3-yl (X₃) | thiazol-2-yl (X₄) |
| 137 | H | 1-methyl-4-fluoro-indol-3-yl (X₃) | thiazol-2-yl (X₄) |
| 142 | H | 1-methyl-4-methoxy-indol-3-yl (X₃) | thiazol-2-yl (X₄) |
| 143 | H | 1-methyl-4-chloro-indol-3-yl (X₃) | thiazol-2-yl (X₄) |

-continued
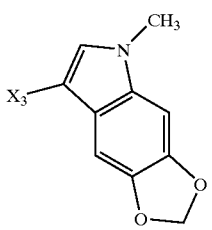
| Compound No. | R² | R³ | R⁴-(Het) |
|---|---|---|---|
| 144 | H | 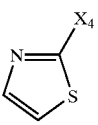 | 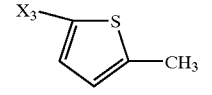 |
| 153 | H | 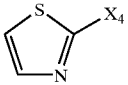 | 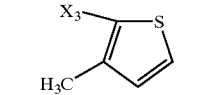 |
| 154 | H | 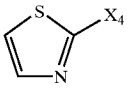 | 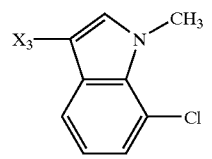 |
| 163 | H | 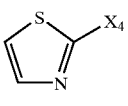 | 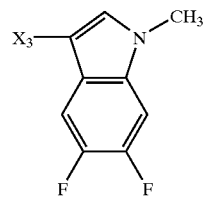 |
| 164 | H | 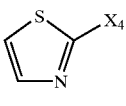 | 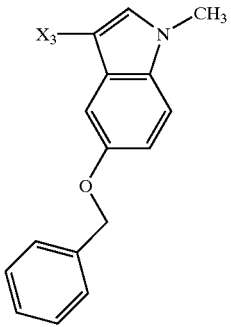 |
| 166 | H | 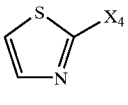 | 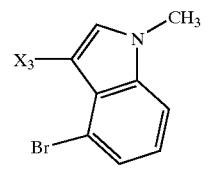 |
| 177 | H | 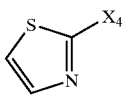 | |

-continued
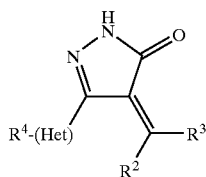
| Compound No. | R² | R³ | R⁴-(Het) |
|---|---|---|---|
| 181 | H | 1-methyl-3-X₃-4-nitro-5-methoxyindole | 2-X₄-thiazole |
| 221 | H | 1-methyl-3-X₃-4-bromo-5-fluoroindole | 2-X₄-thiazole |
| 223 | H | 1-methyl-3-X₃-4-iodo-6-methylindole | 2-X₄-thiazole |
| 225 | H | 1-methyl-3-X₃-4-bromo-6-methylindole | 2-X₄-thiazole |
| 226 | H | 1-methyl-3-X₃-4-bromo-6-methylindole | 5-X₄-1,2,3-thiadiazole |
| 232 | H | 1-methyl-3-X₃-5-(prop-2-ynyloxy)indole | 2-X₄-thiazole |

-continued
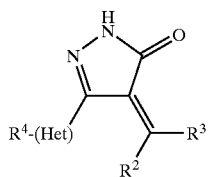
| Compound No. | R² | R³ | R⁴-(Het) |
|---|---|---|---|
| 234 | H | 1-methyl-4-ethoxy-indol-3-yl (X₃) | thiazol-2-yl (X₄) |
| 242 | H | 1-methyl-4-methyl-indol-3-yl (X₃) | thiazol-2-yl (X₄) |
| 243 | H | 1-methyl-6-methyl-indol-3-yl (X₃) | thiazol-2-yl (X₄) |
| 246 | H | 1-methyl-6-methoxy-indol-3-yl (X₃) | thiazol-2-yl (X₄) |
| 253 | H | 1-methyl-5-nitro-indol-3-yl (X₃) | thiazol-2-yl (X₄) |
| 254 | H | 1-methyl-7-methyl-indol-3-yl (X₃) | thiazol-2-yl (X₄) |

-continued
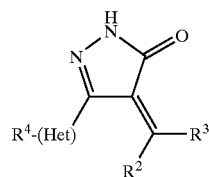
| Compound No. | R² | R³ | R⁴-(Het) |
|---|---|---|---|
| 255 | H | 1-methyl-3-X₃-indoline-5-carboxylic acid | 2-X₄-thiazole |
| 256 | H | 1-methyl-6-methyl-3-X₃-indole | 2-X₄-thiazole |
| 257 | H | 6-chloro-3-X₃-1H-indole | 2-X₄-thiazole |
| 258 | H | methyl 3-X₃-1H-indole-5-carboxylate | 2-X₄-thiazole |
| 259 | H | 1-methyl-5-methoxy-3-X₃-indole | 2-X₄-thiazole |

-continued
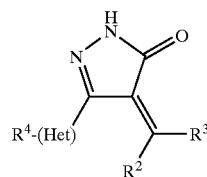
| Compound No. | R² | R³ | R⁴-(Het) |
|---|---|---|---|
| 260 | H | 4-ethoxy-1H-indol-3-yl (X₃) | thiazol-2-yl (X₄) |
| 274 | H | 4,7-dimethoxy-1-methyl-1H-indol-3-yl (X₃) | thiazol-2-yl (X₄) |
| 276 | H | 4,5,6,7-tetrahydro-1H-indol-2-yl (X₃) | thiazol-2-yl (X₄) |
| 278 | H | 4-hydroxy-5-methoxy-1-methyl-1H-indol-3-yl (X₃) | thiazol-2-yl (X₄) |
| 279 | H | 4-bromo-5-methoxy-1-methyl-1H-indol-3-yl (X₃) | thiazol-2-yl (X₄) |

-continued
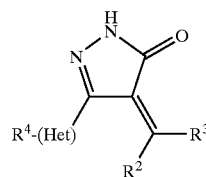
| Compound No. | R² | R³ | R⁴-(Het) |
|---|---|---|---|
| 280 | H | X₃-(3-position of 1-methyl-6-bromoindole) | 2-thiazolyl-X₄ |
| 281 | H | X₃-(3-position of 7-methoxyindole) | 2-thiazolyl-X₄ |
| 282 | H | X₃-(3-position of 1-methyl-7-methoxyindole) | 2-thiazolyl-X₄ |
| 284 | H | X₃-(3-position of 1-methyl-pyrrolo[3,2-h]quinoline) | 2-thiazolyl-X₄ |
| 296 | H | X₃—N(CH₃)₂ | 2-thiazolyl-X₄ |
| 297 | H | X₃-(3-position of 2-hydroxyindole) | 2-thiazolyl-X₄ | wherein $X^3$ and $X^4$ are the attachment point for substituents $R^3$ and $R^4$, respectively.
19. A compound selected in accordance with the following table:
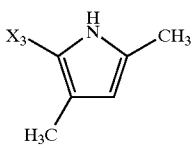
| Compound No. | $R^2$ | $R^3$ | $R^4$-(Het) |
|---|---|---|---|
| 82 | H | 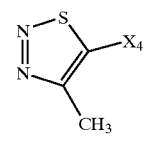 | 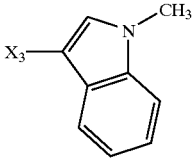 |
| 83 | H | 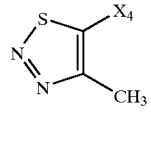 | 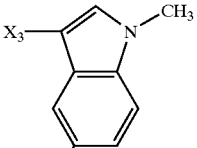 |
| 97 | H | 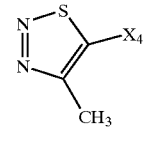 | 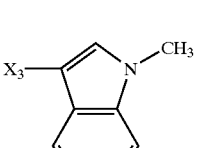 |
| 104 | H | 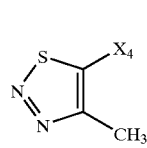 | 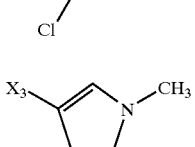 |
| 114 | H | 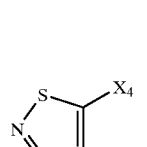 | 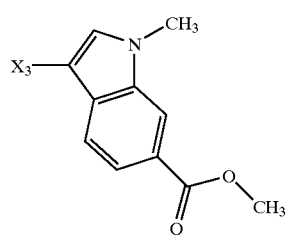 |
| 116 | H | 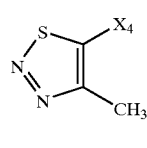 | |

-continued
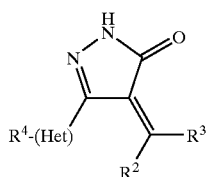
| Compound No. | R² | R³ | R⁴-(Het) |
|---|---|---|---|
| 172 | H | 1-methyl-4-bromo-indol-3-yl ($X_3$) | 4-methyl-1,2,3-thiadiazol-5-yl ($X_4$) |
| 173 | H | 1-methyl-4-fluoro-indol-3-yl ($X_3$) | 4-methyl-1,2,3-thiadiazol-5-yl ($X_4$) |
| 174 | H | 1H-indol-3-yl ($X_3$) | 4-methyl-1,2,3-thiadiazol-5-yl ($X_4$) |
| 175 | H | 5-chloro-1H-indol-3-yl ($X_3$) | 4-methyl-1,2,3-thiadiazol-5-yl ($X_4$) |
| 179 | H | 4,7-dimethoxy-1H-indol-3-yl ($X_3$) | 4-methyl-1,2,3-thiadiazol-5-yl ($X_4$) |
| 182 | H | 1-methyl-4-nitro-5-methoxy-indol-3-yl ($X_3$) | 4-methyl-1,2,3-thiadiazol-5-yl ($X_4$) |

-continued

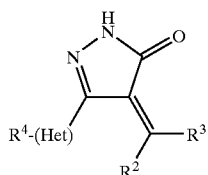

| Compound No. | R² | R³ | R⁴-(Het) |
|---|---|---|---|
| 183 | H | X₃-(5-fluoro-1-methylindol-3-yl) | 1,2,3-thiadiazol-5-yl-X₄ |
| 186 | H | X₃-(4-chloro-1-methylindol-3-yl) | 1,2,3-thiadiazol-5-yl-X₄ |
| 187 | H | X₃-(4-chloro-1-methylindol-3-yl) | 4-methyl-1,2,3-thiadiazol-5-yl-X₄ |
| 188 | H | X₃-(5-fluoro-1-methylindol-3-yl) | 1,2,3-selenadiazol-5-yl-X₄ |
| 190 | H | X₃-(1-methylindol-3-yl) | 2-(dimethylamino)-1,3,4-thiadiazol-5-yl-X₄ |
| 191 | H | X₃-(5-fluoro-1-methylindol-3-yl) | 2-(dimethylamino)-1,3,4-thiadiazol-5-yl-X₄ |
| 192 | H | X₃-(4-chloro-1-methylindol-3-yl) | 1,2,3-selenadiazol-5-yl-X₄ |

-continued

| Compound No. | R² | R³ | R⁴-(Het) |
|---|---|---|---|
| 193 | H | 4-Br, 1-CH₃-indol-3-yl (X₃ at 3) | 1,2,3-thiadiazol-5-yl (X₄) |
| 194 | H | 5,6-diF, 1-CH₃-indol-3-yl (X₃ at 3) | 1,2,3-thiadiazol-5-yl (X₄) |
| 195 | H | 6-Cl, 1-CH₃-indol-3-yl (X₃ at 3) | 1,2,3-thiadiazol-5-yl (X₄) |
| 196 | H | 6-CH₃, 1-CH₃-indol-3-yl (X₃ at 3) | 1,2,3-thiadiazol-5-yl (X₄) |
| 197 | H | 4-Br, 1-CH₃-indol-3-yl (X₃ at 3) | 2-(N,N-dimethylamino)-1,3,4-thiadiazol-5-yl (X₄) |
| 198 | H | 4-Br, 1-CH₃-indol-3-yl (X₃ at 3) | 4-phenyl-1,2,3-thiadiazol-5-yl (X₄) |
| 201 | H | 4-CH₃, 1-CH₃-indol-3-yl (X₃ at 3) | 1,2,3-thiadiazol-5-yl (X₄) |

-continued

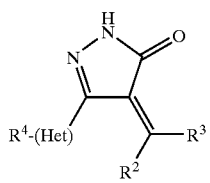

| Compound No. | R² | R³ | R⁴-(Het) |
|---|---|---|---|
| 204 | H | 2,4-dimethyl-pyrrole with X₃ | 5-(dimethylamino)-1,3,4-thiadiazole with X₄ |
| 209 | H | N-methyl-indole fused with methylenedioxy, X₃ | 1,2,3-thiadiazole with X₄ |
| 213 | H | N-methyl-4-iodo-5-fluoro-indole with X₃ | 4-methyl-1,2,3-thiadiazole with X₄ |
| 217 | H | N-methyl-4-iodo-6-methyl-indole with X₃ | 4-methyl-1,2,3-thiadiazole with X₄ |
| 218 | H | N-methyl-4-bromo-5-fluoro-indole with X₃ | 1,2,3-thiadiazole with X₄ |
| 220 | H | N-methyl-4-bromo-5-fluoro-indole with X₃ | 4-methyl-1,2,3-thiadiazole with X₄ |

-continued

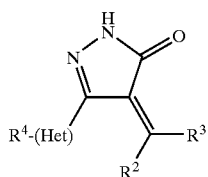

| Compound No. | R² | R³ | R⁴-(Het) |
|---|---|---|---|
| 224 | H | indole with X₃ at 3-position, N-CH₃, I at 4-position, CH₃ at 6-position | thiadiazole-X₄ |
| 226 | H | indole with X₃ at 3-position, N-CH₃, Br at 4-position, CH₃ at 6-position | thiadiazole-X₄ |
| 227 | H | indole with X₃ at 3-position, N-CH₃, Br at 4-position, CH₃ at 6-position | 4-methyl-thiadiazole-X₄ |
| 231 | H | indole with X₃ at 3-position, N-CH₃, CN at 5-position | thiadiazole-X₄ |
| 235 | H | indole with X₃ at 3-position, N-CH₃, OEt at 4-position | thiadiazole-X₄ |
| 236 | H | indole with X₃ at 3-position, N-CH₃, OEt at 4-position | 4-methyl-thiadiazole-X₄ |

-continued
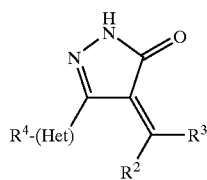
| Compound No. | R² | R³ | R⁴-(Het) |
|---|---|---|---|
| 238 | H | 3-X₃, 1-methylindole-5-carboxylic acid methyl ester | thiadiazole-X₄ |
| 239 | H | 3-X₃, 1-methylindole-5-carboxylic acid methyl ester | 4-methyl-thiadiazole-X₄ |
| 240 | H | 3-X₃, 1-methyl-5-(prop-2-ynyloxy)indole | thiadiazole-X₄ |
| 241 | H | 3-X₃, 5-bromo-1-methylindole | thiadiazole-X₄ |
| 244 | H | 3-X₃, 1-methyl-6-methylindole | thiadiazole-X₄ |

-continued
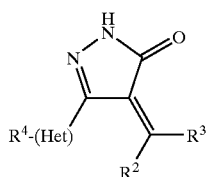
| Compound No. | R² | R³ | R⁴-(Het) |
|---|---|---|---|
| 245 | H | 3-indolyl, N-CH₃, 6-I, X₃ at 3-position | thiadiazole-X₄ |
| 247 | H | 3-indolyl, N-CH₃, 4-C(O)OCH₃, X₃ at 3-position | thiadiazole-X₄ |
| 248 | H | 3-indolyl, N-CH₃, 4-OCH₃, X₃ at 3-position | thiadiazole-X₄ |
| 249 | H | 3-indolyl, N-CH₃, 6-Cl, X₃ at 3-position | thiadiazole-X₄ |
| 250 | H | 3-indolyl, N-CH₃, 4-F, X₃ at 3-position | thiadiazole-X₄ |
| 252 | H | 3-indolyl, N-CH₃, 5-OCH₃, X₃ at 3-position | thiadiazole-X₄ |

-continued
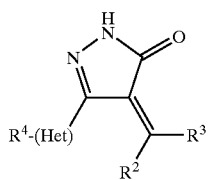
| Compound No. | R² | R³ | R⁴-(Het) |
|---|---|---|---|
| 261 | H | 3-X₃, 1-methyl-6-methoxyindole | 4-methyl-1,2,3-thiadiazol-5-yl (X₄) |
| 262 | H | 3-X₃, 5-methyl-methylenedioxyindole | 4-methyl-1,2,3-thiadiazol-5-yl (X₄) |
| 263 | H | 3-X₃, 1-methyl-6-cyanoindole | 4-methyl-1,2,3-thiadiazol-5-yl (X₄) |
| 264 | H | 3-X₃, 1-methyl-4-bromo-5-methoxyindole | 4-methyl-1,2,3-thiadiazol-5-yl (X₄) |
| 265 | H | 3-X₃, 1-methyl-4-bromo-5-methoxyindole | 1,2,3-thiadiazol-5-yl (X₄) |
| 266 | H | 3-X₃, 1-methyl-4-methylindole | 4-methyl-1,2,3-thiadiazol-5-yl (X₄) |

-continued

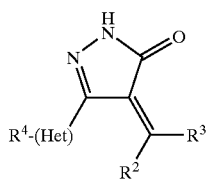

| Compound No. | R² | R³ | R⁴-(Het) |
|---|---|---|---|
| 267 | H | X₃-substituted 1-methyl-5-methoxyindol-3-yl | 4-methyl-1,2,3-thiadiazol-5-yl (X₄) |
| 268 | H | X₃-substituted 1-methyl-5-methylindol-3-yl | 4-methyl-1,2,3-thiadiazol-5-yl (X₄) |
| 269 | H | X₃-substituted 1-methyl-4-methoxyindol-3-yl | 4-methyl-1,2,3-thiadiazol-5-yl (X₄) |
| 270 | H | X₃-substituted 1-methyl-6-methylindol-3-yl | 4-methyl-1,2,3-thiadiazol-5-yl (X₄) |
| 272 | H | X₃-substituted 1-methyl-4,7-dimethoxyindol-3-yl | 4-methyl-1,2,3-thiadiazol-5-yl (X₄) |
| 273 | H | X₃-substituted 1-methyl-4,7-dimethoxyindol-3-yl | 1,2,3-thiadiazol-5-yl (X₄) |
| 277 | H | X₃-substituted 4,5,6,7-tetrahydroindol-2-yl | 4-methyl-1,2,3-thiadiazol-5-yl (X₄) |

-continued

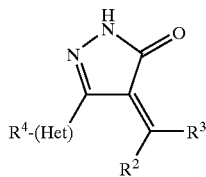

| Compound No. | R² | R³ | R⁴-(Het) |
|---|---|---|---|
| 283 | H | X₃—(1-methyl-7-methoxyindol-3-yl) | 4-methyl-1,2,3-thiadiazol-5-yl—X₄ |
| 285 | H | X₃—(1-methylpyrrolo-fused quinoline) | 4-methyl-1,2,3-thiadiazol-5-yl—X₄ |
| 286 | H | X₃—(4,5,6,7-tetrahydro-1H-indol-2-yl) | 1,2,3-thiadiazol-5-yl—X₄ | wherein X³ and X⁴ are the attachment point for substituents R³ and R⁴, respectively.

20. A compound selected in accordance with the following table:

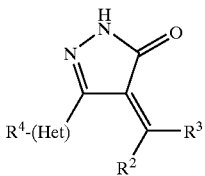

| Compound No. | R² | R³ | R⁴-(Het) |
|---|---|---|---|
| 74 | H | X₃—(2,4-dimethyl-1H-pyrrol-5-yl) | pyrazin-2-yl—X₄ |
| 79 | H | X₃—(2,6-dibromo-4-hydroxyphenyl) | pyrazin-2-yl—X₄ |

-continued

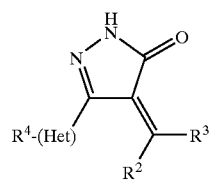

| Compound No. | R² | R³ | R⁴-(Het) |
|---|---|---|---|
| 80 | H | 2,4-dimethyl-1H-pyrrol-5-yl (X₃, H₃C, CH₃, NH) | quinoxalin-2-yl (X₄) |
| 81 | H | 1-methyl-1H-indol-3-yl (X₃, N-CH₃) | quinoxalin-2-yl (X₄) |
| 88 | H | 2,4-dimethyl-1H-pyrrol-5-yl (X₃, H₃C, CH₃, NH) | 3-methylpyrazin-2-yl (X₄, CH₃) |
| 89 | H | 1-methyl-1H-indol-3-yl (X₃, N-CH₃) | 3-methylpyrazin-2-yl (X₄, CH₃) |
| 102 | H | 2,4-dimethyl-1H-pyrrol-5-yl (X₃, H₃C, CH₃, NH) | 5-methylpyrazin-2-yl (X₄, H₃C) |
| 103 | H | 1-methyl-1H-indol-3-yl (X₃, N-CH₃) | 5-methylpyrazin-2-yl (X₄, H₃C) |
| 119 | H | 1-methyl-1H-indol-3-yl (X₃, N-CH₃) | pyrazin-2-yl (X₄) |

-continued
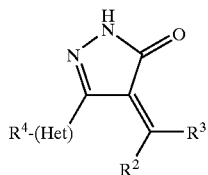
| Compound No. | R² | R³ | R⁴-(Het) |
|---|---|---|---|
| 120 | H | 3-(X₃)-1-methyl-5-fluoroindole | 2-(X₄)-pyrazine |
| 121 | H | 3-(X₃)-1-methyl-6-(methoxycarbonyl)indole | 2-(X₄)-pyrazine |
| 127 | H | 3-(X₃)-1-methyl-5-cyanoindole | 2-(X₄)-pyrazine |
| 128 | H | 3-(X₃)-1-methyl-5-chloroindole | 2-(X₄)-pyrazine |
| 129 | H | 3-(X₃)-1-methyl-6-fluoroindole | 2-(X₄)-pyrazine |
| 131 | H | 3-(X₃)-1-methyl-5-methoxyindole | 2-(X₄)-pyrazine |

-continued

| Compound No. | R² | R³ | R⁴-(Het) |
|---|---|---|---|
| 133 | H | 3-(6-bromo-1-methylindolyl)-X₃ | 2-pyrazinyl-X₄ |
| 134 | H | 3-(4-fluoro-1-methylindolyl)-X₃ | 2-pyrazinyl-X₄ |
| 135 | H | 5-(4-methyl-1H-imidazolyl)-X₃ | 2-pyrazinyl-X₄ |
| 136 | H | 4-(3-phenyl-1H-pyrazolyl)-X₃ | 2-pyrazinyl-X₄ |
| 138 | H | 3-(7-methyl-1-methylindolyl)-X₃ | 2-pyrazinyl-X₄ |
| 139 | H | 5-(1-methyl-pyrrolo-benzodioxole)-X₃ | 2-pyrazinyl-X₄ |
| 140 | H | 3-(4-methoxy-1-methylindolyl)-X₃ | 2-pyrazinyl-X₄ |

-continued
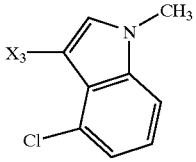
| Compound No. | R² | R³ | R⁴-(Het) |
|---|---|---|---|
| 141 | H | 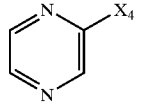 | 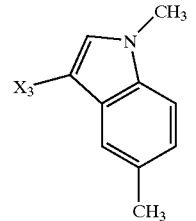 |
| 145 | H | 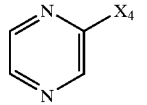 | 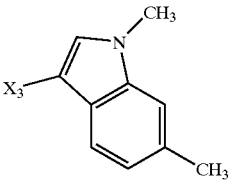 |
| 146 | H | 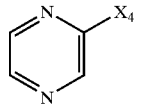 | 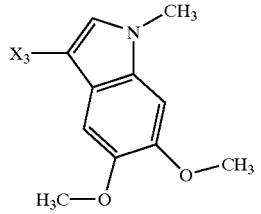 |
| 147 | H | 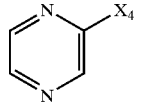 | 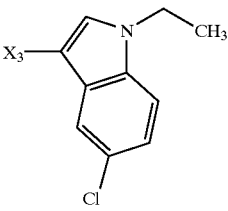 |
| 148 | H | 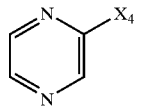 | 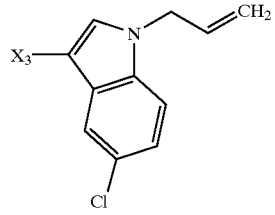 |
| 149 | H | 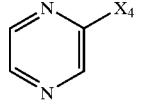 | |

-continued
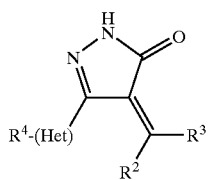
| Compound No. | R² | R³ | R⁴-(Het) |
|---|---|---|---|
| 150 | H | 1-methyl-4-methyl-indol-3-yl (X₃) | pyrazin-2-yl (X₄) |
| 151 | H | 1-methyl-7-azaindol-3-yl (X₃) | pyrazin-2-yl (X₄) |
| 152 | H | 1-methyl-6-trifluoromethyl-indol-3-yl (X₃) | pyrazin-2-yl (X₄) |
| 155 | H | 1-methyl-5-(prop-2-ynyloxy)-indol-3-yl (X₃) | pyrazin-2-yl (X₄) |
| 156 | H | 1-methyl-6-methoxy-indol-3-yl (X₃) | pyrazin-2-yl (X₄) |
| 157 | H | 1-methyl-6-chloro-indol-3-yl (X₃) | pyrazin-2-yl (X₄) |

-continued
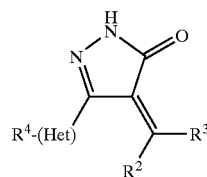
| Compound No. | R² | R³ | R⁴-(Het) |
|---|---|---|---|
| 158 | H | 3-X₃, 1-CH₃, 6-Br indole | 2-X₄ pyrazine |
| 159 | H | 3-X₃, 1-CH₃, 4-Br indole | 2-X₄ pyrazine |
| 160 | H | 3-X₃, 1-CH₃, 5-I indole | 2-X₄ pyrazine |
| 161 | H | 3-X₃, 1-CH₃, 4-OBn indole | 2-X₄ pyrazine |
| 162 | H | 3-X₃, 1-CH₃, 5,6-diF indole | 2-X₄ pyrazine |

-continued
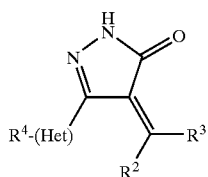
| Compound No. | R² | R³ | R⁴-(Het) |
|---|---|---|---|
| 165 | H | 1-CH₃, 3-X₃, 5-OCH₂-phenyl indole | 2-X₄ pyrazine |
| 167 | H | 1-CH₃, 3-X₃, 6-CH₃ indole | 2-X₄, 3-CH₃ pyrazine |
| 168 | H | 1-CH₃, 3-X₃, 5-Cl indole | 2-X₄, 3-CH₃ pyrazine |
| 169 | H | 1-CH₃, 3-X₃, 4-Br indole | 2-X₄, 3-CH₃ pyrazine |
| 170 | H | 1-CH₃, 3-X₃, 4-NO₂, 5-OCH₃ indole | 2-X₄ pyrazine |

-continued

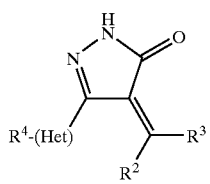

| Compound No. | R² | R³ | R⁴-(Het) |
|---|---|---|---|
| 171 | H | 7-methylindole (X₃ at 3-position) | pyrazine-X₄ |
| 178 | H | 3,5-dimethylpyrrole (X₃ at 2-position) | 3-ethylpyrazine-X₄ |
| 180 | H | 4,7-dimethoxyindole (X₃ at 3-position) | pyrazine-X₄ |
| 184 | H | 3,5-dimethylpyrrole (X₃ at 2-position) | pyrazine-X₄ |
| 185 | H | 1-methylindole (X₃ at 3-position) | pyrazine-X₄ |
| 189 | H | 4-chloro-1-methylindole (X₃ at 3-position) | pyrazine-X₄ |
| 199 | H | 5-iodo-6-methoxy-1-methylindole (X₃ at 3-position) | pyrazine-X₄ |

-continued
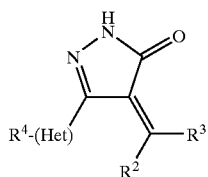
| Compound No. | R² | R³ | R⁴-(Het) |
|---|---|---|---|
| 200 | H | 1-methyl-5-nitro-indol-3-yl (X₃) | pyrazin-2-yl (X₄) |
| 202 | H | 4-chlorophenyl (X₃) | pyrazin-2-yl (X₄) |
| 203 | H | 4-bromo-5-methoxy-1-methyl-indol-3-yl (X₃) | pyrazin-2-yl (X₄) |
| 210 | H | 1-methyl-4-nitro-indol-3-yl (X₃) | pyrazin-2-yl (X₄) |
| 211 | H | 4-methoxycarbonyl-1-methyl-indol-3-yl (X₃) | pyrazin-2-yl (X₄) |
| 212 | H | 5-chloro-4-iodo-1-methyl-indol-3-yl (X₃) | pyrazin-2-yl (X₄) |

-continued
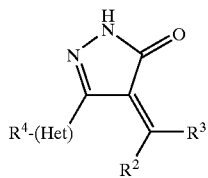
| Compound No. | R² | R³ | R⁴-(Het) |
|---|---|---|---|
| 214 | H | 1-methyl-3-X₃-4-iodo-5-fluoroindole | 2-X₄-pyrazine |
| 215 | H | 1-methyl-3-X₃-6-phenylindole | 2-X₄-pyrazine |
| 216 | H | 1-methyl-3-X₃-4-iodo-6-methylindole | 2-X₄-pyrazine |
| 219 | H | 1-methyl-3-X₃-4-bromo-5-fluoroindole | 2-X₄-pyrazine |
| 222 | H | 1-methyl-3-X₃-6-carboxyindole | 2-X₄-pyrazine |
| 228 | H | 1-methyl-3-X₃-4-bromo-6-methylindole | 2-X₄-pyrazine |

-continued
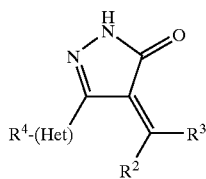
| Compound No. | R² | R³ | R⁴-(Het) |
|---|---|---|---|
| 230 | H | 2,1-dimethyl-1H-indol-3-yl (X₃) | pyrazin-2-yl (X₄) |
| 233 | H | 4-ethoxy-1-methyl-1H-indol-3-yl (X₃) | pyrazin-2-yl (X₄) |
| 237 | H | 1-methyl-5-(methoxycarbonyl)-1H-indol-3-yl (X₃) | pyrazin-2-yl (X₄) |
| 251 | H | 1-methyl-5-carboxy-1H-indol-3-yl (X₃) | pyrazin-2-yl (X₄) |
| 271 | H | 4,7-dimethoxy-1-methyl-1H-indol-3-yl (X₃) | pyrazin-2-yl (X₄) |
| 275 | H | 4,5,6,7-tetrahydro-1H-indol-2-yl (X₃) | pyrazin-2-yl (X₄) |

-continued

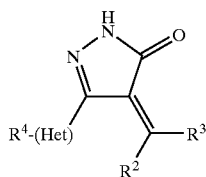

| Compound No. | R² | R³ | R⁴-(Het) |
|---|---|---|---|
| 288 | H | (4-chloro-1-methylindol-3-yl, X₃ attachment) | (pyrazin-2-yl, X₄) |
| 289 | H | (1-methyl-5,6-methylenedioxyindol-7-yl, X₃) | (pyrazin-2-yl, X₄) |
| 290 | H | (2,4-dimethyl-1H-pyrrol-5-yl, X₃) | (pyrazin-2-yl, X₄) |
| 293 | H | (4-ethoxy-1-methylindol-3-yl, X₃) | (pyrazin-2-yl, X₄) | wherein X³ and X⁴ are the attachment point for substituents R³ and R⁴, respectively.

21. A compound selected in accordance with the following table:

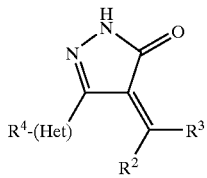

| Compound No. | R² | R³ | R⁴-(Het) |
|---|---|---|---|
| 2 | H | (2,4-dimethyl-1H-pyrrol-5-yl, X₃) | (9H-xanthen-9-yl, X₄) |

-continued
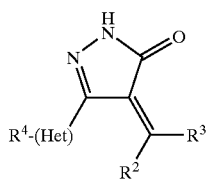
| Compound No. | R² | R³ | R⁴-(Het) |
|---|---|---|---|
| 3 | H | X₃-(2,5-dimethyl-1H-pyrrol-3-yl, NH, 3-CH₃) | 4-pyridyl-X₄ |
| 10 | H | X₃-(2,5-dimethyl-1H-pyrrol-3-yl) | 3-pyridyl-X₄ |
| 23 | H | X₃-(2,5-dimethyl-1H-pyrrol-3-yl) | X₄-(1-methyl-1H-pyrrol-3-yl) |
| 24 | H | X₃-(1H-indol-3-yl) | X₄-(1-methyl-1H-pyrrol-3-yl) |
| 30 | H | X₃-(2,5-dimethyl-1H-pyrrol-3-yl) | 2-pyridyl-X₄ |
| 31 | H | X₃-(4-benzyloxy-1H-indazol-3-yl) | X₄-(1-methyl-1H-pyrrol-3-yl) |
| 32 | H | X₃-(5-fluoro-1H-indol-3-yl) | X₄-(1-methyl-1H-pyrrol-3-yl) |

-continued
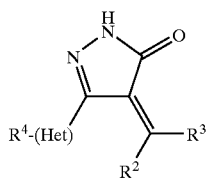
| Compound No. | R² | R³ | R⁴-(Het) |
|---|---|---|---|
| 33 | H | X₃-(3-indolyl, 6-CH₃) | X₄-(1-methyl-pyrrol-3-yl) |
| 34 | H | X₃-(3-indolyl, 7-CH₃) | X₄-(1-methyl-pyrrol-3-yl) |
| 35 | H | X₃-(3-indolyl, 5-Cl) | X₄-(1-methyl-pyrrol-3-yl) |
| 37 | H | X₃-(2,5-dimethyl-3-CH₃-pyrrolyl) | X₄-(thien-3-yl) |
| 38 | H | X₃-(1H-indazol-3-yl) | X₄-(thien-3-yl) |
| 39 | H | X₃-(2,5-dimethyl-3-CH₃-pyrrolyl) | X₄-(benzothien-3-yl) |
| 55 | H | X₃-(2,5-dimethyl-3-CH₃-pyrrolyl) | X₄-(1-methyl-pyrrol-2-yl) |

-continued

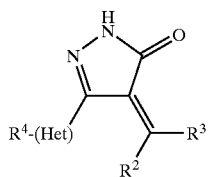

| Compound No. | R² | R³ | R⁴-(Het) |
|---|---|---|---|
| 56 | H | X₃-substituted 5-fluoro-1H-indol-3-yl | 1-methyl-1H-pyrrol-2-yl-X₄ |
| 61 | H | X₃-substituted 3,5-dimethyl-1H-pyrrol-2-yl | thiophen-2-yl-X₄ |
| 62 | H | X₃-substituted 1H-indol-3-yl | thiophen-2-yl-X₄ |
| 63 | H | X₃-substituted 1-methyl-1H-indol-3-yl | thiophen-2-yl-X₄ |
| 66 | H | X₃-substituted 1-(2-cyanoethyl)-1H-indol-3-yl | thiophen-2-yl-X₄ |
| 75 | H | X₃-substituted 1-benzyl-1H-indol-3-yl | thiophen-2-yl-X₄ |
| 76 | H | X₃-substituted 3,5-dimethyl-1H-pyrrol-2-yl | 1H-indol-3-yl-X₄ |

-continued
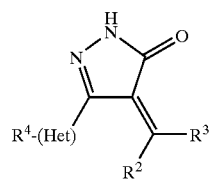
| Compound No. | R² | R³ | R⁴-(Het) |
|---|---|---|---|
| 84 | H | X₃-(2,4-dimethyl-1H-pyrrol-3-yl) | X₄-(3-methyl-1-methyl-1H-pyrazol-5-yl) |
| 85 | H | X₃-(1-methyl-1H-indol-3-yl) | X₄-(3-methyl-1-methyl-1H-pyrazol-5-yl) |
| 96 | H | X₃-(1-methyl-1H-indol-3-yl) | X₄-(1-methyl-5-trifluoromethyl-1H-pyrazol-4-yl) |
| 109 | H | X₃-(5-fluoro-1-methyl-1H-indol-3-yl) | X₄-(thiophen-3-yl) |
| 110 | H | X₃-(5-chloro-1-methyl-1H-indol-3-yl) | X₄-(thiophen-3-yl) |
| 111 | H | X₃-(5-fluoro-1-methyl-1H-indol-3-yl) | X₄-(thiophen-2-yl) |

-continued
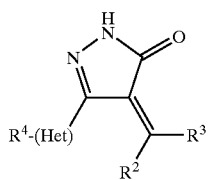
| Compound No. | R² | R³ | R⁴-(Het) |
|---|---|---|---|
| 112 | H | 5-chloro-1-methyl-indol-3-yl (X₃), with CH₃ on N | thien-2-yl (X₄) |
| 176 | H | 2,4-dimethyl-1H-pyrrol-5-yl (X₃) | 5-bromo-pyridin-3-yl (X₄) |
| 205 | H | 4-bromo-1-methyl-indol-3-yl (X₃) | 1-methyl-1H-indazol-3-yl (X₄) |
| 206 | H | 6-fluoro-1-methyl-indol-3-yl (X₃) | 1-methyl-1H-indazol-3-yl (X₄) |
| 207 | H | 1-methyl-indol-3-yl (X₃) | 1-methyl-1H-indazol-3-yl (X₄) |
| 208 | H | 2,4-dimethyl-1H-pyrrol-5-yl (X₃) | 1-methyl-1H-indazol-3-yl (X₄) |
| 291 | H | 4-chloro-1-methyl-indol-3-yl (X₃) | 1-methyl-1H-indazol-3-yl (X₄) |

-continued

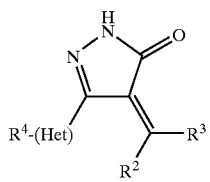

| Compound No. | R² | R³ | R⁴-(Het) |
|---|---|---|---|
| 292 | H | (3-X₃, 1-CH₃, 6-CN indole) | (1-CH₃-indazol-3-yl-X₄) |
| 294 | H | (7-X₃, 1-CH₃ methylenedioxy indole) | (1-CH₃-indazol-3-yl-X₄) |
| 295 | H | (7-X₃, 1-CH₃ methylenedioxy indole) | (2,7-naphthyridin-X₄) | wherein $X^3$ and $X^4$ are the attachment point for substituents $R^3$ and $R^4$, respectively.

22. A pharmaceutical composition comprising a compound of claim 1 and a pharmaceutically acceptable carrier.

23. A pharmaceutical composition comprising a compound of claim 11 and a pharmaceutically acceptable carrier.

24. A pharmaceutical composition comprising a compound of claim 16 and a pharmaceutically acceptable carrier.

25. A pharmaceutical composition comprising a compound of claim 17 and a pharmaceutically acceptable carrier.

26. A pharmaceutical composition comprising a compound of claim 18 and a pharmaceutically acceptable carrier.

27. A pharmaceutical composition comprising a compound of claim 19 and a pharmaceutically acceptable carrier.

28. A pharmaceutical composition comprising a compound of claim 20 and a pharmaceutically acceptable carrier.

29. A pharmaceutical composition comprising a compound of claim 21 and a pharmaceutically acceptable carrier.

* * * * *